US012758225B2

(12) United States Patent
Tsinteris et al.

(10) Patent No.: US 12,758,225 B2
(45) Date of Patent: Oct. 13, 2026

(54) SURGICAL DEVICE FOR PERFORMING COLPOTOMY ON PATIENT

(71) Applicant: HOLOGIC, INC., Marlborough, MA (US)

(72) Inventors: Ion Tsinteris, Marlborough, MA (US); Marco Bedoya, Marlborough, MA (US); Samantha Rogers, Marlborough, MA (US); Catherine Withers, Marlborough, MA (US)

(73) Assignee: Hologic, Inc., Marlborough, MA (US)

(*) Notice: Subject to any disclaimer, the term of this patent is extended or adjusted under 35 U.S.C. 154(b) by 728 days.

(21) Appl. No.: 18/176,426

(22) Filed: Feb. 28, 2023

(65) Prior Publication Data

US 2023/0200816 A1 Jun. 29, 2023

Related U.S. Application Data

(63) Continuation of application No. PCT/US2021/048391, filed on Aug. 31, 2021.
(Continued)

(51) Int. Cl.
*A61B 18/00* (2006.01)
*A61B 17/12* (2006.01)
*A61B 17/00* (2006.01)

(52) U.S. Cl.
CPC .................... *A61B 17/12022* (2013.01); *A61B 2017/00557* (2013.01); *A61B 17/1204* (2013.01); *A61B 2018/00202* (2013.01)

(58) Field of Classification Search
CPC ....... A61B 17/12022; A61B 17/12027–12045; A61B 17/12136; A61B 2018/00285;
(Continued)

(56) References Cited

U.S. PATENT DOCUMENTS

2003/0216727 A1* 11/2003 Long .................. A61B 18/1492 606/41
2007/0250103 A1* 10/2007 Makower ............. A61B 17/072 606/192

(Continued)

FOREIGN PATENT DOCUMENTS

EP 3 400 894 A2 11/2018
EP 3 636 190 A1 4/2020

OTHER PUBLICATIONS

PCT International Search Report for PCT/US2021/048391, Applicant: Hologic, Inc., Form PCT/ISA/210 and 220, dated Mar. 2, 2022 (8 pages).

(Continued)

*Primary Examiner* — Joanne M Rodden
*Assistant Examiner* — Davina E. Lee
(74) *Attorney, Agent, or Firm* — Vista IP Law Group, LLP

(57) ABSTRACT

A colpotomy device includes a shaft assembly having a hollow outer shaft and an inner shaft disposed within, and rotatable and translatable relative to, the outer shaft, a handle assembly operably coupled to a proximal end of the shaft assembly, and configured to selectively rotate the inner shaft relative to the outer shaft, a colpotomy cup assembly including an outer cup and an inner cup disposed within the outer cup, wherein the inner cup is fixedly coupled to a distal end of the inner shaft, and the outer cup is fixedly coupled to a distal end of the outer shaft, and a cutting element coupled to the inner cup, such that the inner shaft the shaft assembly, inner cup, and cutting element rotate together relative to the outer shaft.

20 Claims, 32 Drawing Sheets

Related U.S. Application Data

(60) Provisional application No. 63/136,916, filed on Jan. 13, 2021, provisional application No. 63/073,895, filed on Sep. 2, 2020.

(58) Field of Classification Search
CPC ........... A61B 2018/00202; A61B 2018/00208; A61B 2018/00196; A61B 2018/1475; A61B 2018/00559; A61B 17/4241
See application file for complete search history.

(56) References Cited

U.S. PATENT DOCUMENTS

| | | | | |
|---|---|---|---|---|
| 2012/0143210 | A1 * | 6/2012 | Brecheen | A61B 17/42 606/119 |
| 2014/0276812 | A1 * | 9/2014 | Batchelor | A61B 18/1485 606/48 |
| 2015/0133923 | A1 | 5/2015 | Batchelor et al. | |
| 2016/0206361 | A1 * | 7/2016 | Jadhav | A61B 18/08 |
| 2017/0156756 | A1 * | 6/2017 | Adajar | A61B 18/10 |
| 2018/0325552 | A1 * | 11/2018 | Weihe | A61B 18/1482 |
| 2019/0083133 | A1 * | 3/2019 | Prior | A61B 17/4241 |

OTHER PUBLICATIONS

PCT Written Opinion of the International Search Authority for PCT/US2021/048391, Applicant: Hologic, Inc., Form PCT/ISA/237, dated Mar. 2, 2022 (16 pages).

* cited by examiner

SURGICAL DEVICE FOR PERFORMING COLPOTOMY ON PATIENT

RELATED APPLICATION DATA

The present application is a continuation of International Application No. PCT/US2021/048391, filed Aug. 31, 2021, which claims the benefit under 35 U.S.C. § 119 to U.S. Provisional Patent Application Ser. No. 63/136,916, filed Jan. 13, 2021, and U.S. Provisional Patent Application Ser. No. 63/073,895, filed Sep. 2, 2020, the contents of all of which are hereby incorporated herein by reference in their entirety into the present application.

FIELD

The present disclosure relates generally to surgical devices and techniques, and more specifically to surgical devices and techniques for performing a hysterectomy.

BACKGROUND

Hysterectomy, which is the surgical removal of the uterus, and in some cases the Fallopian tubes and ovaries, is the second most common major operation among women who are of reproductive age in the United States today, second only to cesarean section. According to the National Women's Health Information Center, over 600,000 American women have a hysterectomy every year, totaling more than 5 billion dollars in medical expenses. Approximately 20 million American women have had a hysterectomy, and by the age of 60, one-third of American women will have a hysterectomy. Hysterectomy may be performed for a variety of reasons, including removal of reproductive system cancers, prophylactic treatment for those with a strong history of such cancers, treatment for severe and intractable endometriosis and severe fibroids, chronic pelvic pain, and uterine prolapse.

Hysterectomies may be categorized by the anatomical structures that are removed along with the uterus from the patient. One type of hysterectomy is known as a radical hysterectomy, which involves the complete removal of a patient's uterus, cervix, upper vagina, and parametrium. Another hysterectomy procedure is known as a total hysterectomy, which only involves the complete removal of a patient's uterus and cervix. In some cases, however, a patient may only require supracervical hysterectomy (also known as a partial hysterectomy), which involves the removal of the uterus but otherwise leaves the cervix in situ.

Hysterectomies may also be categorized by the surgical approach utilized to remove the uterus and associated anatomical structures. Many different surgical approaches are available for performing a hysterectomy, and the degree of intrusiveness and recovery time are dependent on the surgical method chosen. Initially, hysterectomy procedures were only performed via an open incision in a patient's abdomen, such that the surgeon can manually access the uterus of the patient (total abdominal hysterectomy (TAH)). About 15% of all hysterectomies in the U.S. are carried out using a TAH procedure, which typically requires a 2-day to 4-day hospital stay, results in a relatively long recovery time (typically 6-8 weeks), and produces large, noticeable, and permanent external scarring. However, a TAH procedure generally requires less surgical skill and time.

With advancement in surgical tools and procedures, less invasive hysterectomy procedures have become popular, owing to faster recovery times, improved cosmesis, and lower risks they afford compared to TAH procedures. The less invasive hysterectomy procedures involve one of three primary approaches: total vaginal hysterectomy (TVH), total laparoscopic hysterectomy (TLH), laparoscopically assisted vaginal hysterectomy (LAVH). Although these less invasive hysterectomy procedures have major advantages over a TAH in that most patients return home the same or next day, with a much shorter recovery period than required for TAH, difficulty may be encountered when employing any of these three hysterectomy techniques due to inherent limitations on visibility, anatomical identification, and the ability to manipulate organs (especially the uterus), and thus, these procedures are surgically more difficult to perform than a TAH.

A TVH procedure involves making an incision in the vagina and removing the uterus and cervix through the vaginal incision. A TVH procedure avoids visible scarring and typically allows for a quicker recovery, as well as less postoperative pain and complications compared to other types of hysterectomies, and is typically the most cost-effective hysterectomy procedure. However, risks associated with a TVH procedure include a slight, but serious risk of shortening or damaging the vagina, which may be caused by the expansion induced to the vaginal area to permit access of the surgeon's hands to the cervical area through the vagina. Furthermore, the choice of the TVH approach is limited, since it is not appropriate if the surgeon requires space to view abdominal anatomical structures, or if there is a danger of the presence of the cancer cells, or if the uterus is not too enlarged, or if the patient has not delivered vaginally.

In a typical TLH procedure, the uterus is accessed through small incisions made in the patient's belly to provide laparoscopic ports for the laparoscopic equipment (which may be robotically assisted), such as for visualization, surgical procedures, and insufflation. Typically, a uterine manipulator, inserted through the vagina, is used to maneuver the uterus and to create space for the laparoscopic equipment and provide access to the desired tissue layers. The uterus and cervix may then be laparoscopically severed from the vagina while the surgeon views the uterus, fallopian tubes and ovaries via a camera attached to a laparoscope. The detached uterus and cervix may then be morcellated and removed through one of the laparoscopic ports or removed through the vagina, depending on the size of the uterus. In some cases, the cervix of the patient may be left intact in a supracervical (subtotal) laparoscopic hysterectomy (LSH). The TLH (or the LSH) approach is considered to be the least invasive, which avoids the open abdominal incision required for TAH procedures and trauma induced to the vaginal area during VH procedures, and generally results in less blood loss, thereby resulting in less patient discomfort, reduced complications, reduced hospital state (on average, one day), and faster return to normal activity (on average, two weeks). The TLH procedure also reduces blood loss compared to a TVH procedure, since it allows a surgeon to detach blood vessels to the uterus.

However, the TLH approach is especially difficult to perform due to a higher degree of difficulty in securing the uterine arteries and ligaments associated with this approach. Furthermore, there may be difficulties in reaching and visualizing parts of the uterus with laparoscopic tools. The posterior side of the uterus is particularly difficult to reach via a TLH procedure, since the visual feedback is poor and special caution is needed to prevent damaging surround structures, such as the bladder or intestines. These limitations lead to relatively longer procedure times. On average, 15-20 minutes of the procedure time is spent resolving difficulties in the actuation separation of the uterus.

An LAVH procedure is similar to the TLH procedure, except that, rather than laparoscopically, the uterus and cervix are severed from inside of the vagina, with the laparoscopic tools only used for guiding the procedure and visualizing structures, in addition to detaching the uterus from surrounding upper supporting structures (such as the infundibular pelvic and round ligaments. The uterus and cervix are then removed through the vagina. In a 1994 study comparing LAVH patients with patients undergoing total abdominal hysterectomies (TAH), it was shown that LAVH patients undergo longer surgical operations and more costly hospital stays, but they also stay in the hospital for significantly less time, have less pain during recovery, and are able to engage in significantly more postoperative activity sooner. Results from a 1997 study comparing patients undergoing LAVH to patients undergoing vaginal hysterectomies showed that although LAVH patients underwent longer, more costly surgery, there was significantly less blood loss associated with the LAVH procedures. Thus, although LAVH procedures may be preferred due to more rapid healing time, less noticeable scarring, less post-operative pain, and less blood loss, the actual surgery time for LAVH procedures are longer than the TAH approach. Because of the longer operation time and use of extra electronic equipment, the LAVH procedure is also costlier than TAH or TVH procedures.

SUMMARY

In a first exemplary embodiment, a colpotomy device is provided for circumferentially incising a vaginal-cervical junction, the colpotomy device including a flexible shaft assembly having a longitudinal axis, the shaft assembly including a hollow outer shaft and an inner shaft disposed within, and rotatable and translatable relative to, the outer shaft. A handle assembly including a handle body is operably coupled to a proximal end of the shaft assembly, wherein the handle assembly is configured to selectively rotate the inner shaft relative to the outer shaft. A colpotomy cup assembly is operably coupled to a proximal end of the shaft assembly and configured for being positioned at a distal end of a vaginal cavity adjacent to the vaginal-cervical junction, the colpotomy cup assembly including an outer cup and an inner cup disposed within the outer cup, wherein the inner cup is fixedly coupled to a distal end of the inner shaft, and the outer cup is fixedly coupled to a distal end of the outer shaft, respectively, of the shaft assembly. A cutting element is coupled to the inner cup, such that the inner shaft, inner cup, and cutting element all rotate together relative to the outer shaft.

The handle assembly may be configured such that rotation of the handle body rotates the inner shaft within the outer shaft about the longitudinal axis of the shaft assembly, wherein the handle body is rotatably engaged with a proximal end of the outer shaft, such that the handle body and the outer shaft are rotatable relative to each other about the longitudinal axis of the shaft assembly. The handle assembly may include a rotational drive assembly affixed within a cavity of the handle body, and wherein the inner shaft is affixed to the rotational drive assembly.

The colpotomy device preferably includes a pneumo-occlusion assembly, the pneumo-occlusion assembly including an inflatable pneumo-occluder disposed around a distal portion of the outer shaft proximal to the colpotomy cup assembly, wherein the pneumo-occluder is configured for providing a seal between the colpotomy device and the vaginal cavity when the colpotomy cup assembly is positioned at an apex of the vaginal cavity. An inflation tube may be provided having a distal end in fluid communication with an interior region of the pneumo-occluder and a proximal end having an inflation port configured for being coupled to a source of fluid. The outer shaft is preferably sufficiently rigid so as to prevent the pneumo-occluder, when expanded, from imposing a frictional force on the inner shaft when the inner shaft is rotated within the outer shaft.

At least a portion of the cutting element is disposed between the inner cup and the outer cup, wherein the cutting element is slidably coupled to the inner cup and configured for being distally advanced from a stored position, in which a distal portion of the cutting element is completely housed within the colpotomy cup assembly, to a deployed position, in which the distal portion of the cutting element extends distally from the colpotomy cup assembly. The distal portion of the cutting element may be provided with a blunt tip configured for causing the vaginal-cervical junction to tent within an abdominal cavity surrounding the vaginal cavity when the blunt tip of the cutting element is distally advanced from the stored position against the vaginal-cervical junction, wherein the cutting element is configured for rotating about the longitudinal axis of the shaft assembly, thereby circumferentially incising the vaginal-cervical junction.

The inner cup may be provided with a channel disposed between a proximal end of the colpotomy cup assembly and a distal end of the colpotomy cup assembly, wherein the distal portion of the cutting element is slidably disposed within the channel, and wherein a proximal portion of the cutting element extends proximally from the colpotomy cup assembly when the cutting element is in the stored position, and is at least partially disposed within the channel when the cutting element is in the deployed position. The channel preferably forms a first acute angle with the longitudinal axis of the shaft assembly, wherein the first acute angle is in a range between 200 and 65°, and a second acute angle with an exterior profile of the colpotomy cup assembly. The exterior profile of the colpotomy cup assembly preferably forms a third acute angle with the longitudinal axis of the shaft assembly.

In various embodiments, the distal portion of the cutting element has a first shear strength and the proximal portion of the cutting element has a second shear strength less than the first shear strength. Without limitation, the cutting element may be monolithic, wherein the distal portion of the cutting element has a first geometric profile, and the proximal portion of the cutting element has a second geometric profile that is smaller than the first geometric profile.

The handle assembly includes a mechanical deployment actuator disposed on the handle body and mechanically coupled to the cutting element, such that the cutting element distally advances from the stored position to the deployed position in response to actuation of the mechanical deployment actuator. The mechanical deployment actuator may be slidable relative to the handle body to distally advance the cutting element from the stored position to the deployed position, and configured for selectively locking the cutting element in one of a plurality of positions between the stored position and the deployed position. The colpotomy device may further include a sleeve slidably disposed around the shaft assembly between the colpotomy cup assembly and the handle assembly, wherein a proximal portion of the cutting element is mechanically coupled to a distal portion of the sleeve and the mechanical deployment actuator is mechanically coupled to a proximal portion of the sleeve, such that when the mechanical deployment actuator is slid in a distal direction relative to the handle body, the sleeve slides distally relative to the shaft assembly, thereby distally advancing the cutting element from the stored position to the distal position.

In some embodiments, the cutting element is an ablation electrode, and the handle assembly has an electrical ablation port disposed on the handle body, the electrical ablation port having a first electrical terminal, the colpotomy device further including a first electrical wire electrically coupled between the first electrical terminal of the electrical ablation port and the ablation electrode, wherein the first electrical wire is associated with an outer surface of the sleeve and the mechanical deployment actuator, such that, when the mechanical deployment actuator is slid in the distal direction relative to the handle body, the sleeve, along with the first electrical wire, slides distally relative to the shaft assembly. Without limitation, the first electrical wire may be spiraled around the electrode sleeve. The electrical ablation port is preferably provided with a second electrical terminal, wherein a ground electrode is mounted to the colpotomy cup assembly, and a second electrical wire electrically coupled between the second electrical terminal of the electrical ablation port and the ground electrode. For example, the sleeve may have a channel extending longitudinally through a wall of the sleeve, wherein the second electrical wire is disposed within the sleeve channel. In various embodiments, the ground electrode is disposed on an inner surface of the inner cup in circumferential alignment with the ablation electrode. For example, the ground electrode may be disposed on a distal-facing surface of the inner cup, such as on a cleaved region on the distal-facing surface of the inner cup that is circumferentially aligned with the ablation electrode. The colpotomy cup assembly may include a reduced-diameter annular boss distally extending from the inner cup, wherein the distal-facing surface of the colpotomy cup assembly is a distal-facing surface of the reduced-diameter annular boss, the colpotomy device further including a raised electrode platform disposed on the reduced-diameter annular boss of the colpotomy cup assembly, the raised electrode platform configured for maintaining a minimum radial distance between the ablation electrode and the ground electrode disposed on the distal-facing surface of the colpotomy cup assembly.

The mechanical deployment actuator may include a deployment mechanism configured for sliding relative to the handle body to distally advance the cutting element from the stored position to the deployed position, the deployment mechanism being mechanically coupled to the proximal portion of the sleeve, such that when the mechanical deployment actuator is slid in the distal direction relative to the handle body, the sleeve slides distally relative to the shaft assembly, thereby distally advancing the cutting element from the stored position to the distal position, and a brake configured for selectively locking the cutting element in one or more positions between the stored position and the deployed position, the brake being mechanically coupled to the proximal portion of the sleeve, such that when the mechanical deployment actuator is slid in the distal direction relative to the handle body, the brake slides relative to the handle body in the distal direction. The shaft assembly is preferably bendable, and the brake is configured for locking the cutting element in place while the deployment mechanism is configured for sliding relative to the handle body when shaft assembly is bent and the handle body is rotated.

In some embodiments, the handle body is provided with slot, wherein the deployment mechanism is a slidable external thumb piece that resides outside of the handle body and a block to which the external thumb piece is affixed, the block being slidably disposed within the slot. The deployment mechanism may be provided with a resilient arm distally extending from the block and affixed to the proximal end of the sleeve.

In some embodiments, the handle body may have a cavity, a pair of slots extending along lateral sides of the cavity, and a series of teeth inset along each of the pair of slots, and wherein the brake includes a block slidably disposed within the cavity, a pair of spring arms extending proximally from the block, the pairs of spring arms respectively having lateral detents that interact with the series of teeth inset along the pair of slots, the brake further including a resilient arm distally extending from the block and affixed to the proximal end of the sleeve.

The colpotomy device may further include a rigid shaft slidably disposed within a lumen of the shaft assembly and extending proximally through the handle assembly, wherein an intrauterine balloon is affixed to a distal end of the rigid shaft distal of the colpotomy cup assembly and configured for being inflated within a uterus accessed through the vaginal cavity, such that the uterus may be mechanically manipulated when the rigid shaft is moved. Preferably, when inflated, the inflated intrauterine balloon is non-compliant, such that when the vaginal-cervical junction is circumferentially incised, the uterus may be removed through the vaginal cavity by proximally displacing the rigid shaft relative to the vaginal cavity while the inflated intrauterine balloon is secured within the uterus. An inflation port may be provided at a proximal end of the rigid shaft and configured for being coupled to a source of fluid, the inflation port being in fluid communication with an interior region of the intrauterine balloon via a lumen extending through the rigid shaft. A second handle assembly may be affixed to a proximal end of the rigid shaft, wherein the second handle assembly includes a locking mechanism is configured for locking the rigid shaft relative to the second handle assembly, thereby locking the intrauterine balloon relative to the colpotomy cup assembly. Without limitation, the locking mechanism may include an eccentric cam and a lever, the eccentric cam being adjacent the rigid shaft, and the lever configured for rotating the eccentric cam about an axis to apply pressure between the eccentric cam and the rigid shaft, thereby locking the rigid shaft relative to the handle body.

The distal portion of the cutting element may be pre-curved, such that a radially outward curvature is imparted on the distal portion of the cutting element as the cutting element is distally advanced from the stored position to the deployed position.

In another exemplary embodiment, a colpotomy device for circumferentially incising a vaginal-cervical junction is provided, the colpotomy device including a shaft assembly having a proximal end, a distal end, and a longitudinal axis. A cutting head is mechanically coupled to the distal end of the shaft assembly, the cutting head configured for being positioned at a distal end of a vaginal cavity adjacent to the vaginal-cervical junction, wherein the cutting head includes a colpotomy cup assembly and a cutting element slidably coupled to the colpotomy cup assembly. The cutting element is configured for being distally advanced from a stored position, in which a distal portion of the cutting element is housed within the colpotomy cup assembly, to a deployed position, in which the distal portion of the cutting element extends distally from the colpotomy cup assembly. The colpotomy device further includes a handle assembly comprising a handle body mechanically coupled to the proximal end of the shaft assembly, a deployment mechanism configured for sliding relative to the handle body to distally advance the cutting element from the stored position to the deployed position, and a brake configured for selectively locking the cutting element in one or more positions between the stored position and the deployed position.

A sleeve may be slidably disposed around the shaft assembly between the colpotomy cup assembly and the handle assembly, with a proximal portion of the cutting element is affixed to a distal portion of the sleeve, and the deployment mechanism mechanically coupled to a proximal portion of the sleeve, such that when the mechanical deployment actuator is slid in a distal direction relative to the handle body, the sleeve slides distally relative to the shaft assembly, thereby distally advancing the cutting element from the stored position to the distal position. The brake may be mechanically coupled to the proximal portion of the sleeve, such that when the mechanical deployment actuator is slid in a distal direction relative to the handle body, the brake slides relative to the handle body in the distal direction.

The shaft assembly is preferably flexible and bendable, and the brake is preferably configured for locking the cutting element in place while the deployment mechanism is configured for sliding relative to the handle body when shaft assembly is bent and the handle body is rotated.

In some embodiments, the handle body has a slot, and wherein the deployment mechanism is in the form of a slidable external thumb piece that resides outside of the handle body, a block to which the external thumb piece is affixed, the block being slidably disposed within the slot, the deployment mechanism further including a resilient arm distally extending from the block and affixed to the proximal end of the sleeve.

In some embodiments, the handle body has a cavity, a pair of slots extending along lateral sides of the cavity, and a series of teeth inset along each of the pair of slots, wherein the brake includes a block slidably disposed within the cavity, a pair of spring arms extending proximally from the block, the pairs of spring arms respectively having lateral detents that interact with the series of teeth inset along the pair of slots, the brake further including a resilient arm distally extending from the block and affixed to the proximal end of the sleeve.

In some embodiments, the cutting element is an ablation electrode, and the handle assembly has an electrical ablation port disposed on the handle body, the electrical ablation port having a first electrical terminal, the colpotomy device further including a first electrical wire electrically coupled between the first electrical terminal of the electrical ablation port and the ablation electrode, wherein the first electrical wire is associated with an outer surface of the sleeve and the mechanical deployment actuator, such that, when the mechanical deployment actuator is slid in the distal direction relative to the handle body, the sleeve, along with the first electrical wire, slides distally relative to the shaft assembly. Without limitation, the first electrical wire may be spiraled around the electrode sleeve. The electrical ablation port is preferably provided with a second electrical terminal, wherein a ground electrode is mounted to the colpotomy cup assembly, and a second electrical wire electrically coupled between the second electrical terminal of the electrical ablation port and the ground electrode. For example, the sleeve may have a channel extending longitudinally through a wall of the sleeve, wherein the second electrical wire is disposed within the sleeve channel.

The colpotomy device preferably includes a pneumo-occlusion assembly, the pneumo-occlusion assembly including an inflatable pneumo-occluder disposed around a distal portion of the outer shaft proximal to the colpotomy cup assembly, wherein the pneumo-occluder is configured for providing a seal between the colpotomy device and the vaginal cavity when the colpotomy cup assembly is positioned at an apex of the vaginal cavity. An inflation tube may be provided having a distal end in fluid communication with an interior region of the pneumo-occluder and a proximal end having an inflation port configured for being coupled to a source of fluid. The outer shaft is preferably sufficiently rigid so as to prevent the pneumo-occluder, when expanded, from imposing a frictional force on the inner shaft when the inner shaft is rotated within the outer shaft.

The colpotomy device may further include a rigid shaft slidably disposed within a lumen of the shaft assembly and extending proximally through the handle assembly, wherein an intrauterine balloon is affixed to a distal end of the rigid shaft distal of the colpotomy cup assembly and configured for being inflated within a uterus accessed through the vaginal cavity, such that the uterus may be mechanically manipulated when the rigid shaft is moved. Preferably, when inflated, the inflated intrauterine balloon is non-compliant, such that when the vaginal-cervical junction is circumferentially incised, the uterus may be removed through the vaginal cavity by proximally displacing the rigid shaft relative to the vaginal cavity while the inflated intrauterine balloon is secured within the uterus. An inflation port may be provided at a proximal end of the rigid shaft and configured for being coupled to a source of fluid, the inflation port being in fluid communication with an interior region of the intrauterine balloon via a lumen extending through the rigid shaft. A second handle assembly may be affixed to a proximal end of the rigid shaft, wherein the second handle assembly includes a locking mechanism is configured for locking the rigid shaft relative to the second handle assembly, thereby locking the intrauterine balloon relative to the colpotomy cup assembly. Without limitation, the locking mechanism may include an eccentric cam and a lever, the eccentric cam being adjacent the rigid shaft, and the lever configured for rotating the eccentric cam about an axis to apply pressure between the eccentric cam and the rigid shaft, thereby locking the rigid shaft relative to the handle body.

In still another exemplary embodiment, a colpotomy device for circumferentially incising a vaginal-cervical junction is provided, the colpotomy device including a shaft assembly having a proximal end, a distal end, and a longitudinal axis. A handle assembly is mechanically coupled to the proximal end of the shaft assembly, and a cutting head mechanically coupled to the distal end of the shaft assembly, the cutting head configured for being positioned at a distal end of a vaginal cavity adjacent the vaginal-cervical junction. The cutting head includes a colpotomy cup assembly having a distal-facing surface, an ablation electrode associated with the colpotomy cup assembly, and a ground electrode having a cleaved region disposed on the distal facing surface of the colpotomy cup assembly in circumferential alignment with the ablation electrode. The handle assembly includes a handle body mechanically coupled to a proximal end of the shaft assembly, an electrical ablation port disposed on the handle body, the electrical ablation port having a first electrical terminal and a second electrical terminal, wherein the colpotomy device includes a first electrical wire electrically coupled between the first electrical terminal of the electrical ablation port and the ablation electrode, and a second electrical wire electrically coupled between the second electrical terminal of the electrical ablation port and the ground electrode.

The ablation electrode may be slidably coupled to the colpotomy cup assembly and configured for being distally advanced from a stored position, in which a distal portion of the ablation electrode is housed within the colpotomy cup assembly, to a deployed position, in which the distal portion of the ablation electrode extends distally from the colpotomy cup assembly. In the deployed position, the ablation electrode forms a first acute angle in a range between 20° and 65° with the longitudinal axis of the shaft assembly. In the stored position, the ablation electrode forms a second acute angle with an exterior profile of the colpotomy cup assembly. An exterior profile of the colpotomy cup assembly forms a third acute angle with the longitudinal axis of the shaft assembly.

The colpotomy cup assembly may have a reduced-diameter annular boss, and the distal-facing surface of the colpotomy cup assembly is a distal-facing surface of the reduced-diameter annular boss. A raised electrode platform is disposed on the reduced-diameter annular boss of the colpotomy cup assembly and configured for maintaining a minimum radial distance between the ablation electrode and the ground electrode disposed on the distal-facing surface of the colpotomy cup assembly.

The colpotomy device may be provided with an inflatable pneumo-occluder disposed around a distal portion of the outer shaft proximal to the colpotomy cup assembly, and an intrauterine balloon is affixed to a distal end of a rigid shaft distal of the colpotomy cup assembly, as described above (and below).

In accordance with yet another exemplary embodiment, a colpotomy device is provided for circumferentially incising a vaginal-cervical junction adjacent a distal end of a vaginal cavity, the colpotomy device including a shaft assembly having a proximal end, a distal end, and a longitudinal axis. A handle assembly is mechanically coupled to the proximal end of the shaft assembly, and a cutting head is mechanically coupled to the distal end of the shaft assembly. The cutting head being configured for being positioned at the distal end of a vaginal cavity adjacent the vaginal-cervical junction, and includes a colpotomy cup assembly and a cutting element slidably coupled to the colpotomy cup assembly. The cutting element configured for being distally advanced from a stored position, in which a distal portion of the cutting element is housed within the colpotomy cup assembly, to a deployed position, in which the distal portion of the cutting element extends distally from the colpotomy cup assembly. The distal portion of the cutting element is pre-curved, such that a radially outward curvature is imparted on the distal portion of the cutting element as the cutting element is distally advanced from the stored position to the deployed position. The cutting element is configured for rotating about the longitudinal axis of the shaft assembly, thereby circumferentially incising a vaginal-cervical junction. When the cutting element is in the deployed position, an acute angle in a range between 20° and 65° is formed between a tangent at a distal tip of the cutting element and the longitudinal axis of the shaft assembly.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects of the disclosed inventions are obtained, a more particular description of the disclosed inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

DETAILED DESCRIPTION OF THE ILLUSTRATED EMBODIMENTS

Figure 1:
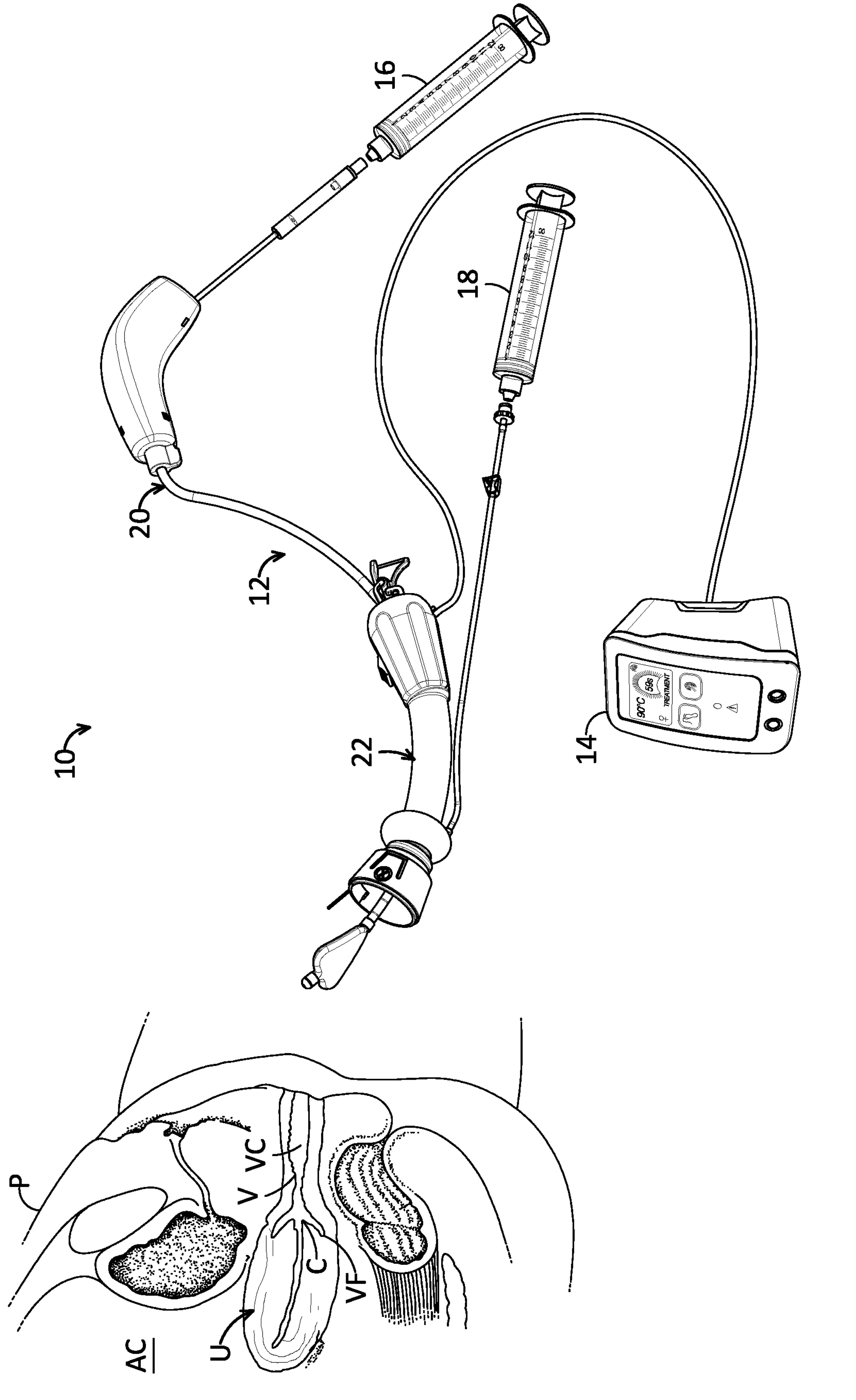
FIG. 1 is a perspective view of a hysterectomy system constructed in accordance with one embodiment of the disclosed inventions.

Referring to FIG. 1, one embodiment of a hysterectomy system 10 that is capable of transvaginally severing a uterus U and cervix C from the vagina V of a female patient P will now be described. The hysterectomy system 10 particularly lends itself well for use in laparoscopically assisted vaginal hysterectomy (LAVH) procedures (i.e., the uterus U, along with the cervix C, is severed from within the vagina V, while the procedure is performed under laparoscopic guidance and visualization). However, it should be appreciated that the use of the hysterectomy system 10 should not be so limited, and thus, may be used for other types of hysterectomy procedures, including total vaginal hysterectomy (TVH) procedures, or even radical hysterectomy procedures where the ovaries and fallopian tubes of the patient P are to be severed and removed, either laparoscopically or transvaginally.

The hysterectomy system 10 includes a colpotomy assembly (or "device") 12 configured for being inserted within the vaginal cavity VC of the patient P for circumferentially incising the vaginal-cervical junction J (i.e., the region between the vagina V and cervix C), thereby transecting the uterus U and cervix C from the vagina V of the patient P. As will be described in further detail below, the colpotomy assembly 12 is configured for incising the vaginal-cervical junction J in a very repeatable and precise manner, thereby decreasing reducing operational time and necessary surgical skill required to perform an LAVH. As such, the colpotomy assembly 12 improves upon existing LAVH procedures, which already have faster recovery times, improved cosmesis, and lower risks compared to total abdominal hysterectomy (TAH) procedures, by eliminating or at least closing the gap between LAVH procedures and TAH procedures with regard to operational time and skill.

In this embodiment of the hysterectomy system 10, the colpotomy assembly 12 is configured for circumferentially incising the vaginal-cervical junction J of the patient P via electrocautery, and thus, the hysterectomy system 10 further comprises a radio frequency (RF) generator 14 configured for providing RF ablation energy to the colpotomy assembly 12 to facilitate severing of the uterus U and cervix C from the vagina V. The RF generator 14 may be a conventional RF power supply that operates at a suitable frequency (e.g., in the range of 200 KHz to 1.25 MHz) with a conventional sinusoidal or non-sinusoidal wave form. Such power supplies are available from many commercial suppliers, such as Valleylab, Aspen, and Bovie. The RF generator 14 will typically be operated at the lower end of the voltage and power capability (e.g., below 150 volts, usually between 50 volts and 100 volts, and at a power from 20 watts to 200 watts). In alternative embodiments, the colpotomy assembly 12 may be capable of mechanically severing the uterus U and cervix C from the vagina V of the patient P without using an RF generator.

The colpotomy assembly 12 may be configured for gripping or manipulating the uterus U during the hysterectomy procedure, and to this extent, may also serve as a uterine manipulator, e.g., to move the intact uterus U around through engagement of the interior wall of the uterus U while performing adjunct laparoscopic functions, such as visualizing anatomical structures (e.g., the bladder or intestines) and/or dissecting tissue associated with the uterus U (e.g., connective tissue and blood vessels). Under appropriate circumstances (e.g., if the uterus U is small enough relative to the vaginal cavity VC, typically less than about 250 grams), the colpotomy assembly 12 may be configured for removing the severed uterus U, along with the cervix C, through the vaginal cavity VC. In this case, the hysterectomy system 10 further comprises a first source of fluid 16 (e.g., a syringe (filled with inflation gas or fluid, such as saline)) configured for inflating a balloon (described in further detail below) at the distal tip of the colpotomy assembly 12 to engage the interior wall of the uterus U and facilitate pulling the separated uterus U and cervix C out of the patient P via the vaginal cavity VC without the use of a tenaculum or need for sutures.

In the case where the abdomen of the patient is insufflated (i.e., introducing a vapor or gas (e.g., carbon dioxide) into the abdomen to expand the abdominal cavity AC, thereby creating a pneumoperitoneum that provides a physician visibility within the abdominal cavity AC during a LAVH procedure), the colpotomy assembly 12 may be further configured for occluding the vaginal cavity VC to prevent insufflation gas from escaping the abdominal cavity AC of the patient P, and thus preventing loss of pneumoperitoneum, as the vaginal-cervical junction J of the patient P is being circumferentially incised during the LAVH procedure. To this end, the hysterectomy system 10 may further comprise a second source of fluid 18 (e.g., a syringe (filled with inflation gas or fluid, such as saline)) configured for inflating another balloon (described in further detail below) to facilitate occlusion of the vaginal cavity VC.

Additionally, the hysterectomy system 10 may comprise monitors, a foot switch, an instrument table, and an operating table (all not shown) on which the patient P will be placed.

The colpotomy assembly 12 generally comprises a uterine manipulator 20 including a rigid shaft 24 and a tissue cutting device 22 that is slidably disposed over the rigid shaft 24. A distal end of the uterine manipulator 20 can be secured within the uterus U of the patient P for manipulating the uterus U, while the tissue cutting device 22 may be secured within the vaginal cavity VC of the patient P relative to the uterine manipulator 20 for circumferentially incising the vaginal-cervical junction J, and thereby separating the uterus U and cervix C from the vagina V for subsequent removal from the patient P through the vaginal cavity VC with the uterine manipulator 20. In at least one embodiment, some or all of the components of either the uterine manipulator 20 or the tissue cutting device 22 may be disposable. Some of the components of the uterine manipulator 20 or the tissue cutting device 22 may be removable from one another, so that disposable components can be uncoupled from permanent components and replaced with new disposable components.

Figure 2:
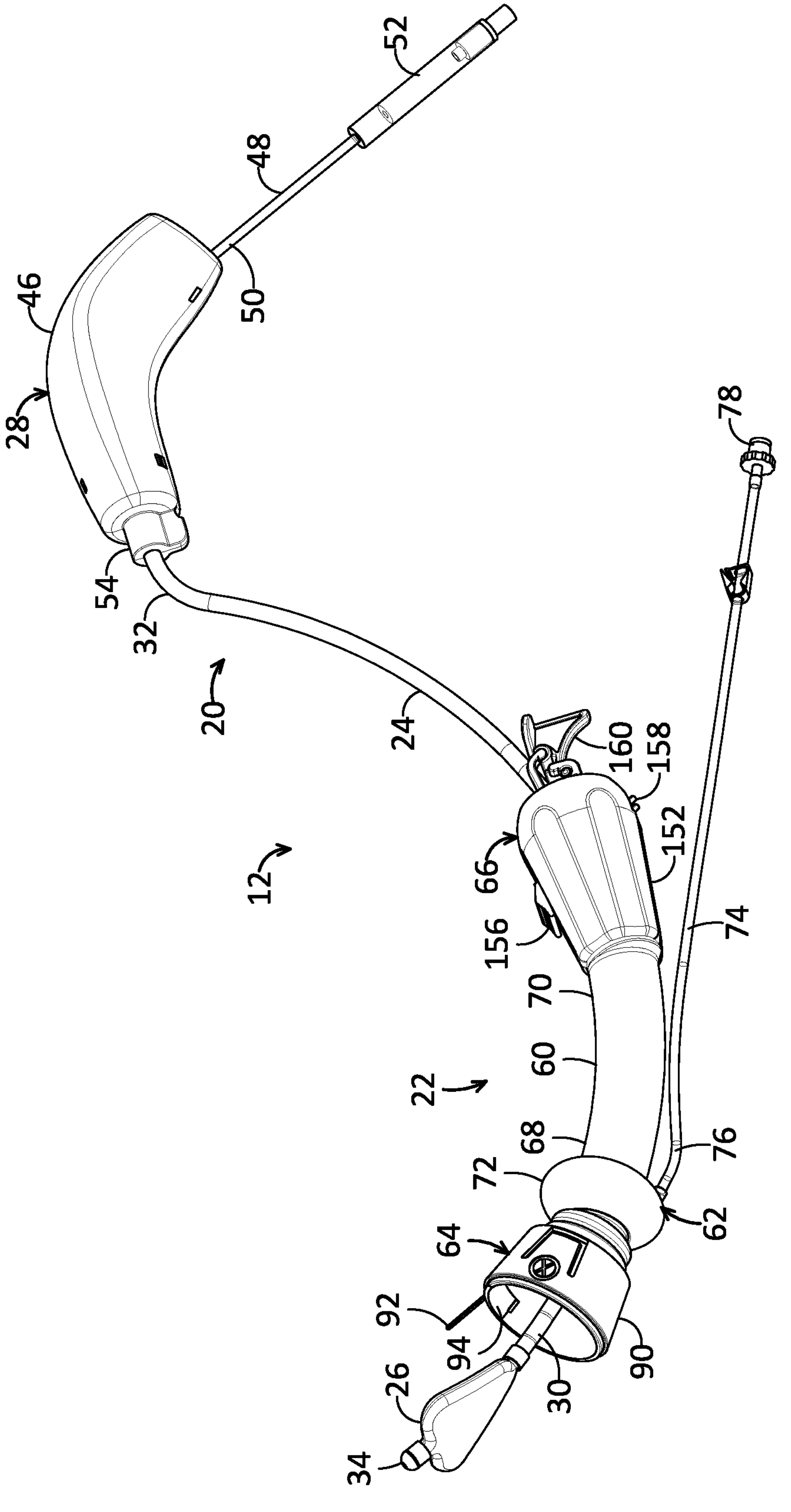
FIG. 2 is a top perspective view of a colpotomy assembly used in the hysterectomy system of FIG. 1.
Figure 3:
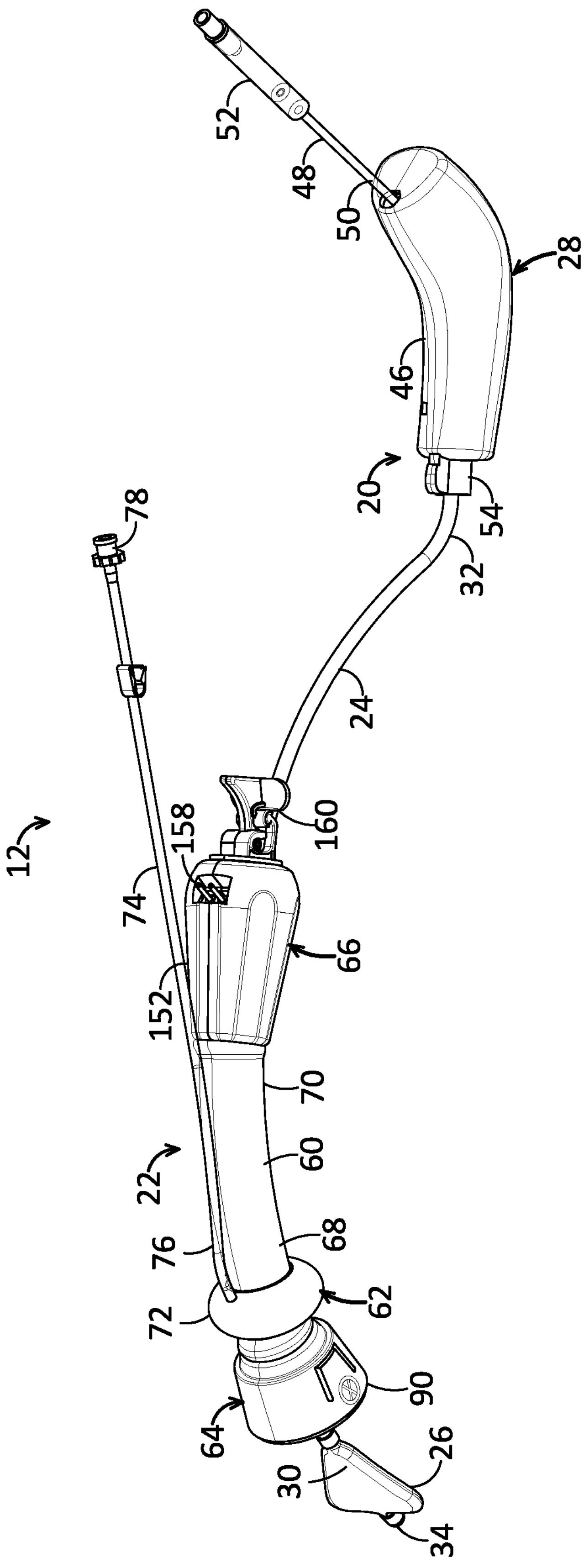
FIG. 3 is a bottom perspective view of a colpotomy assembly used in the hysterectomy system of FIG. 1.
Figure 4:
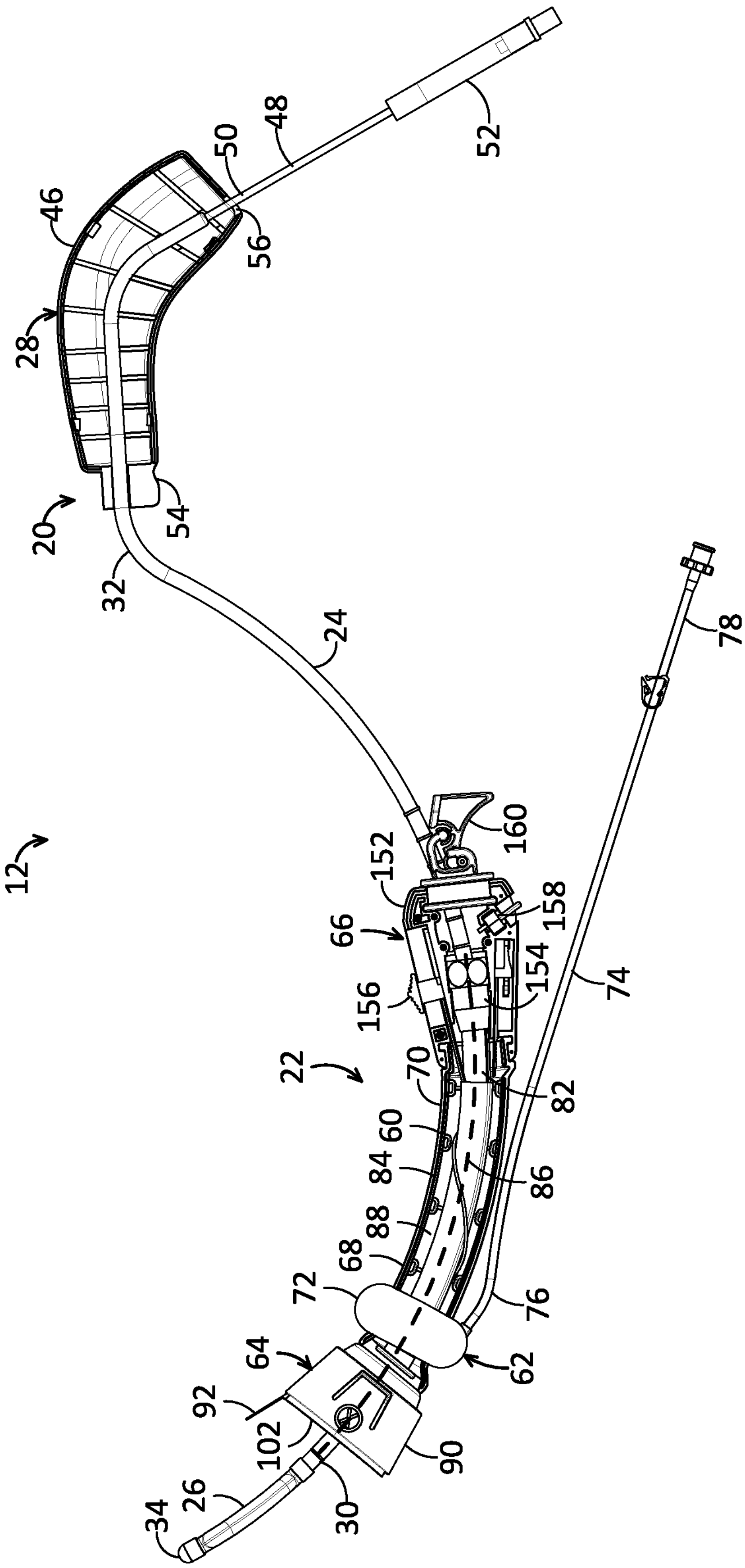
FIG. 4 is a cut-away view of the colpotomy assembly of FIG. 2.

Referring to FIGS. 2-4, the uterine manipulator 20 of the colpotomy assembly 12 comprises the rigid shaft 24 having a distal end 30 and a proximal end 32, an intrauterine balloon 26 affixed to the distal end 30 of the rigid shaft 24, and a handle assembly 28 affixed to the proximal end 32 of the rigid shaft 24.

In the illustrated embodiment, the rigid shaft 24 is generally S-shaped to provide superior insertion and manipulation for the physician from a lap position. Preferably, the rigid shaft 24 has an atraumatic distal tip 34, thereby facilitating insertion of the intrauterine balloon 26 through the vaginal cavity VC, then guided through the cervix C, and into the uterus U, while minimizing tissue trauma to these anatomical structures. The rigid shaft 24 is hollow and comprises an inflation lumen (not shown) extending between the proximal end 32 of the rigid shaft 24 within the handle assembly 28 and the distal end 30 of the rigid shaft 24 at the intrauterine balloon 26. The rigid shaft 24 may have any desired cross-sectional shape of a desired dimension, so long as it may be received within the vaginal cavity VC of the patient P. The rigid shaft 24 may have an atraumatic exterior configuration, which may include, but not limited to, a rounded exterior surface. The rigid shaft 24 may have any suitable coating, such as, e.g., an anesthetic or lubricious coating on the exterior surface of the rigid shaft 24.

Figure 5:
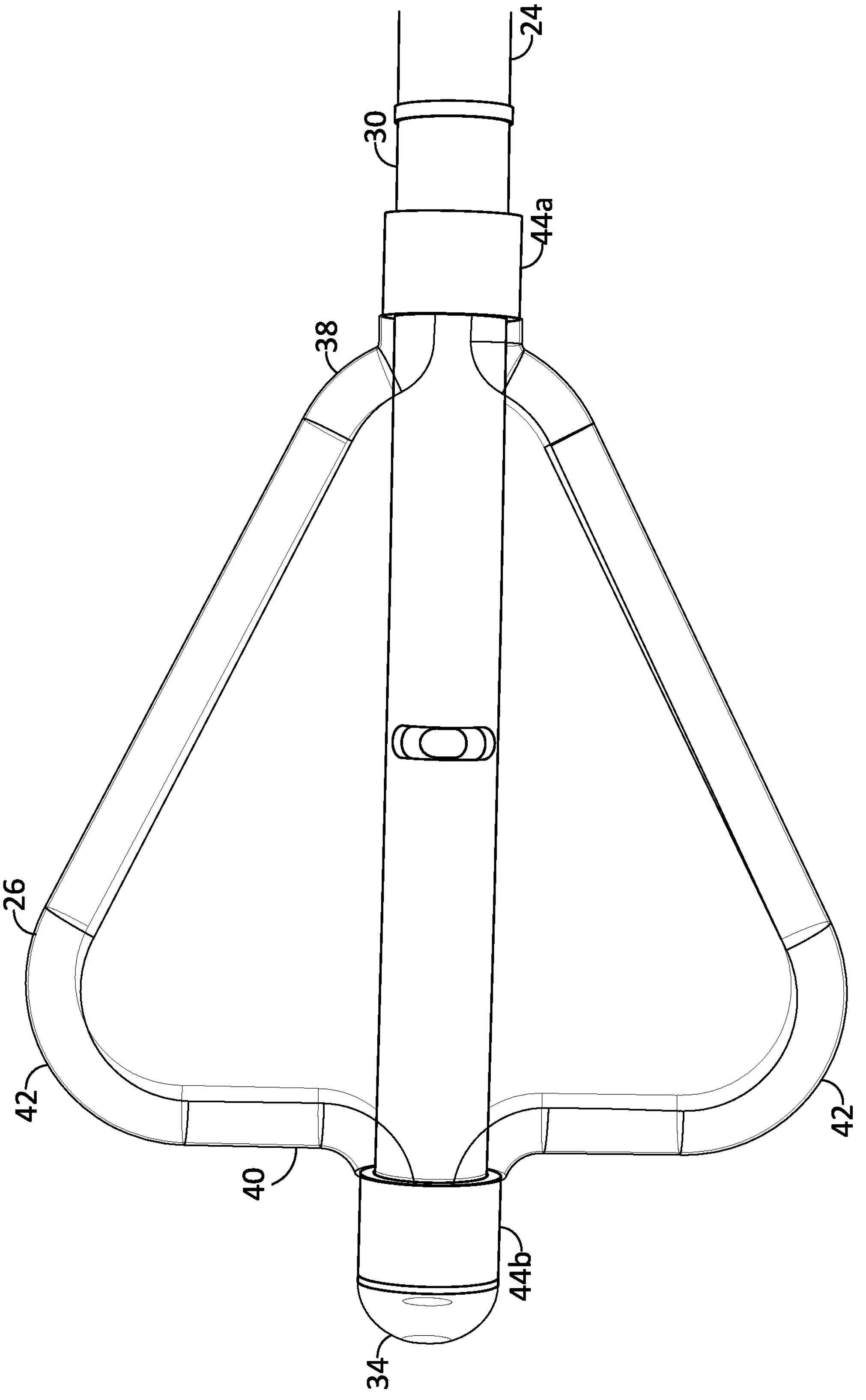
FIG. 5 is a plan view of an intrauterine balloon of a uterine manipulator used in the hysterectomy system of FIG. 1.

Referring further to FIG. 5, the rigid shaft 24 further comprises a distal inflation port 36 formed through the wall of the rigid shaft 24 at the intrauterine balloon 26, such that the inflation lumen extending through the rigid shaft 24 is in constant fluid communication with an interior of the intrauterine balloon 26. In one advantageous embodiment, the intrauterine balloon 26 is triangular in shape, thereby mimicking the interior contour of the uterus U. In the illustrated embodiment, the shape of the intrauterine balloon 26 is similar an isosceles triangle, with a proximal end 38 of the intrauterine balloon 26 forming the vertex of the isosceles triangle, and a distal end 40 of the intrauterine balloon 26 forming the base of the isosceles triangle. In alternative embodiments, the shape of the intrauterine balloon 26 may be similar to an equilateral triangle, or even a scalene triangle.

The intrauterine balloon 26 comprises corners 42 that correspond to the base angles of the isosceles triangle, which may be rounded or cutoff to better mimic that interior contour of the uterus U. In the illustrated embodiment, the proximal end 38 of the intrauterine balloon 26 corresponding to the vertex of the isosceles triangle is affixed to the distal end 30 of the rigid shaft 24 via a first retention band **44*a*, while the distal end 40 of the intrauterine balloon 26 corresponding to the base of the isosceles triangle is cinched and affixed to the distal end 30 of the rigid shaft 24 via a second retention band 44*b*, such that the distal end 30 of the rigid shaft 24, with the exception of the atraumatic distal tip 34, extends within the interior of the intrauterine balloon 26. In an alternative embodiment, the distal end 40 of the intrauterine balloon 26 is not affixed to the rigid shaft 24, but rather may be disposed, unaffixed, distal to the distal tip 34 of the rigid shaft 24**, which may or may not be atraumatic.

Unlike conforming balloons on prior art uterine manipulators that readily adapt to body structures, the intrauterine balloon 26 is non-compliant. The intrauterine balloon 26 resists or minimizes axial displacement of the rigid shaft 24 relative to the intrauterine balloon 26 below a threshold proximal force. In this manner, the uterus U along with the cervix C, after being separated from the vagina V, may be pulled through vaginal cavity VC by overcoming frictional forces between the exterior of the uterus U and the inner surface of the vagina V. For example, when the intrauterine balloon 26 is fully inflated and disposed within the uterus U, the rigid shaft 24 may be subject to a proximally directed axial force up to 6-10 pounds-force, but preferably at least 8 pounds-force below which the rigid shaft 24 does not move relative to the balloon 26.

For the purposes of this specification, the term "non-compliant" means that the intrauterine balloon 26 expands to a predetermined expanded shape upon initial inflation, e.g., to a threshold pressure, or in other words, the stiffness of the intrauterine balloon 26 only increases as the pressure within the intrauterine balloon 26 increases while maintaining the predetermined shape. If the pressure is increased beyond the threshold pressure, the size and/or shape of the intrauterine balloon 26 may change. For example, the wall of the intrauterine balloon 26 may be formed from substantially inelastic material configured for providing initial expansion and internal pressure and substantially maintain the predetermined expanded shape with minimal additional expansion, e.g., until a rupture or failure pressure is attained, which in the illustrated embodiment may be between about five and twenty-five atmospheres (5-25 atm).

Referring specifically to FIGS. 2 and 3, the handle assembly 28 comprises a handle body 46 and a flexible fluid conduit 48 having a distal end 50 affixed to the proximal end 32 of the rigid shaft 24, and a proximal adapter 52 configured being mated to the first source of fluid 16 (shown in FIG. 1), such that the first source of fluid 16 can be placed in fluid communication with the inflation lumen of the rigid shaft 24, and thus, the interior region of the intrauterine balloon 26 via the distal inflation port 36. The handle body 46 is preferably shaped to be ergonomic for the physician while standing on the side the patient P or sitting/standing between her legs.

In the example embodiment, the handle body 46 comprises two halves that are affixed to each other in a clamshell arrangement, although in alternative embodiments, the handle body 66 may be molded as a single piece. In the illustrated embodiment, the handle body 46 is hollow, thereby housing the proximal end 32 of the rigid shaft 24 and the distal end of the fluid conduit 48 therein. The handle assembly 28 further comprises a distal retainer 54 in which the proximal end 32 of the rigid shaft 24 is affixed, such that the rigid shaft 24 stably responds to movement of the handle body 46. The handle assembly 28 further comprises an opening 56 (shown in FIG. 4) through which the fluid conduit 48 extends.

The tissue cutting device 22 of the colpotomy assembly 12 generally comprises a shaft assembly 60 having a distal end 68 and a proximal end 70, a pneumo-occlusion assembly 62 disposed on the shaft assembly 60, a cutting head 64 affixed to the distal end 68 of the shaft assembly 60, and a handle assembly 66 affixed to the proximal end 70 of the shaft assembly 60. Although not essential, the shaft assembly 60 is preferably flexible and bendable.

The pneumo-occlusion assembly 62 comprises a pneumo-occluder 72, which, in the illustrated embodiment, takes the form of an inflatable balloon, an inflation conduit 74 having a distal end 76 affixed to the pneumo-occluder 72, and a proximal adapter 78 configured being mated to the second source of fluid 18, such that the second source of fluid 18 can be selectively placed in fluid communication with the interior region of the pneumo-occluder 72.

The pneumo-occluder 72 is disposed around the shaft assembly 60 between the cutting head 64 and the handle assembly 66. In the illustrated embodiment, the pneumo-occluder 72 is permanently affixed to the shaft assembly 60, e.g., just proximal to the cutting head 64. The pneumo-occluder 72 may comprise any suitable geometric shape (e.g., a sphere, ovoid, cylinder, cone, tori (toroidal), bulb, ring, or wheel, but in the illustrated embodiment is toroidal or donut-shaped. The pneumo-occluder 72 is preferably compliant, thereby facilitating a seal between the tissue cutting device 22 and the wall of the vaginal cavity VC of the patient P, and as a result, minimizing the risk of losing pneumoperitoneum (i.e., loss of insufflation via fluid communication between the abdominal cavity AC and the vaginal cavity VC of the patient P) during the hysterectomy procedure. For the purposes of this specification, "compliant" means that the balloon, when fully inflated, is bendable, deformable, manipulatable, and soft to enable conforming to the contours of the vaginal cavity VC, while yet able to spring back into shape after bending, stretching or being compressed to conform to the vaginal cavity VC.

Figure 6:
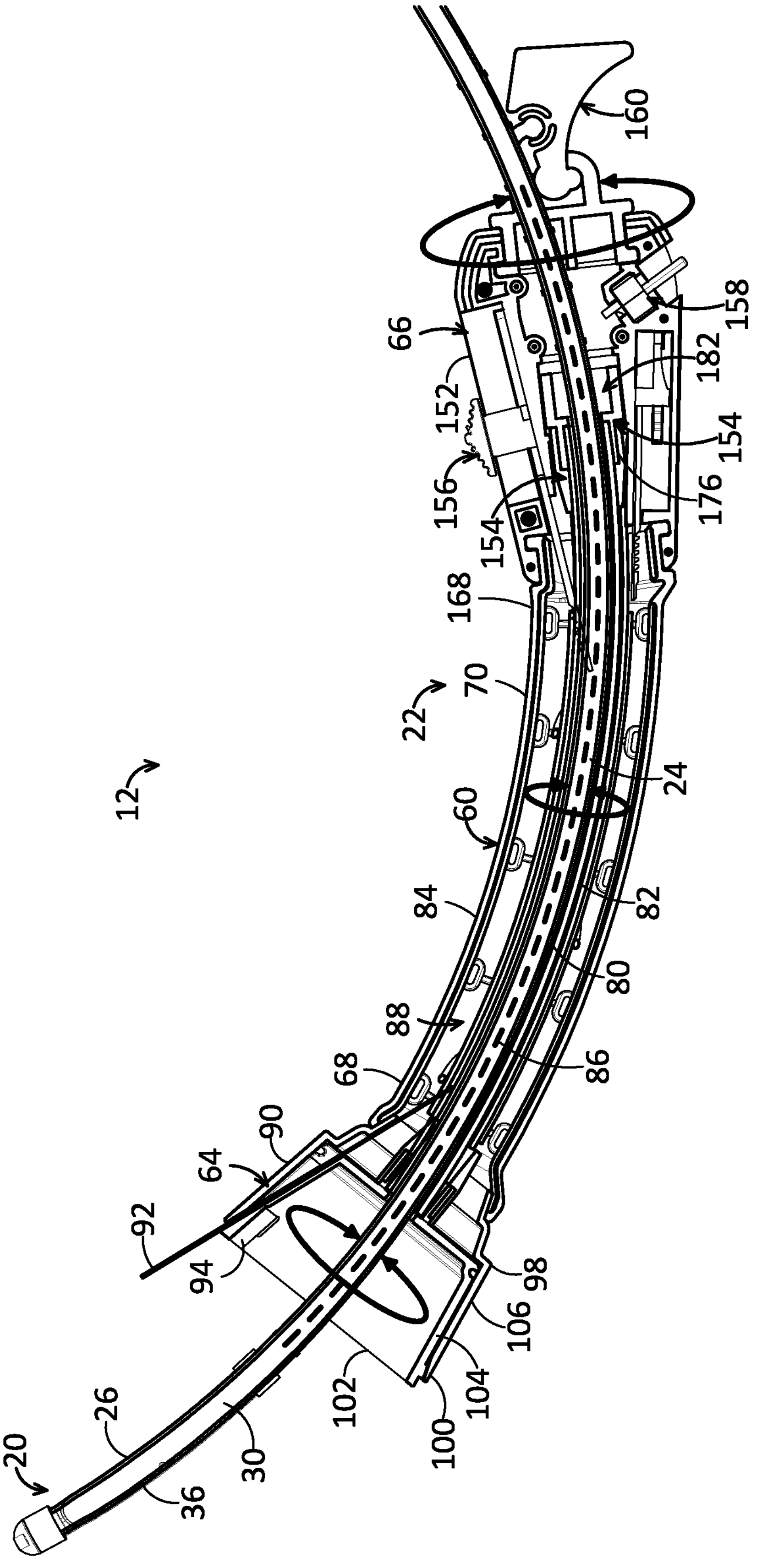
FIG. 6 is a cut-away view of a tissue cutting device of the colpotomy assembly of FIG. 2.

Referring specifically to FIGS. 4 and 6, the shaft assembly 60 comprises a lumen 80 slidably disposed over the rigid shaft 24 of the uterine manipulator 20, such that the tissue cutting device 22 may be freely displaced along the rigid shaft 24 in either the distal direction or proximal direction until the locked, as will be described in further detail below. The shaft assembly 60 may have any desired cross-sectional shape of a desired dimension, so long as it may be received within the vaginal cavity VC of the patient P.

In the illustrated embodiment, the shaft assembly 60 has a composite structure, and comprises an inner shaft 82 and an outer shaft 84 coaxially disposed around the inner shaft 82. As will be described in further detail below, the inner shaft 82 is rotatably disposed within the outer shaft 84 about a longitudinal axis 86 of the shaft assembly 60 to actuate the tissue cutting functionality of the colpotomy assembly 12.

The inner shaft 82 may be composed of any suitable inert and biocompatible material that provides the necessary flexibility to the shaft assembly 60, while also transmitting torque through the length of the inner shaft 82. The outer shaft 84 takes the form of an outer shell disposed around the inner shaft 82 and extends between the cutting head 64 and the handle assembly 66. The inner shaft 82 and the outer shaft 84 define an annular space 88 between the outer shaft 84 and the inner shaft 82. The outer shaft 84 is sufficiently rigid to prevent the pneumo-occluder 72, when expanded, from imposing a frictional force on the inner shaft 82 when the inner shaft 82 and outer shaft 84 are rotated relative to each other about the longitudinal axis 86 of the shaft assembly 60.

Figure 7:
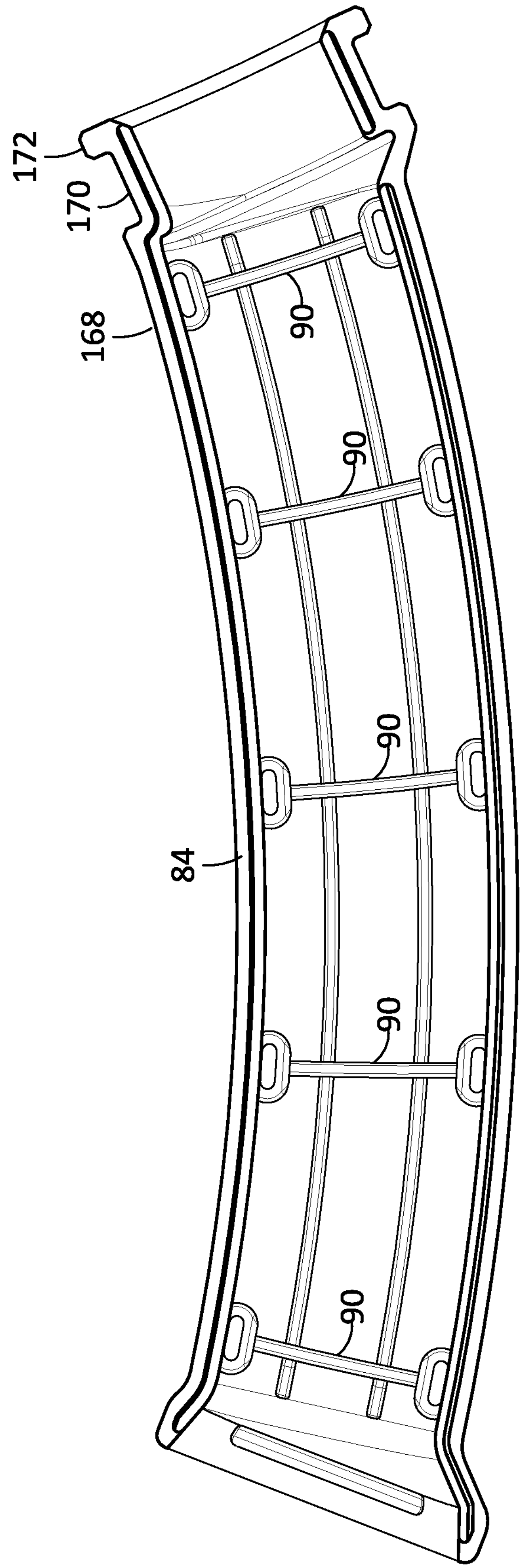
FIG. 7 is a cut-away view of an outer shaft of a shaft assembly used in the tissue cutting device of FIG. 6.

The outer shaft 84 has a series of annular ribs 90 (best shown in FIG. 7) extending along its length, increasing the shear strength of the outer shaft 84, while maintaining lateral flexibility along the length of the outer shaft 84. The outer shaft 84 may be composed of any suitable inert and biocompatible material that provides the necessary flexibility to the shaft assembly 60.

Figure 8:
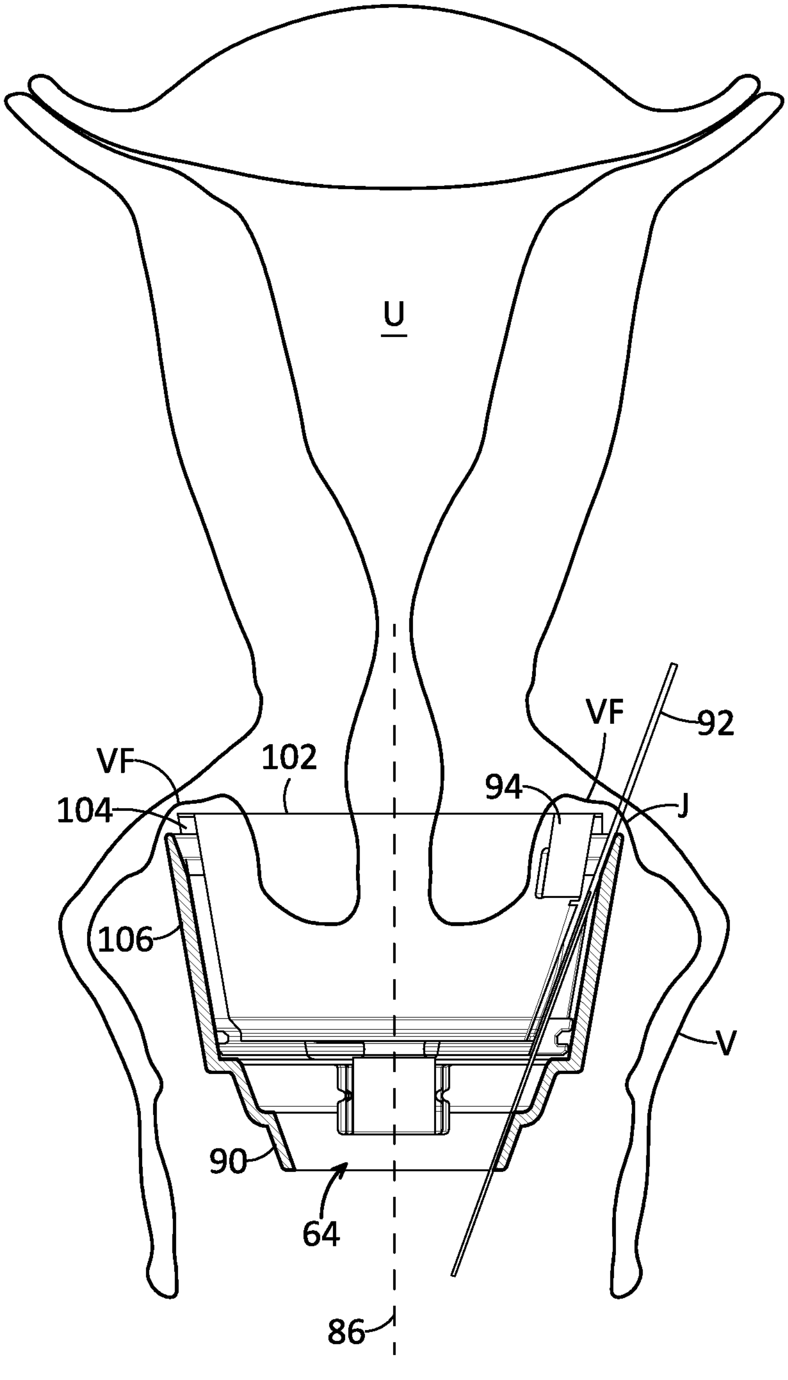
FIG. 8 is a plan view of a cutting head of the tissue cutting device of FIG. 6 in relation to the anatomy of a female patient.

As best shown in FIG. 8, the cutting head 64 is configured for being positioned at the vaginal fornices VF (i.e., the superior (or deepest) portions of the vagina V extending into the recesses created by the vaginal portion of the cervix C, which consist of the larger anterior fornix, the posterior fornix, and two lateral fornices) between the cervix C and the vagina V of the patient P, and being operated to circumferentially incise the vaginal-cervical junction J of the patient P.

In the illustrated embodiment, the cutting head 64 is permanently affixed to the distal end 68 of the shaft assembly 60, although in alternative embodiments, the cutting head 64 is detachable or disconnectable from the distal end 68 of the shaft assembly 60, such that the cutting head 64 can be sterilized and re-used, removed from the distal end 68 of the shaft assembly 60 and be disposed, or be made to be interchangeable with other cutting heads in a variety of dimensions, such that the physician can select an appropriately sized cutting head 64 to suit the size of the vaginal cavity VC of the patient P.

The cutting head 64 generally comprises a colpotomy cup assembly 90 and a cutting element 92 configured for puncturing through the vaginal-cervical junction J of the patient P after the cutting head 64 has been positioned at the vaginal fornices VF and rotated about the longitudinal axis 86 of the shaft assembly 60, thereby creating a circumferential incision through the vaginal-cervical junction J and transecting the uterus U and cervix C from the vagina V of the patient P, as will be described in further detail below. As will also be described in further detail below, the cutting element 92 serves as an ablation electrode that is operated in a bipolar mode, and thus, the cutting head 64 further comprises a ground electrode 94 affixed to the colpotomy cup assembly 90 adjacent to the cutting element 92.

The colpotomy cup assembly 90 may have any suitable shape, configuration, and/or dimension, such that the colpotomy cup assembly 90 can be received in the vaginal cavity VC of the patient P. In the illustrated embodiment, the colpotomy cup assembly 90 has a substantially conical shape that tapers distally outward to an enlarged distal rim 102. The distal rim 102 of the colpotomy cup assembly 90 may have a suitable diameter, e.g., in the range of 2.5 cm-4.0 cm.

Figure 13A:
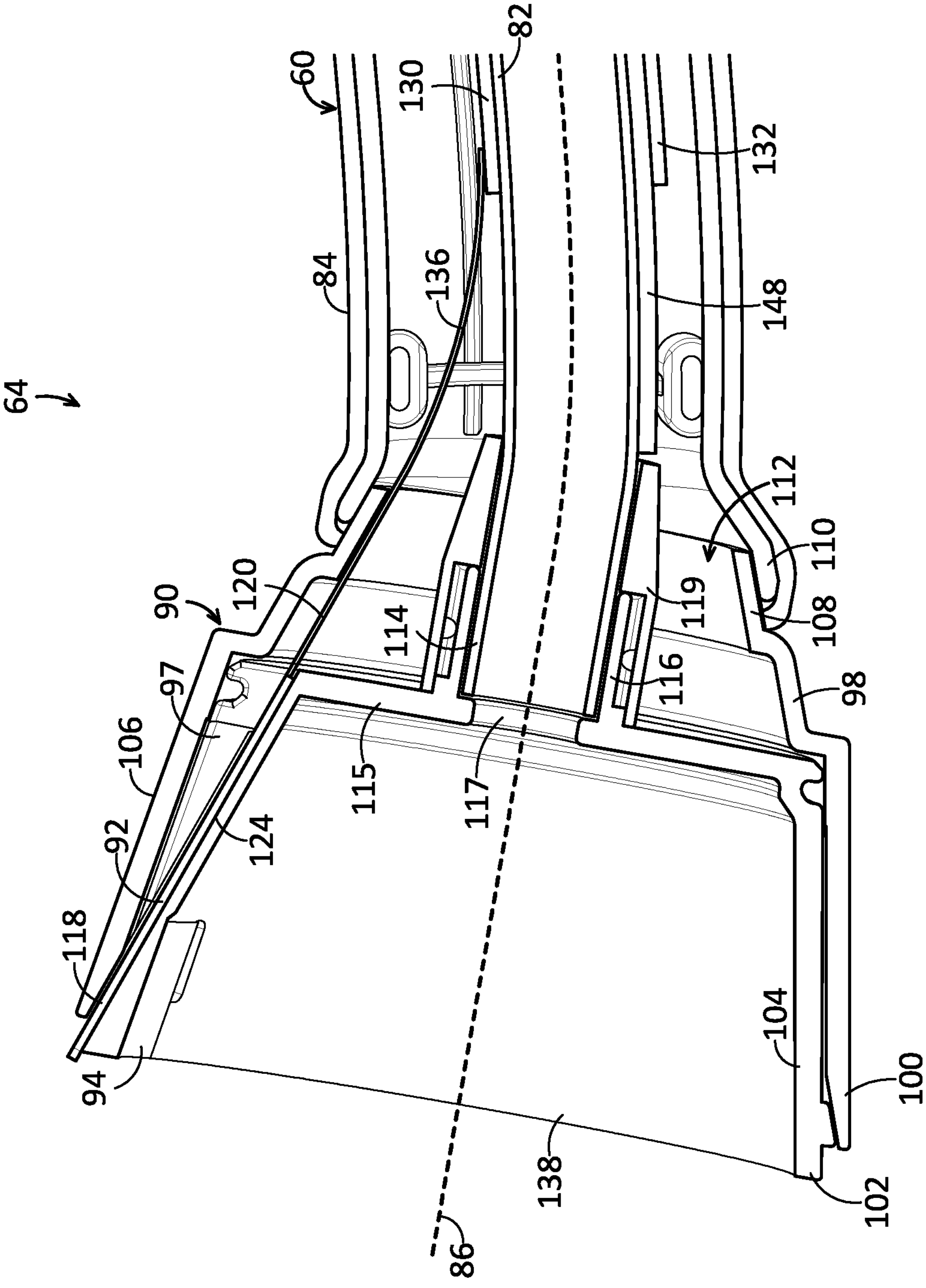
FIG. 13A is a cut-away view of the cutting head of FIG. 8, particularly showing the cutting element in a stored position.
Figure 13B:
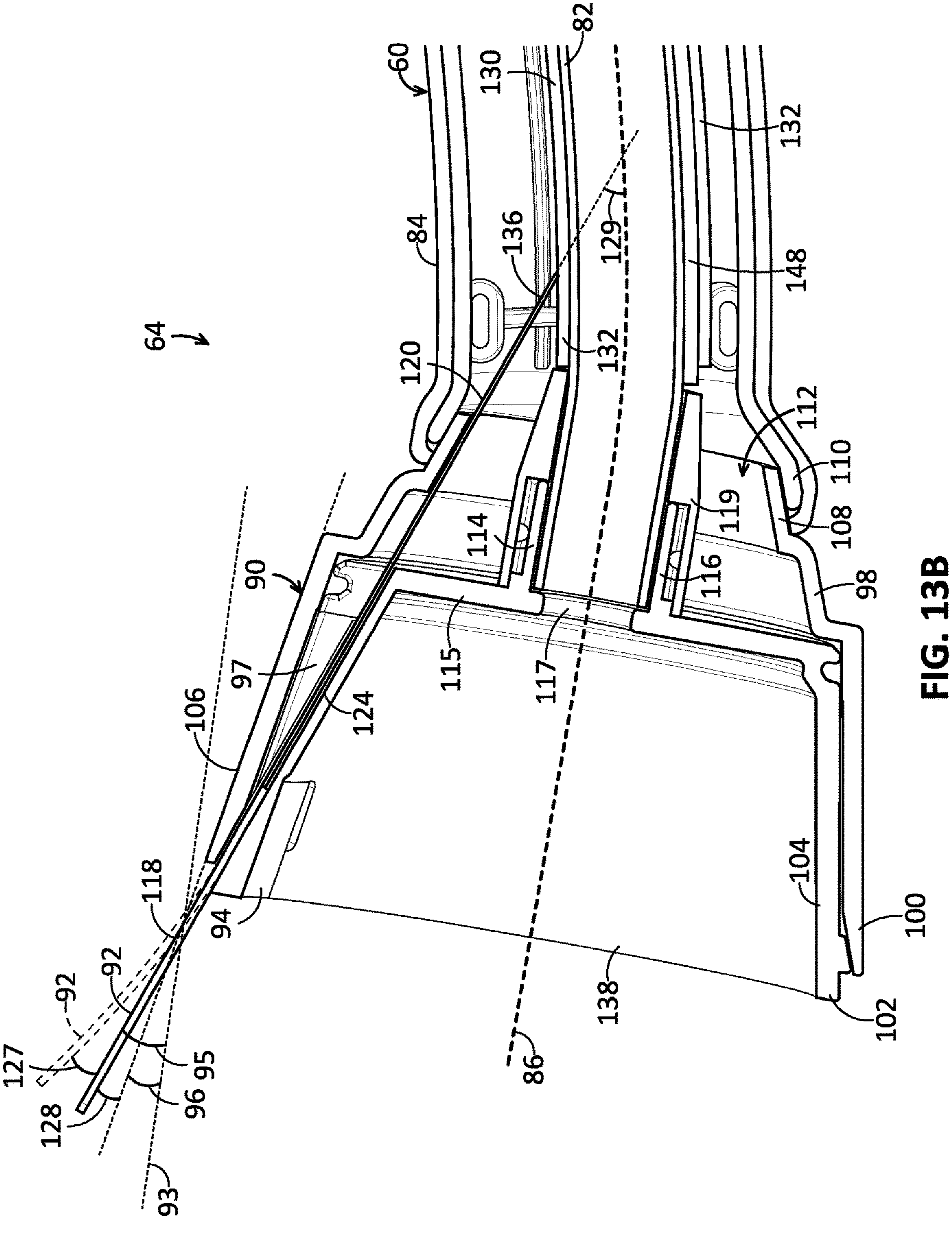
FIG. 13B is a cut-away view of the cutting head of FIG. 13A, particularly showing the cutting element in a deployed position.

Referring further to FIGS. 9A-9C and 10-13B, the colpotomy cup assembly 90 comprises an outer cup 106 and inner cup 104 disposed within the outer cup 106. The inner cup 104 is rotatable relative to outer cup 106 about the longitudinal axis 86 of the shaft assembly 60. Referring specifically to FIGS. 13A and 13B, the inner shaft 82 of the shaft assembly 60 is affixed to the inner cup 104 of the colpotomy cup assembly 90, while the outer shaft 84 of the shaft assembly 60 is affixed to the outer cup 106 of the colpotomy cup assembly 90, such that rotation of the inner shaft 82 relative to the outer shaft 84 of the shaft assembly 60 correspondingly rotates the inner cup 104 within the outer cup 106 of the colpotomy cup assembly 90 about the longitudinal axis 86 of the shaft assembly 60. In the illustrated embodiment, the outer cup 106 at the proximal end 98 of the colpotomy cup assembly 90 forms a reduced-diameter annular lip 108 around which a distal end 110 of the outer shaft 84 of the shaft assembly 60 is affixed, and a proximal opening 112 through which a distal end 114 of the inner shaft 82 of the shaft assembly 60 extends.

The inner cup 104 at the proximal end 98 of the colpotomy cup assembly 90 comprises a transverse wall 115 (shown in FIG. 10) from which a knurled boss 116 (shown best in FIGS. 11A and 11B) proximally extends and in which the distal end 114 of the inner shaft 82 is disposed. The outer diameter of the distal end 114 of the inner shaft 82 is smaller than the inner diameter of the boss 116 of the inner cup 104, and a flexible or pliable sleeve 119 is affixed over (e.g., heat shrunk) the exterior of the boss 116 of the inner cup 104 and the exterior of the distal end 114 of the inner shaft 82, thereby creating a flexible joint between the inner cup 104 and the inner shaft 82 of the shaft assembly 60 at the proximal end 98 of the inner cup 104 of the colpotomy cup assembly 90. In this manner, torque may be transmitted from the inner shaft 82 of the shaft assembly 60 to the inner cup 104 of the colpotomy cup assembly 90 more efficiently when the colpotomy device 14 is bent at the junction between the shaft assembly 60 and the colpotomy cup assembly 90. The inner cup 104 at the proximal end 98 of the colpotomy cup assembly 90 further comprises a through-hole 117 (FIG. 10) formed in the center of the transverse wall 115 through which the rigid shaft 24 of the uterine manipulator 20 extends, such that the colpotomy cup assembly 90 may both be longitudinally and rotationally displaced relative rigid shaft 24 of the uterine manipulator 20.

At least a portion of the cutting element 92 is disposed between the outer cup 106 and the inner cup 104, and is mechanically coupled to the inner cup 104, such that when inner cup 104 is rotated within the outer cup 106 about the longitudinal axis 86, the cutting element 92 rotates with the inner cup 104, thereby circumferentially incising the vaginal-cervical junction J (shown in FIG. 8). Thus, it can be appreciated that, while the colpotomy cup assembly 90 is abutted against the vaginal fornices VF, the outer cup 106 remains stationary relative to the vagina V, while the inner cup 104, along with the cutting element 92, rotates within the inner cup 104 relative to the vagina V. In this regard, the frictional forces applied by the vagina V to the colpotomy cup assembly 90 are not transmitted to the inner cup 104, thereby allowing the inner cup 104 to freely rotate within the outer cup 106 with minimal friction. Notably, the outer cup 106 should have a suitable thickness and be composed of a suitably rigid material, such that concentricity is maintained between the outer cup 106 and inner cup 104.

In the illustrated embodiment, the cutting element 92 is slidably coupled to the inner cup 104 of the colpotomy cup assembly 90, such that the cutting element 92 is configured for being distally advanced from a stored position (where a distal portion 118 of the cutting element 92 resides within the colpotomy cup assembly 90) (see FIG. 13A) to a deployed position (where the distal portion 118 of the cutting element 92 extends distally from the colpotomy cup assembly 90) (see FIG. 13B).

Figure 14A:
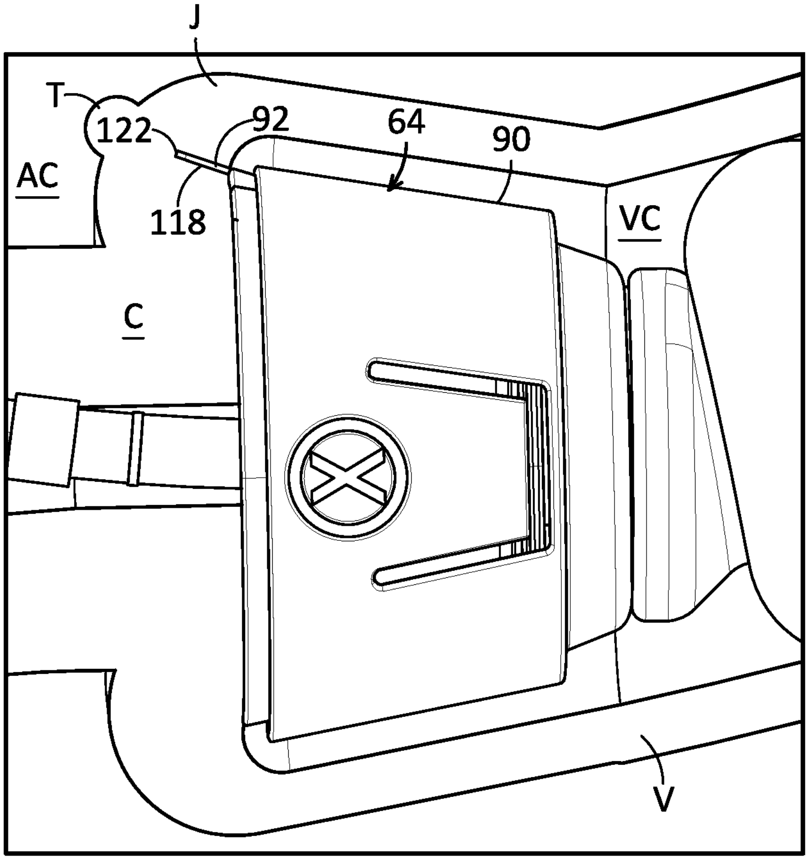
FIG. 14A is a cut-away view of the cutting head of FIG. 8 tenting a vaginal-cervical junction of the patient.
Figure 14B:
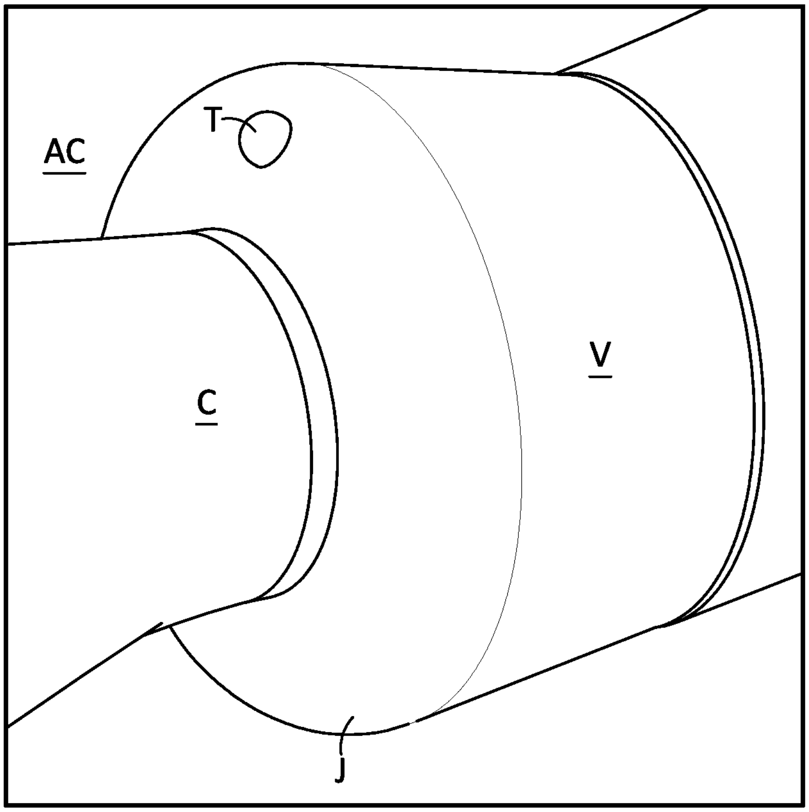
FIG. 14B is a perspective view of the cutting head of FIG. 14A tenting the vaginal-cervical junction of the patient.
Figure 14C:
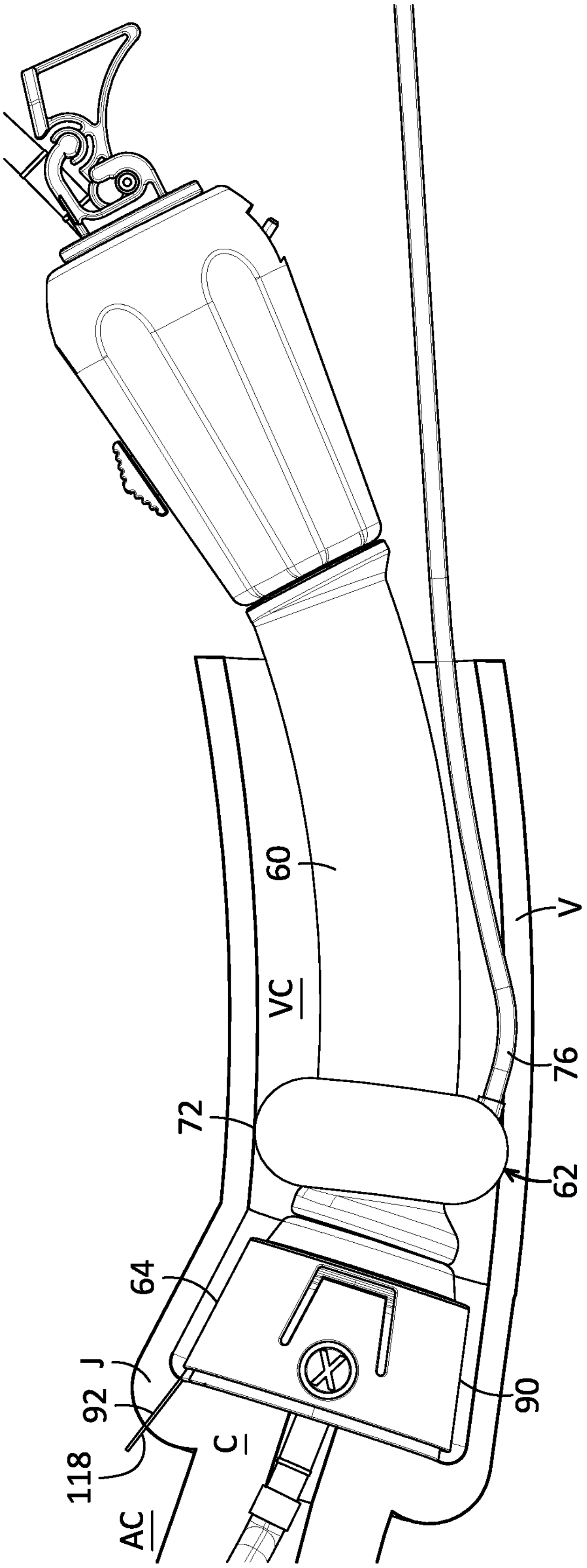
FIG. 14C is a cut-away view of the cutting head of FIG. 8 puncturing through the vaginal-cervical junction of the patient.

In the embodiment illustrated in FIGS. 14A-14C, the distal portion 118 of the cutting element 92 has a blunt tip 122, such that the cutting element 92 is configured for causing the vaginal-cervical junction J to tent T (FIG. 14B) within the abdominal cavity A of the patient P when the blunt tip 122 of the cutting element 92, is translated distally and urged against the vaginal fornices VF (see FIGS. 14A-14B). In this manner, the physician may laparoscopically visualize the tent T and ensure that the cutting element 92 is properly located relative to the cervix C prior to puncturing the vaginal-cervical junction J into the abdominal cavity AC of the patient P with the cutting element 92 (see FIG. 14C).

Referring specifically to FIGS. 11A-11B, 12, and 13A-13B, the inner cup 104 comprises an electrode channel 124 extending along the inner cup 104. The cutting element 92 is slidably disposed within the electrode channel 124, such that the cutting element 92 can be advanced from the stored position (FIGS. 11A and 13A), in which the distal portion 118 of cutting element 92 is disposed between the outer cup 106 and inner cup 104 of the colpotomy cup assembly 90, to the deployed position (FIG. 13B), in which the distal portion 118 is advanced beyond the distal rim 102 of the colpotomy cup assembly 90.

When the cutting element 92 is in the stored position (FIG. 11A), the distal portion 118 of the cutting element 92 does not extend past the distal rim 102 of the colpotomy cup assembly 90, such that the distal portion 118 of the cutting element 92 is completely housed within the electrode channel 124 of the inner cup 104 of the colpotomy cup assembly 90, and when the cutting element 92 is in the deployed position (FIG. 11B), the distal portion 118 of the cutting element 92 extends past the distal rim 102 of the colpotomy cup assembly 90. In either the stored position (FIG. 11A) or the deployed position (FIG. 11B) of the cutting element 92, the electrode channel 124 of the inner cup 104 retains the distal portion 118 of the cutting element 92 while the inner cup 104 rotates within and relative to the outer cup 106 of the colpotomy cup assembly 90, such that the cutting element 92 rotates with the inner cup 104. In the illustrated embodiment, at least a portion of the electrode channel 124 is open, and thus, the cutting head 64 may further comprise a retention plate 126 configured for retaining the cutting element 92 within the electrode channel 124 as the cutting element 92 slides between the stored position and the deployed position.

In the embodiment illustrated in FIGS. 13A and 13B, the electrode channel 124, and thus the distal portion 118 of the cutting element 92, forms an acute angle 95 (e.g., in a range of 20°-65°) with the longitudinal axis 86 or centerline of the colpotomy cup assembly 90 (shown by the parallel line 93 in FIG. 13B). The acute angle 95 helps ensure that the distal portion 118 of the cutting element 92 will puncture the vaginal-cervical junction J when advanced. Without providing the acute angle 95, the inventors found that the cutting element 92 can slide beneath the cervix C without puncturing the target tissue.

The colpotomy cup assembly 90 is conically shaped and flares outward from a proximal end 98 to a distal end 100 of the colpotomy cup assembly 90, thereby forming an acute angle 96 with the longitudinal axis 86 of the shaft assembly 60. The acute angle 96 shown is 10° but could be in the range of 5°-20°. The electrode channel 124, and thus the distal portion 118 of the cutting element 92 when in its stored position, forms an additional acute angle 128 with the exterior profile of the colpotomy cup assembly 90.

In the illustrated embodiment, this is accomplished by thickening a proximal portion of the wall of the inner cup 104 of the colpotomy cup assembly 90 in a circumferential segment 97 adjacent the electrode channel 124. The additional acute angle 128 shown is 10° but may be, e.g., in the range of 5°-20°. Thus, the acute angle 95 formed by the electrode channel 124 (and thus the cutting element 92) with the longitudinal axis 86 of the shaft assembly 60 (the sum of the acute angle 96 formed between the exterior profile 96 of the colpotomy cup assembly 90 and the additional acute angle 128 formed between the electrode channel 124 and the exterior profile of the colpotomy cup assembly 90) may be in a range of 20°-65°. In the illustrated embodiment, the acute angle 95 formed by the electrode channel 124 with the longitudinal axis 86 60 is 20°.

It should be appreciated that, by additionally angling the electrode channel 124, and thus, the distal portion 118 of the cutting element 92, relative to the longitudinal axis 86 of the shaft assembly 60, the exterior conical profile of the colpotomy cup assembly 90 may be reduced. That is, the upper end of the range of the acute angle 96 formed between the exterior profile of the colpotomy cup assembly 90 and the longitudinal axis 86 of the shaft assembly 60 is limited by the ability of the exterior contour of the colpotomy cup assembly 90 to conform to the apex of the vaginal cavity VC of the patient P. Thus, angling the cutting element 92 relative to the exterior contour of the colpotomy cup assembly 90 facilitates puncturing and cutting through the vaginal-cervical junction J, while still being able to maintain reasonable conformance between the exterior contour of the colpotomy cup assembly 90 and the vaginal cavity VC.

Figure 13C:
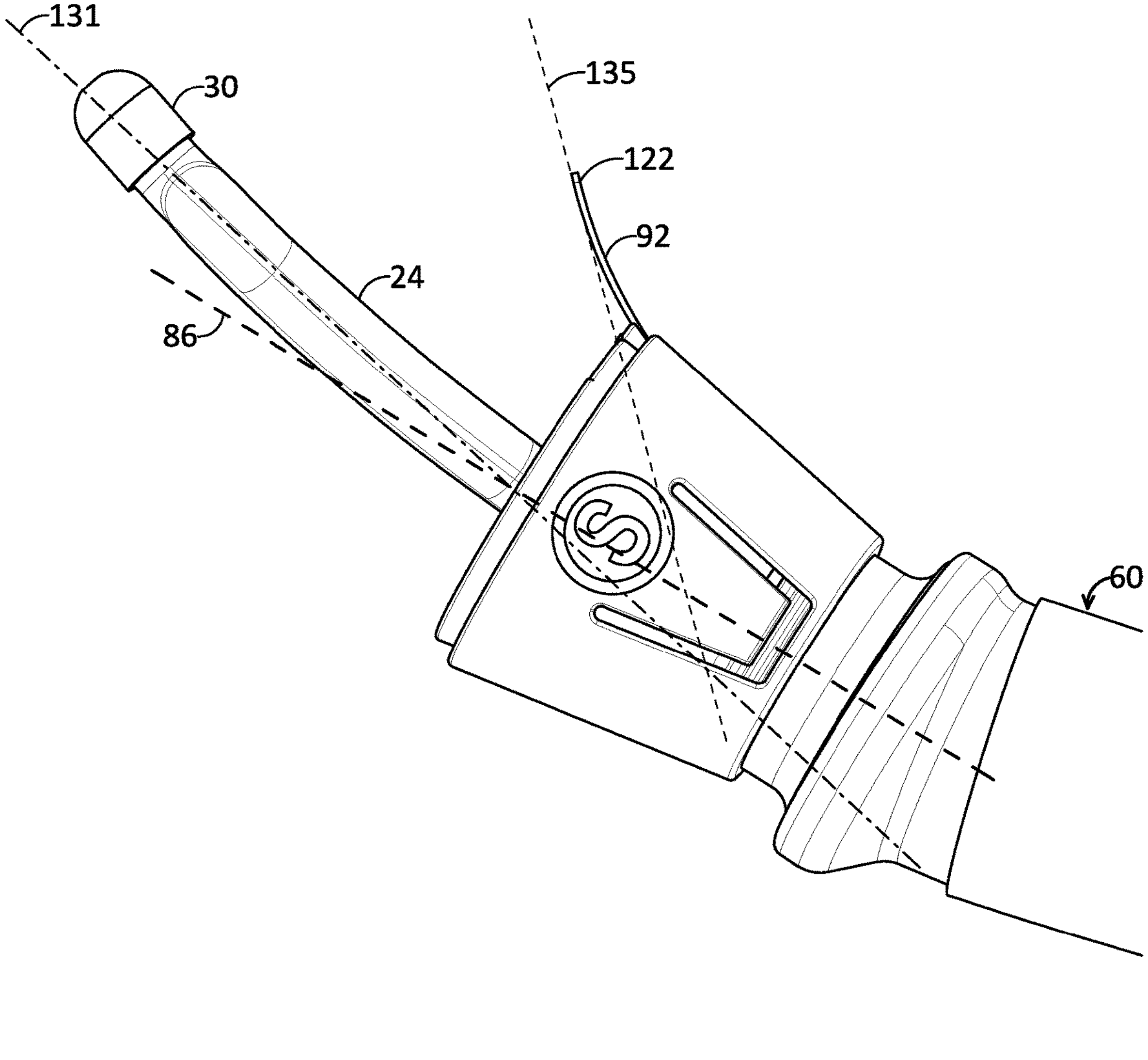
FIG. 13C is a cut-away view of the cutting head of FIG. 13A, particularly showing the longitudinal axes of a uterus, tangent of a distal tip of a cutting element, and shaft assembly.
Figure 13D:
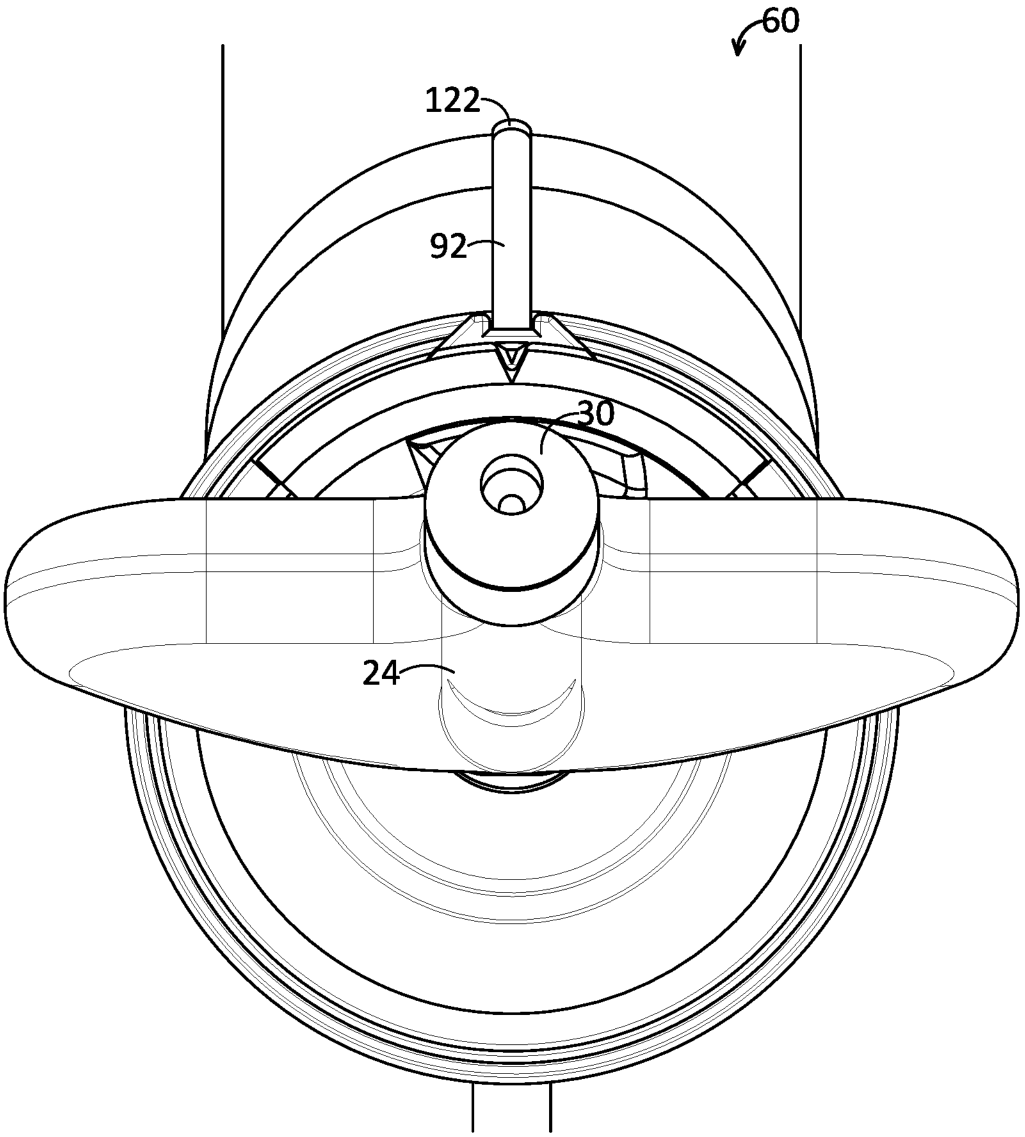
FIG. 13D is a front view of the cutting head of FIG. 13A, particularly showing the cutting element at a 12 o'clock position.

Significantly, it is important that the cutting element 92 does not impinge upon the tissue of the uterus U. In particular, as illustrated in FIGS. 13C and 13D, when the cutting element 92 is located on the inside bend of the curved shaft assembly 60 (e.g., at the 12 o'clock position illustrated in FIG. 13D), the cutting element 92 may intersect with the uterus U (not shown in FIGS. 13C and 13D), which curves upward into the path of the cutting element 92 due to the fact the axis 131 of the uterus U will follow the curvature of the distal end 30 of the rigid shaft 24 of the uterine manipulator 20. As a result, any tenting T of the vaginal-cervical junction J within the abdominal cavity A of the patient P, as illustrated in FIG. 14B, may be difficult to visualize. Furthermore, the bottom surface of the cutting element 92 may make contact with the uterus U and/or cervix C, thereby causing the current density on the surface of the cutting element 92 to decrease when electrical ablation energy is provided to the tissue cutting device 22, and making incision of the tissue at the vaginal-cervical junction J by the cutting element 94 more difficult.

To ensure that the cutting element 92 does not impinge on the tissue of the uterus U, in an alternative embodiment, the distal end 118 of the cutting element 92 may be pre-curved, such that a radially outward curvature 127 (shown in phantom in FIG. 13B) is imparted on the cutting element 92 as it is advanced out of the electrode channel 124. The radially outward curvature 127 of the cutting element 92 may form a further additional acute angle 133 between a tangent 135 at the blunt tip 122 of the cutting element 92 and the electrode channel 124 of 20°, but may be, e.g., in the range of 5°-30°. Thus, the acute angle 133 formed between the tangent 135 at the blunt tip 122 of the cutting element 92 and the longitudinal axis 86 of the shaft assembly 60 may be in the range of 20°-65°. In the illustrated embodiment, the acute angle 133 formed between the tangent 135 at the blunt tip 122 of the cutting element 92 and the longitudinal axis 86 of the shaft assembly 60 is 40°.

Figure 11A:
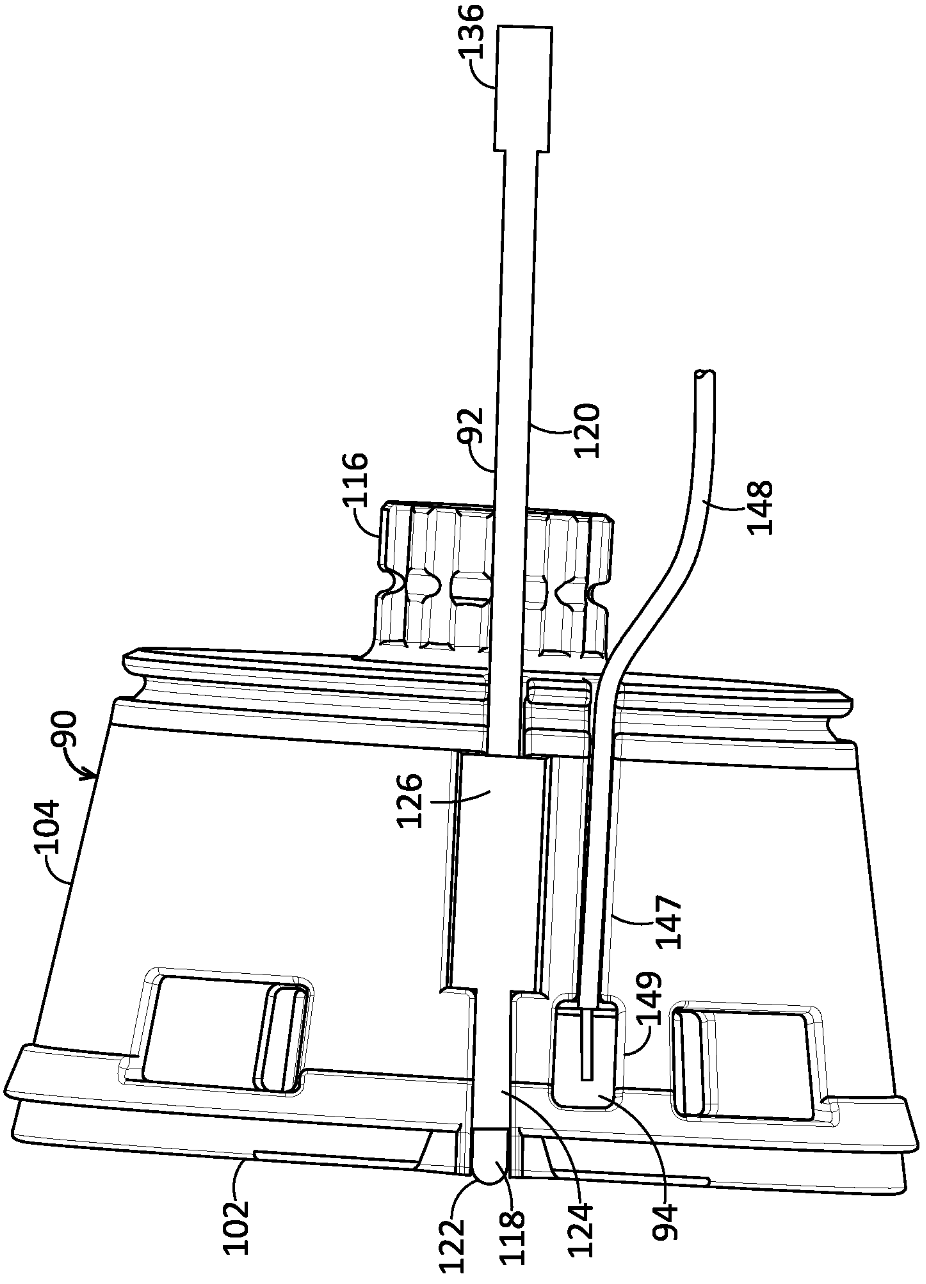
FIG. 11A is a profile view of an inner cup of a colpotomy cup assembly of the cutting head of FIG. 8, particularly showing a cutting element in a stored position.
Figure 11B:
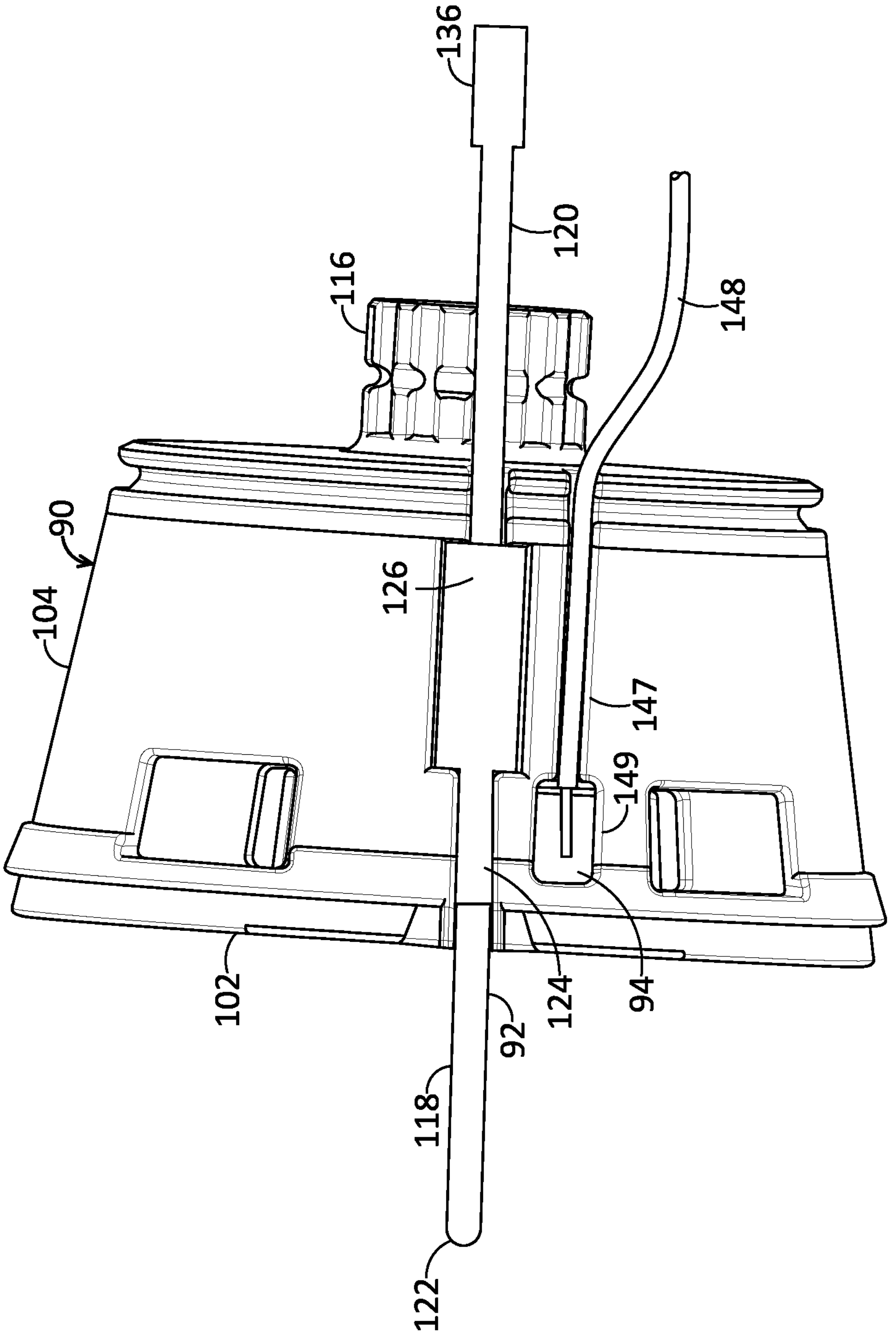
FIG. 11B is a profile view of the inner cup of FIG. 11A, particularly showing the cutting element in a deployed position.
Figure 12:
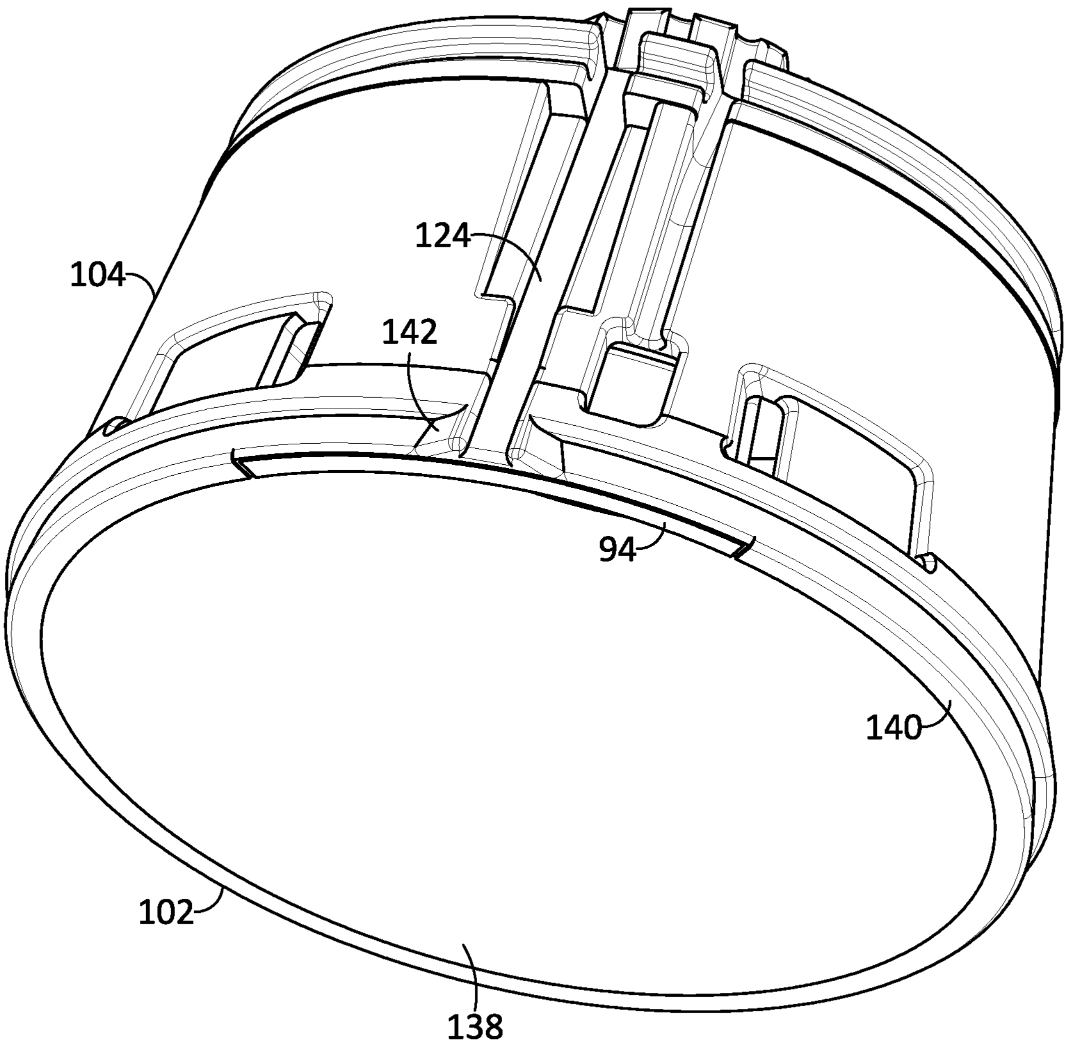
FIG. 12 is a perspective view of the inner cup of the colpotomy cup assembly of FIG. 11A.

Referring to FIGS. 13A-13B, 15A-15B, and 17-19, in one embodiment, alternating deployment of the cutting element 92 from the colpotomy cup assembly 90 and retraction of the cutting element 92 within the colpotomy cup assembly 90 may use a slidable electrode sleeve 130 slidably disposed relative to the shaft assembly 60 (in comparison with a less preferable option of routing the cutting element 92 back through a lumen in the wall of the shaft assembly 60 to the handle assembly 56) and extends between the handle assembly 66 and the colpotomy cup assembly 90. The slidable electrode sleeve 130 has a distal end 132 coupled to the proximal portion 120 of the cutting element 92 and a proximal end 134 operatively associated with the handle assembly 56. As best illustrated in FIGS. 11A and 11B, the proximal portion 120 of the cutting element 92 may have an enlarged tab 136, such that the cutting element 92 may be more securely affixed to the distal end 132 of the slidable electrode sleeve 130 (i.e., the additional surface area provided by the enlarged tab 136 allows the proximal portion 120 of the cutting element 92 to be more efficiently anchored to the distal end 132 of the electrode sleeve 130 (shown in FIGS. 13A-13B).

Figure 15A:
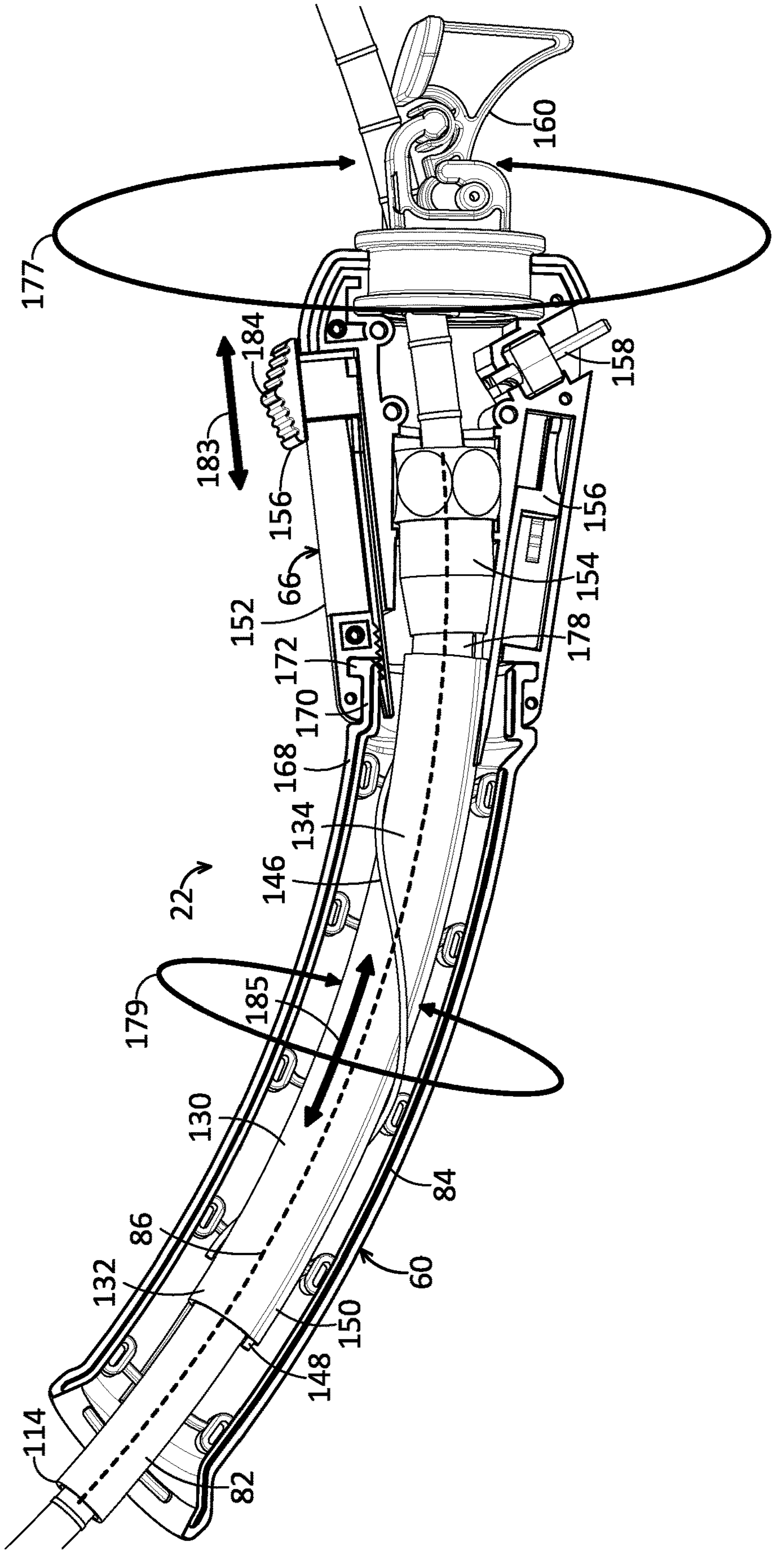
FIG. 15A is a cut-away view of a shaft assembly and handle assembly of the tissue cutting device of FIG. 6, particularly showing a deployment mechanism of the handle assembly in a retracted position.
Figure 15B:
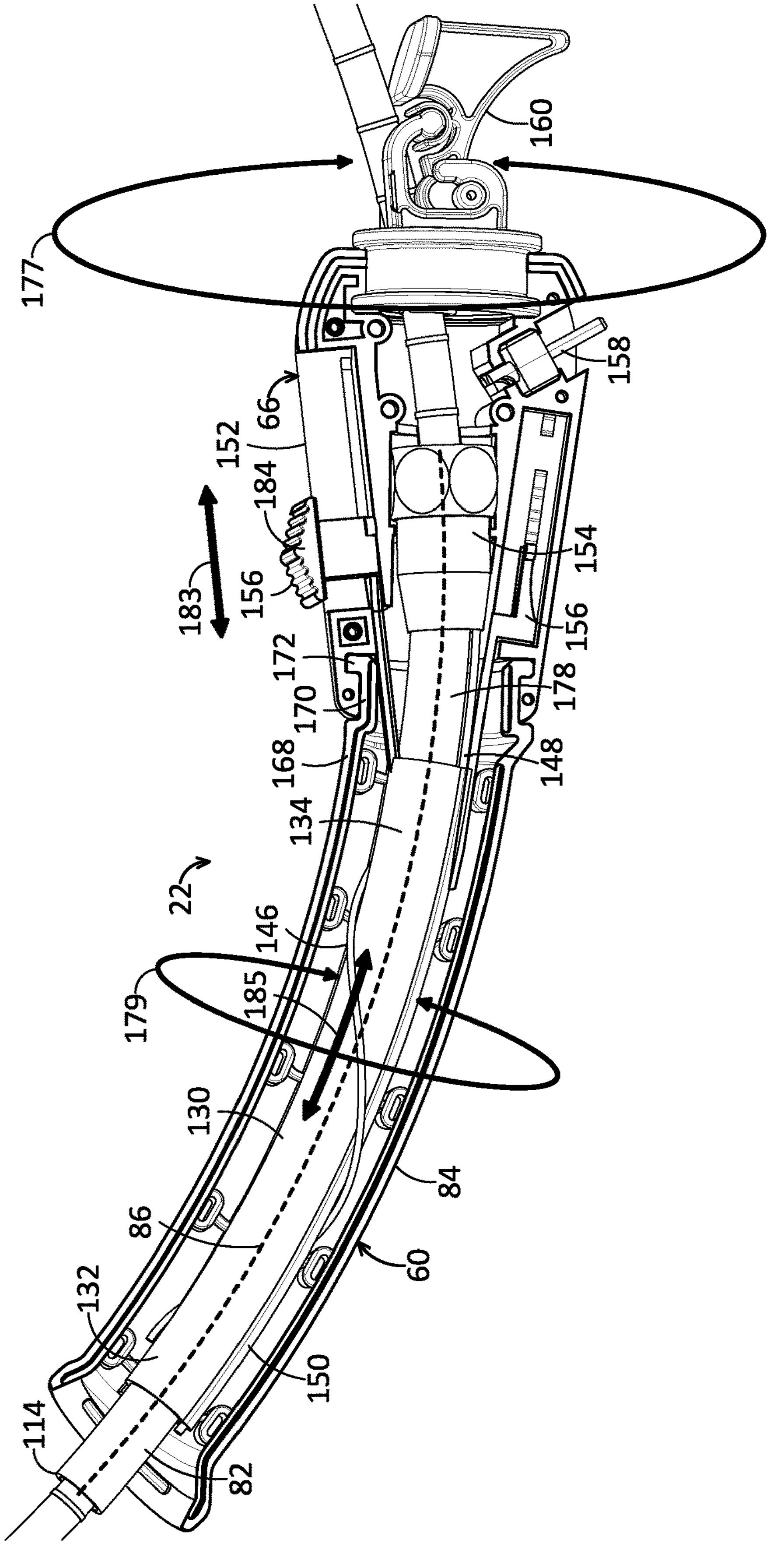
FIG. 15B is a cut-away view of the shaft assembly and handle assembly of FIG. 15A, particularly showing a deployment mechanism of the handle assembly in an advanced position.

In the illustrated embodiment, the slidable electrode sleeve 130 is slidably disposed over the inner shaft 82 of the shaft assembly 60, such that it is coaxially disposed between and slidable relative to both the inner shaft 82 and the outer shaft 84 of the shaft assembly 60. Thus, as illustrated in FIG. 15B, when the slidable electrode sleeve 130 is advanced distally relative to the inner shaft 82 parallel the longitudinal axis 86 of the shaft assembly 60, the cutting element 92 transitions from its stored position (FIG. 11A) within the electrode channel 124 of the inner cup 104 to the deployed position (FIG. 11B). Conversely, as illustrated in FIG. 15A, when the slidable electrode sleeve 130 slides proximally relative to the inner shaft 82 parallel to the longitudinal axis 86 of the shaft assembly 60, the cutting element 92 is retracted from its deployed position (FIG. 11B) back into the electrode channel 124 of the inner cup 104 to its stored position (FIG. 11A). Although the distal portion 118 of the cutting element 92 is shown partially exposed in its stored position in FIG. 11A, in an alternative embodiment, the distal portion 118 of the cutting element 92 can be further retracted within the electrode channel 124, such that it is completed covered by the inner cup 104 and outer cup 106.

Notably, the deployed cutting element 92 must be stiff enough to puncture the vaginal-cervical junction J of the patient (see FIG. 8) and to circumferentially incise the tissue at the vaginal-cervical junction J without mechanically buckling. However, as can be appreciated in FIG. 13A, due to the total angular profile of the cutting element 92 relative to the longitudinal axis 86 of the shaft assembly 60 (i.e., the summation of the acute angle 96 of the colpotomy cup assembly 90 relative to the longitudinal axis 86 of the shaft assembly 60 and the acute angle 128 of the cutting element 92 relative to the exterior profile of the colpotomy cup assembly 90), the cutting element 92 must traverse an angle 129 equal to the total angular profile between the longitudinal axis 86 of the shaft assembly 60 and the electrode channel 124 of the inner cup 104 of the colpotomy cup assembly 90. It is to be understood that stiffness refers to the bending characteristics of cutting element 92.

In the illustrated embodiment, the distal portion 118 has a stiffness greater than the stiffness of the proximal portion 120 of the cutting element 92. Portions of the cutting element 92 that are more resistant to bending are considered to be stiffer, or have a greater stiffness, than regions of a flexure that bend more easily.

Figure 16:
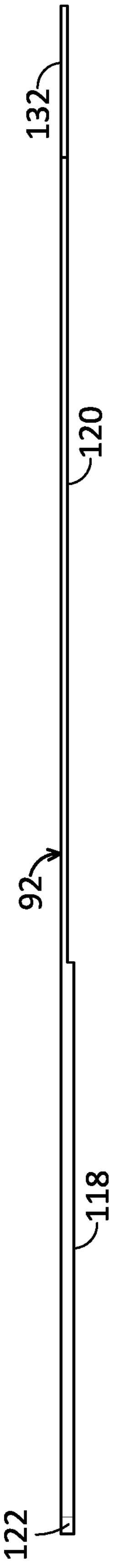
FIG. 16 is a profile view of the cutting element of the cutting head of FIGS. 9A-9C.
Figure 17:
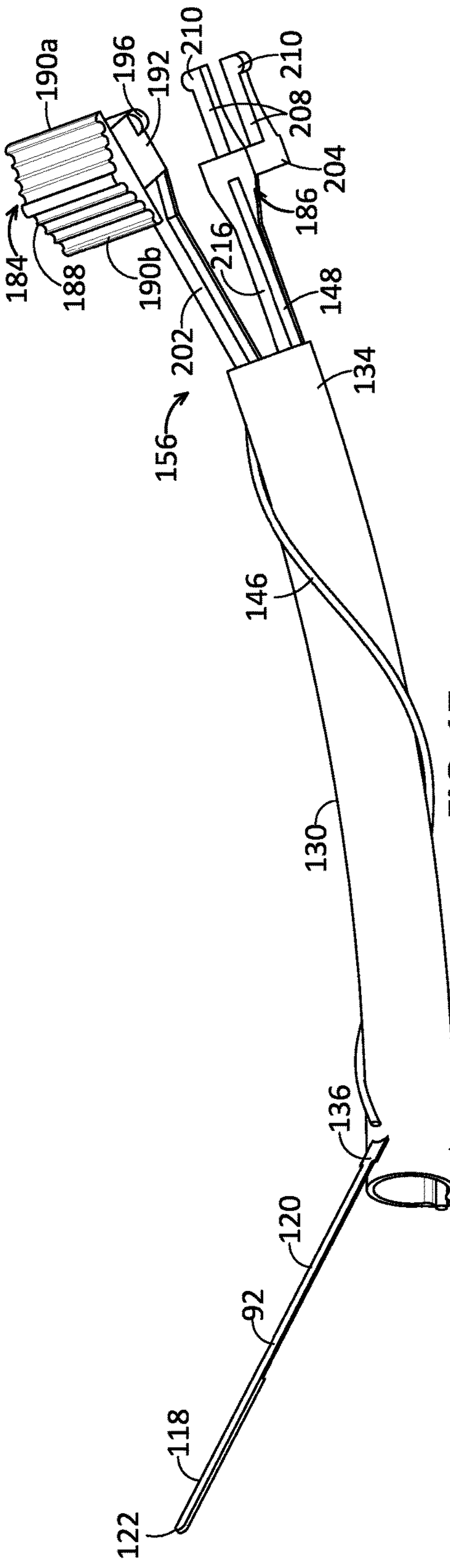
FIG. 17 is a top perspective view of a slidable electrode sleeve and deployment mechanical deployment actuator used in the tissue cutting device of FIG. 6.

In one illustrated embodiment, the cutting element 92 is monolithic, in which case, the distal portion 118 of the cutting element 92 may have a geometric profile that is greater than the geometric profile of the proximal portion 120 of the cutting element 92 in the radial direction (i.e., the thickness of the cutting element 92), as illustrated in FIGS. 13A-13B and 16. It is appreciated that several properties of cutting element construction can be controlled to adjust stiffness and create a cutting element with two or more portions, each having a different stiffnesses. For example, selected manufacturing processes can be used to alter a material's modulus of elasticity. The manufacturing processes can be used selectively on different areas of a flexure to create a flexure with different moduli of elasticity in different areas of the flexure. In another example, a flexure may be constructed of multiple materials, each material having a different modulus of elasticity.

Preferably, the length of the more stiff distal portion 118 of the cutting element 92 is greater than the entire range between the stored position (FIGS. 11A and 13A) and deployment position (FIGS. 11B and 13B) of the cutting element 92, whereby at least some of the distal portion 118 always remains in the electrode channel 124 of the inner cup 104 of the colpotomy cup assembly 90 (and in this case, within the electrode channel 124 of the inner cup 104 of the colpotomy cup assembly 90), and none of the distal portion 118 resides proximal to the electrode channel 124 of the inner cup 104 of the colpotomy cup assembly 90).

Figure 9A:
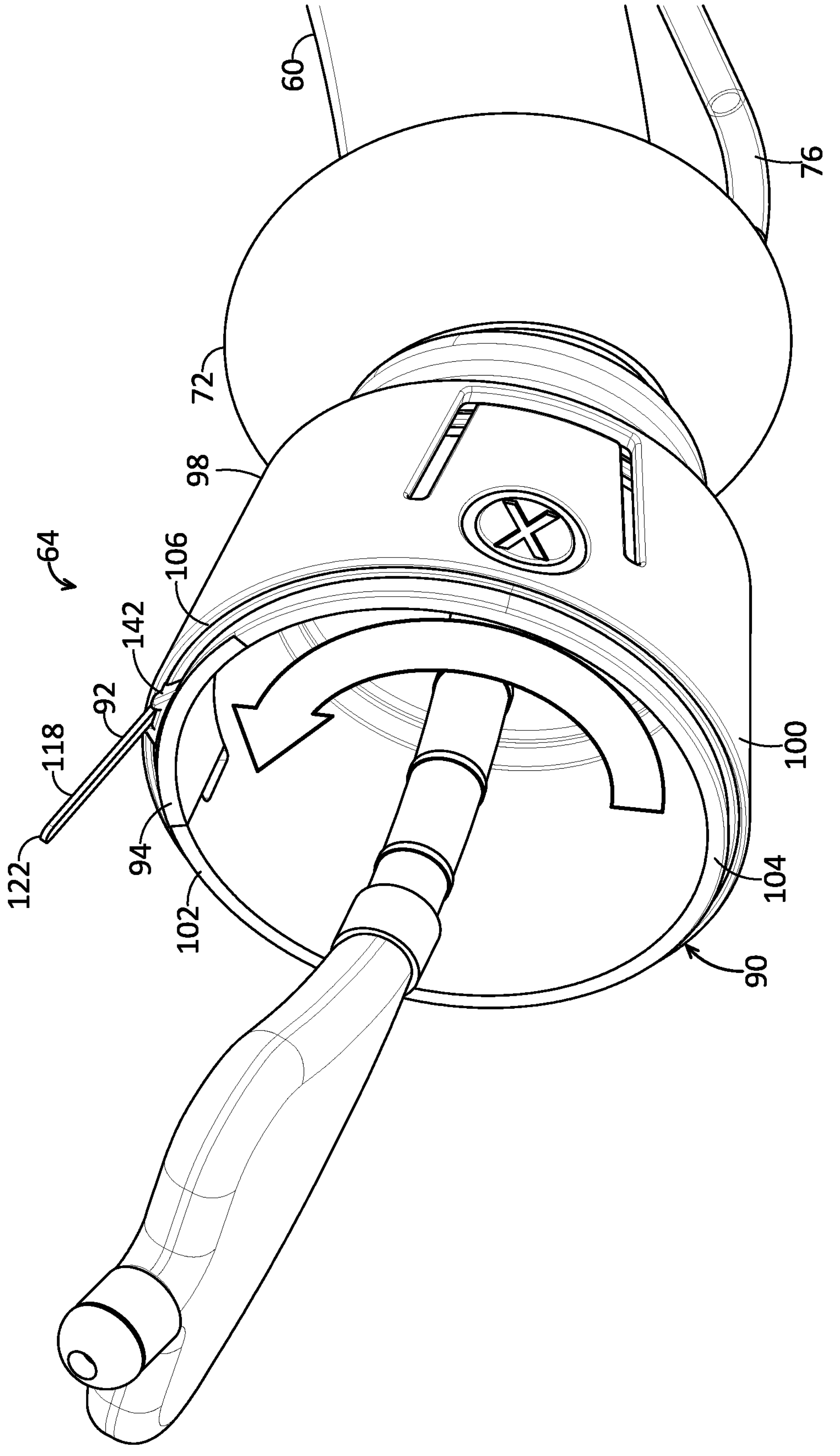
FIG. 9A is a front perspective view of the cutting head of FIG. 8 in one rotational configuration.
Figure 9B:
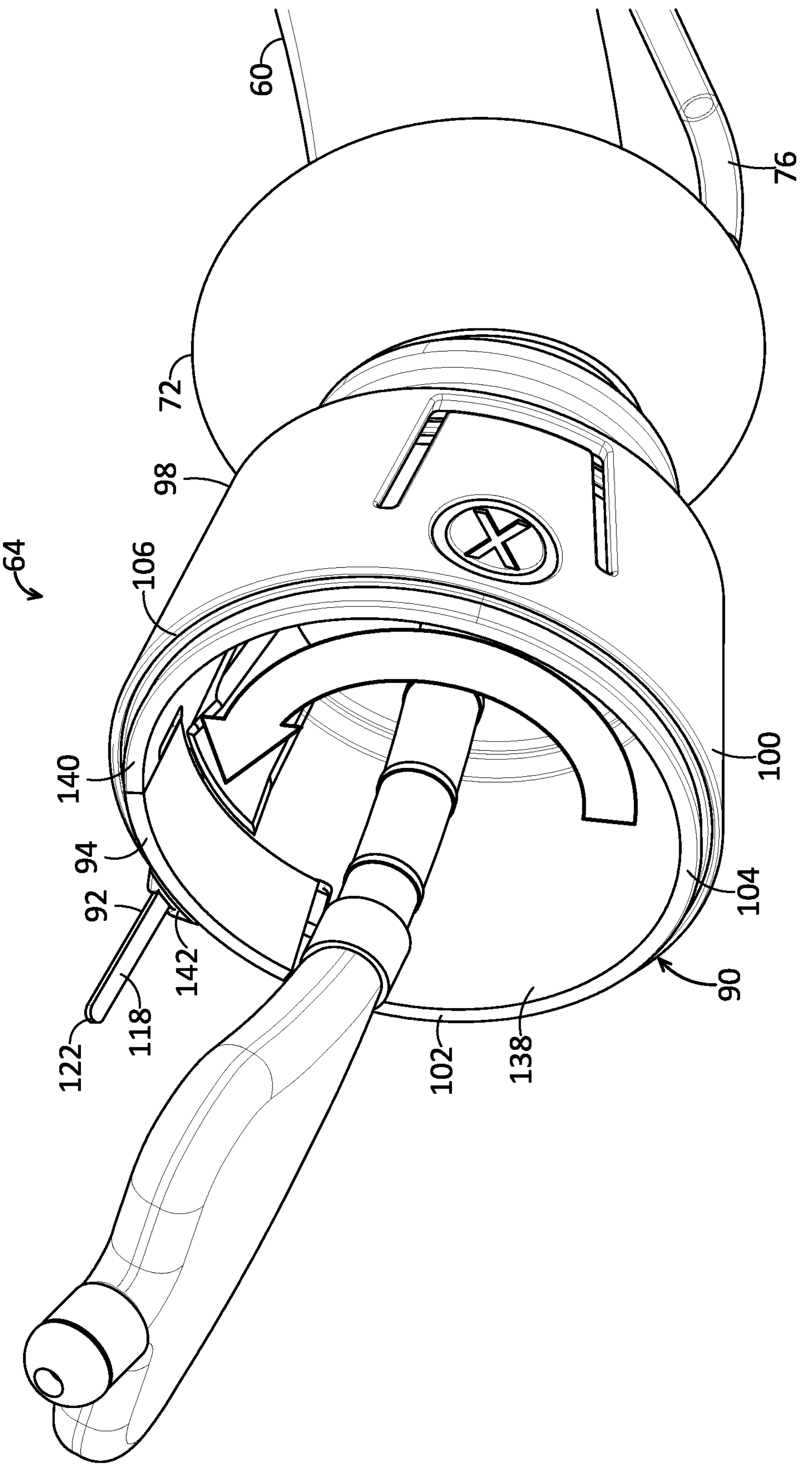
FIG. 9B is a front perspective view of the cutting head of FIG. 8 in another rotational configuration.
Figure 9C:
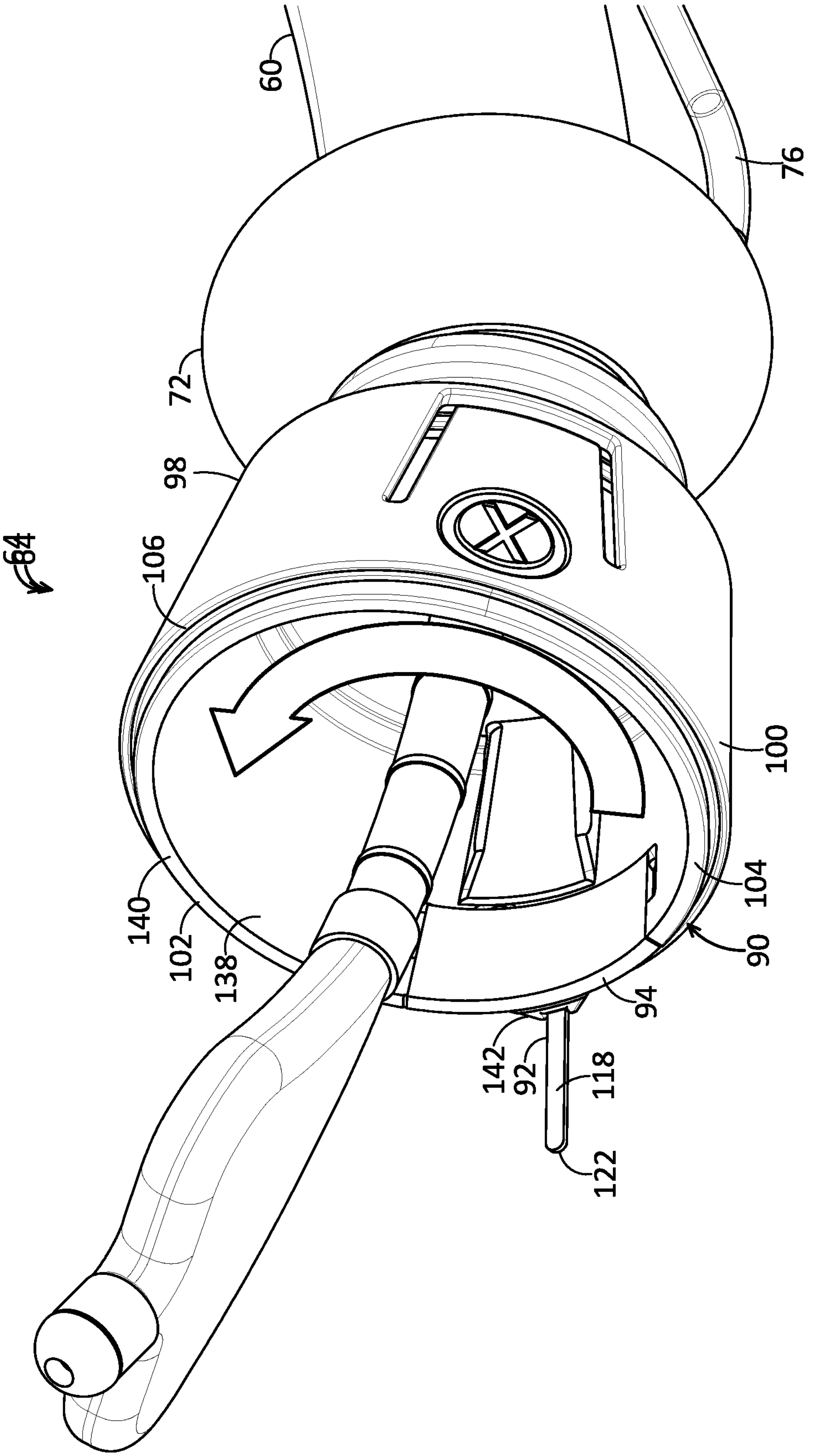
FIG. 9C is a front perspective view of the cutting head of FIG. 8 in still another rotational configuration.
Figure 10:
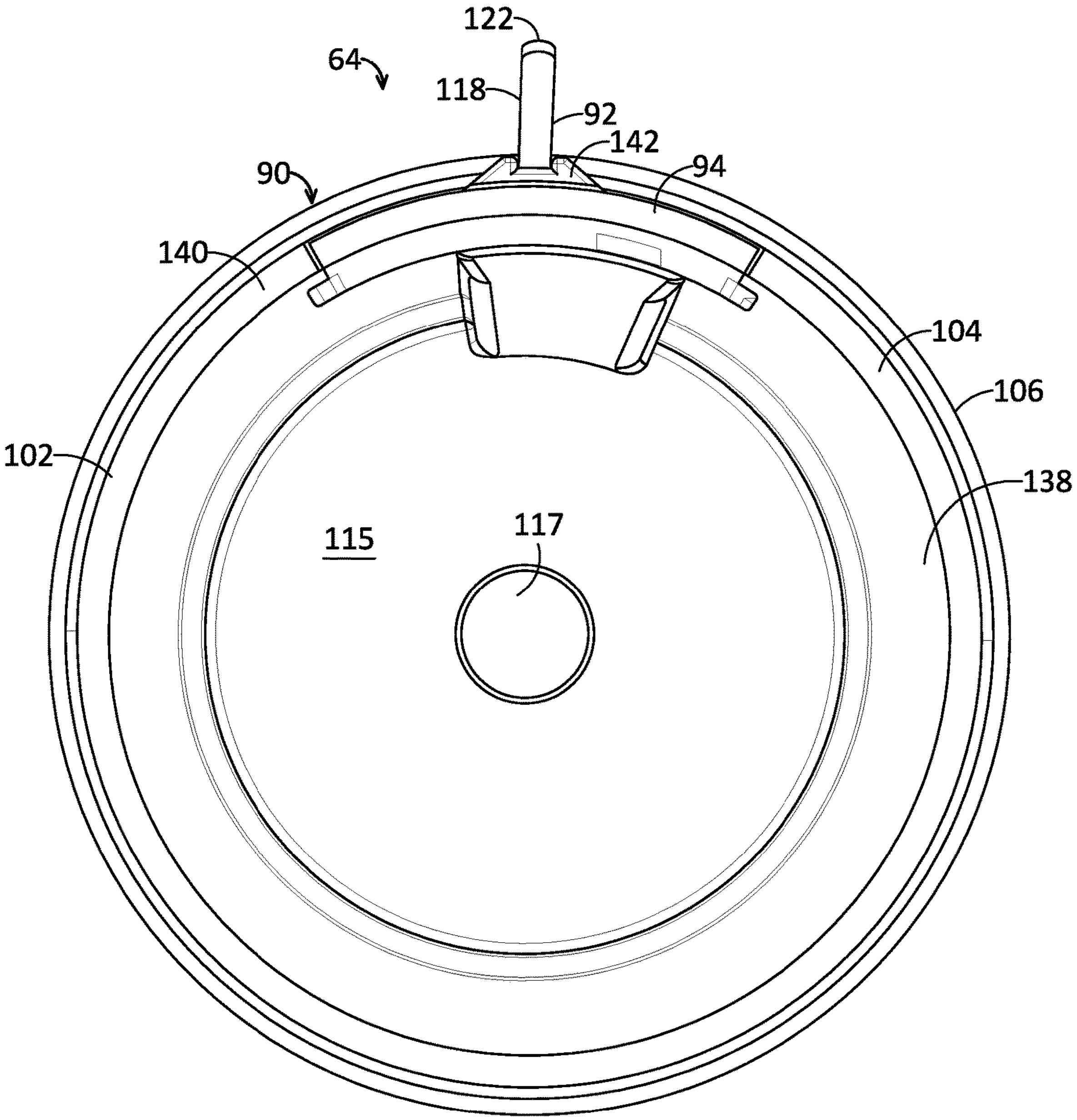
FIG. 10 is a front view of the cutting head of FIG. 8.

As best illustrated in FIGS. 9A-9C, 10, and 13A-13B, the ground electrode 94 is a surface electrode disposed on an inner surface 138 of the inner cup 104 and extends to a distal-facing surface 140 of the inner cup 104 adjacent to the cutting element 92. As shown in FIG. 9B, the ground electrode 94 wraps from the inner surface 138 radially outward along the distal-facing surface 140 of the inner cup 104. In this manner, the portion of the ground electrode 94 located on the distal-facing surface 140 ensures physical contact with the vaginal fornices VF even if the portion of the ground electrode 98 located on the inner surface 140 is not in physical contact with the cervix C (as best shown in FIG. 8), such as when the inner diameter of the inner cup 104 exceeds the outer diameter of the cervix C.

Figure 20:
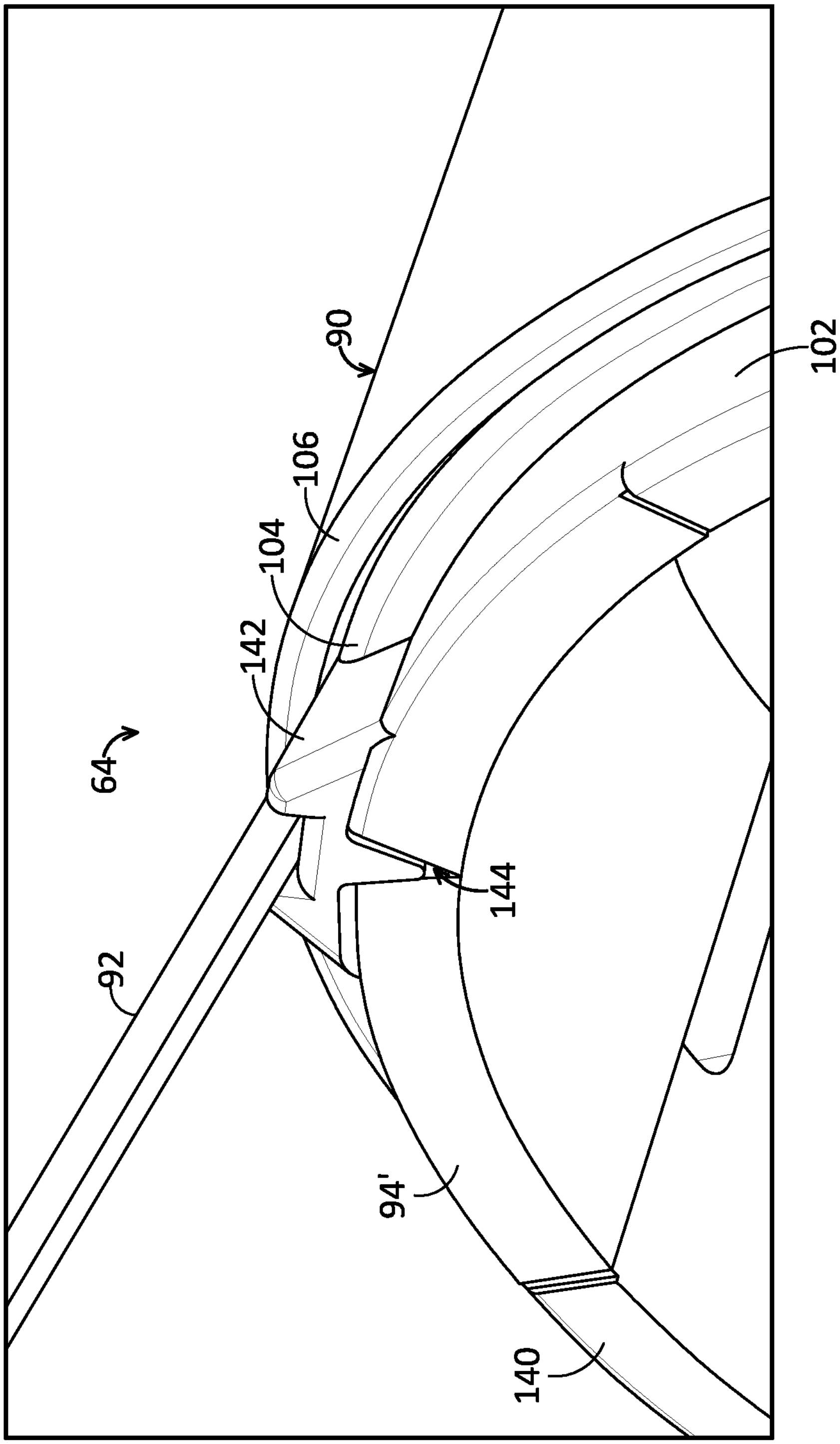
FIG. 20 is a close-up cut-way view of the cutting head of FIG. 6.

In the illustrated embodiment (best shown in FIG. 12), the distal rim 102 of the colpotomy cup assembly 90 is formed by a reduced-diameter annular boss distally extending from the inner cup 104, with the distal-facing surface 140 of the colpotomy cup assembly 90 being the distal-facing surface of the annular boss. In the illustrated embodiment, the inner cup 104 of the colpotomy cup assembly 90 further comprises a raised electrode platform 142 located on the reduced-diameter distal rim 102 of the colpotomy cup assembly 90 at an exit point of the electrode channel 124. The raised electrode platform 142 is electrically insulative and provides a ramped support surface on which the distal portion 118 of the cutting element 92 rides. Thus, the raised electrode platform 142 is configured for maintaining a minimum radial distance between the distal portion 118 of cutting element 92 and the ground electrode 94 (and in particular, the portion of the ground electrode 94 disposed on the distal-facing surface 140 of the inner cup 104 of the colpotomy cup assembly 90) to minimize or prevent shorting or arcing of the electrical energy between the cutting element 92 and the ground electrode 94, which may be otherwise caused by the combination of the high voltage of the electrical energy and the presence of an electrolyte on the surface of the colpotomy cup assembly 90. Thus, when the cutting element 92 exits the electrode channel 124 during deployment from the colpotomy cup assembly 90, the cutting element 92 slides along the top surface of the electrode platform 142 maintaining the minimum radial distance from the ground electrode 94. An alternative embodiment of a ground electrode 94' illustrated in FIG. 20 has a cleaved region 144 on the distal-facing surface 140 of the reduced-diameter distal rim 102. The cleaved region 144 of the ground electrode 94 is circumferentially aligned with the raised electrode platform 142, and thus the deployed cutting element 92. The cleaved region 144 is designed to minimize or prevent arcing of electrical energy between the deployed cutting element 92 and the ground electrode 94. To further minimize arcing of the electrical energy between the cutting element 92 and the ground electrode 94, the colpotomy cup assembly 90 may be composed of an arc resistant material, such as, e.g., acrylic poly(methyl methacrylate) (PMMA).

The cutting device may be any known cutting device, including, but not limited to, a cautery blade, cryoablation cutting element, laser cutting element, ultrasound cutting element, etc. As briefly discussed above, the cutting element 92, in the exemplary embodiment, is an ablation electrode in a bipolar energy delivery with the ground electrode 94. In alternative embodiments, monopolar electrical energy is delivered to the cutting element, in which case, a ground electrode will not be located on the colpotomy cup assembly, but rather will take the form of a patch electrode that can be affixed to the exterior of the patient P.

Referring to FIGS. 15A-15B and 17-19, the colpotomy device 16 further comprises a first electrical wire 146 electrically coupled to the enlarged tab 136 of the cutting element 92 at the distal end 132 of the slidable electrode sleeve 130, and a second electrical wire 148 electrically coupled to the ground electrode 98. As best illustrated in FIGS. 11A-11B, the outer surface of the inner cup 102 of the colpotomy cup assembly 90 includes a wire channel 147 in which the second electrical wire 148 is disposed, and a window 149 through which the ground electrode 98 is exposed for connecting the ground electrode 98. The first and second electrical wires 146, 148 extend from the respective cutting element 92 and ground electrode 98 proximally back to the handle assembly 66 through the shaft assembly 60. In particular, the first electrical wire 146 is attached to the external surface of the slidable electrode sleeve 130, such that the first electrical wire 146 axially translates with the slidable electrode sleeve 130 relative to the shaft assembly 60 to alternately deploy and retract the cutting element 92. In this manner, the cutting element 92, first electrical wire 146, and electrode sleeve 130 axially translate and reciprocate as a single unit.

Figure 18:
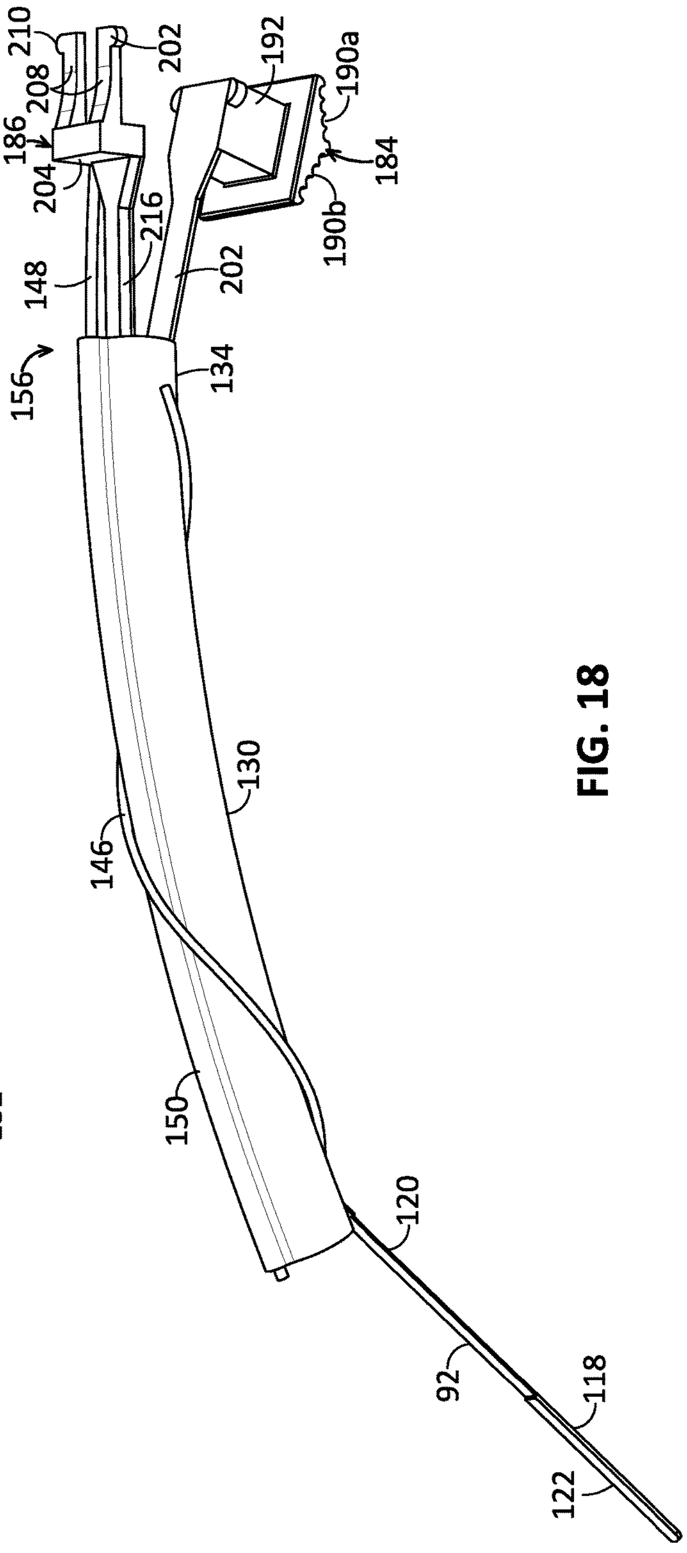
FIG. 18 is a bottom perspective view of the slidable electrode sleeve and deployment mechanical deployment actuator of FIG. 17.
Figure 19:
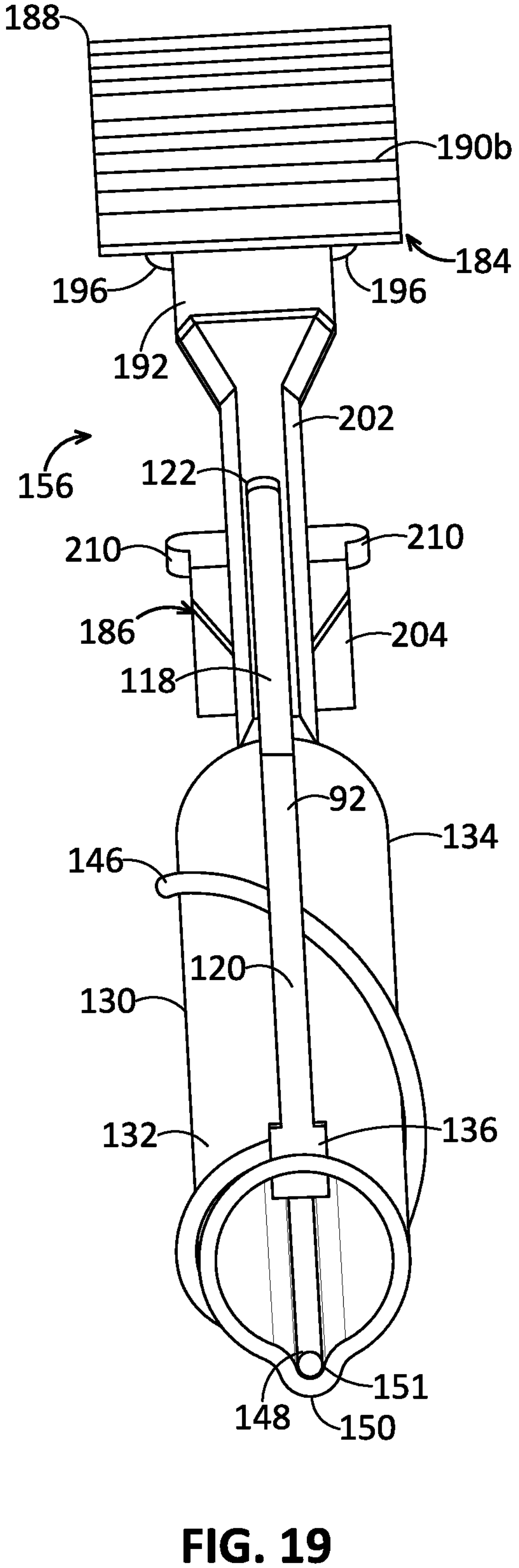
FIG. 19 is a front perspective view of the slidable electrode sleeve and deployment mechanical deployment actuator of FIG. 17.

The second electrode wire 148 rotates with the ground electrode 98 but, unlike the first electrical wire 146, the ground electrode 98 does not axially translate and reciprocate with the cutting element 92, the second electrical wire 148 need not be fixed to the slidable electrode sleeve 130 and may simply be disposed in a longitudinal channel 151 defined by a longitudinal rib portion 150 (best shown in FIGS. 18 and 19). The longitudinal rib portion 150 is formed by a raised portion of the wall of the slidable electrode sleeve 130 that extends along the length of the slidable electrode sleeve 130. In the exemplary embodiment, the second electrical wire 148 is slidably disposed within the longitudinal channel 151 (shown best in FIG. 19), such that the electrode sleeve 130 can slide axially relative to the second electrical wire 148, as best viewed in FIGS. 13A-13B.

It should be noted that rotating handle body 152 about the longitudinal axis 86 may cause the exposed portion of the cutting element 92 to shrink or grow as the cutting element 92 moves circumferentially around the colpotomy cup assembly. That is, since the longitudinal axis 86 is curved, the cutting element 92 has a shorter path to travel when on the inside of the curve and a longer path to travel when on the outside of the curve, causing the exposed portion of the cutting element 92 to appear to be growing or shrinking. In order to prevent or minimize the tendency of the cutting element 92 to shrink or grow as it moves about the longitudinal axis 86, the proximal affixation point of the first electrical wire 146 is not circumferentially aligned with the distal affixation point of the second electrical wire 146. As the proximal and distal affixation points of the first electrical wire 146 become more circumferentially misaligned, the cutting element 92 will be displaced a smaller distance relative to the colpotomy cup assembly 90 in response to bending the shaft assembly 60 along with the first electrical wire 146. In one embodiment, the proximal and distal affixation points of the first electrical wire 146 are circumferentially misaligned in a range of 160°-200°, although it is preferred that the proximal and distal affixation points of the first electrical wire 146 are circumferentially misaligned by 180°. It should be appreciated that the first electrical wire 146 may be spiraled around the slidable electrode sleeve 130, as long as the first and second affixation points of the first electrical wire 146 are circumferentially misaligned. In the exemplary embodiment, the first electrical wire 146 is spiraled 540°, such that the proximal and distal affixation points of the first electrical wire 146 are thus circumferentially misaligned by 540°.

Referring to FIGS. 6, 15A-15B, and 21, the handle assembly 66, not only provides the physician with the means of grasping the tissue cutting device 22, the handle assembly 66 also provides the physician the means for locking the cutting head 64 relative to the uterine manipulator 20, controlling the deployment/retraction of the cutting element 92, controlling the rotating of the cutting element 92, and enabling the tissue cutting device 22 with electrical ablation energy. In particular, the handle assembly 66 comprises a handle body 152, a rotational assembly 154, a mechanical deployment actuator 156, an electrical ablation port 158, and a uterine manipulator locking assembly 160.

The handle body 66 is preferably shaped to be ergonomic for the physician from both a laparoscopic position and from a standing position or sitting position between the legs of the patient P. Alternatively, the handle body 66 may be shaped to be ergonomic for the physician from a standing position on the side of the patient. In the example embodiment, the handle body 66 is hollow and comprises two halves that are affixed to each other in a clam-shell arrangement, although in alternative embodiments, the handle body 66 may be molded as a single piece. The handle body 66 comprises a distal opening 162 in which the proximal end 70 of the shaft assembly 60 is disposed for affixation to the handle body 66.

Figure 21A:
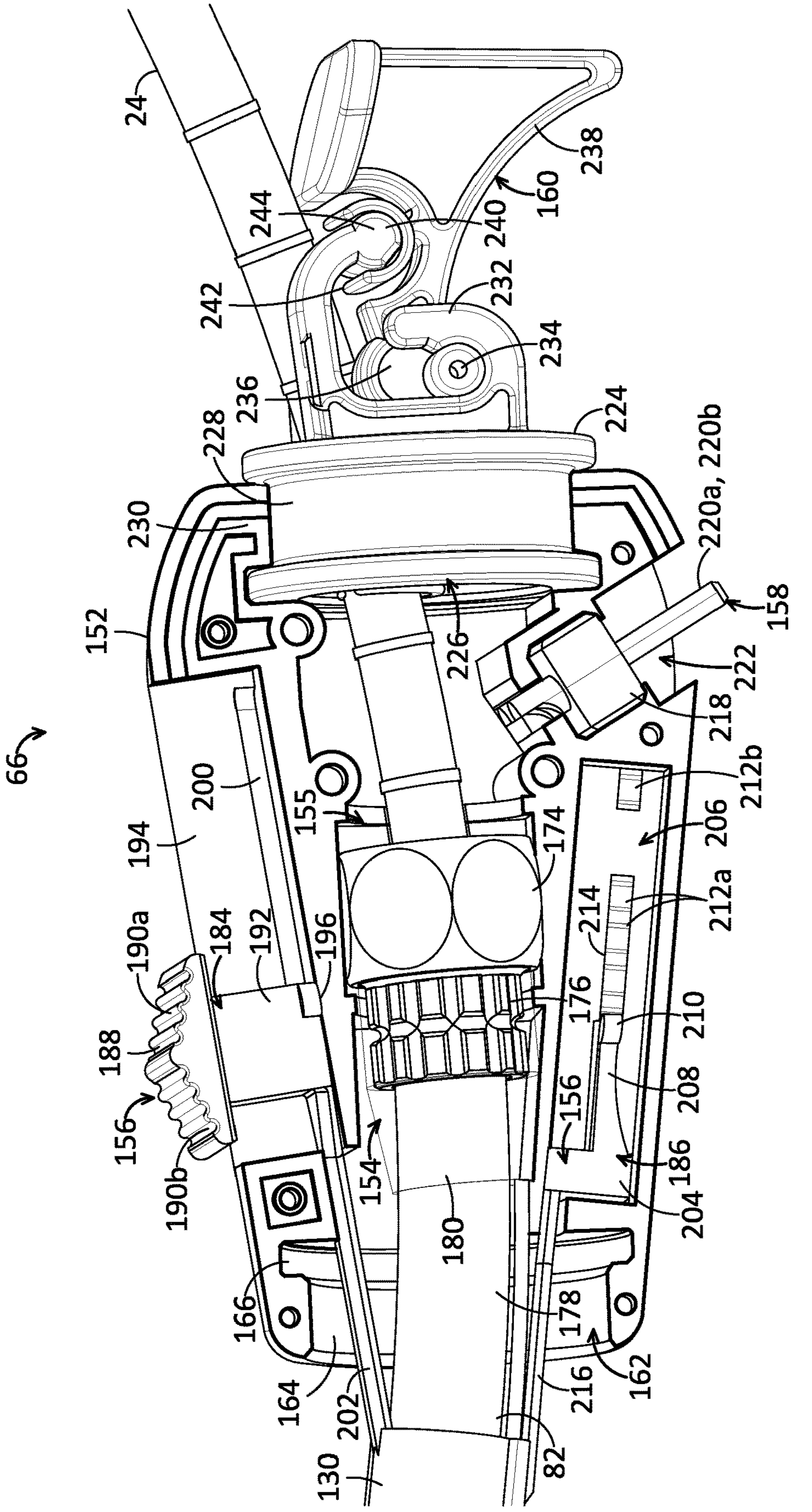
FIG. 21A is a cut-away view of a handle assembly of the tissue cutting device of FIG. 6, particularly showing the handle body of the handle assembly in one rotational orientation.

In particular, the handle body 66 may be rotated relative to the outer shaft 84 of the shaft assembly 60. Furthermore, the handle body 66 rotates relative to the rigid shaft 24 of the uterine manipulator 20. As shown in FIG. 21A, the distal opening 162 comprises a reduced-diameter cavity 164 and an increased-diameter annular space 166 that is coaxial with the reduced-diameter cavity 164. As illustrated in FIGS. 15A and 15B, the outer shaft 84 of the shaft assembly 60 has a proximal end 168 that comprises a reduced-diameter annular depression 170 and an annular lip 172 that respectively conform to the reduced-diameter cavity 164 and increased-diameter annular space 166, as illustrated in FIG. 21A. As such, the proximal end 168 of the outer shaft 84 of the shaft assembly 60 may be interference fit within the proximal opening 162 of the handle body 152, so that the outer shaft 84 of the shaft assembly 60 is affixed to the handle body 152, while still being capable of rotating within the handle body 152 about the longitudinal axis 86 of the shaft assembly 60.

Figure 22A:
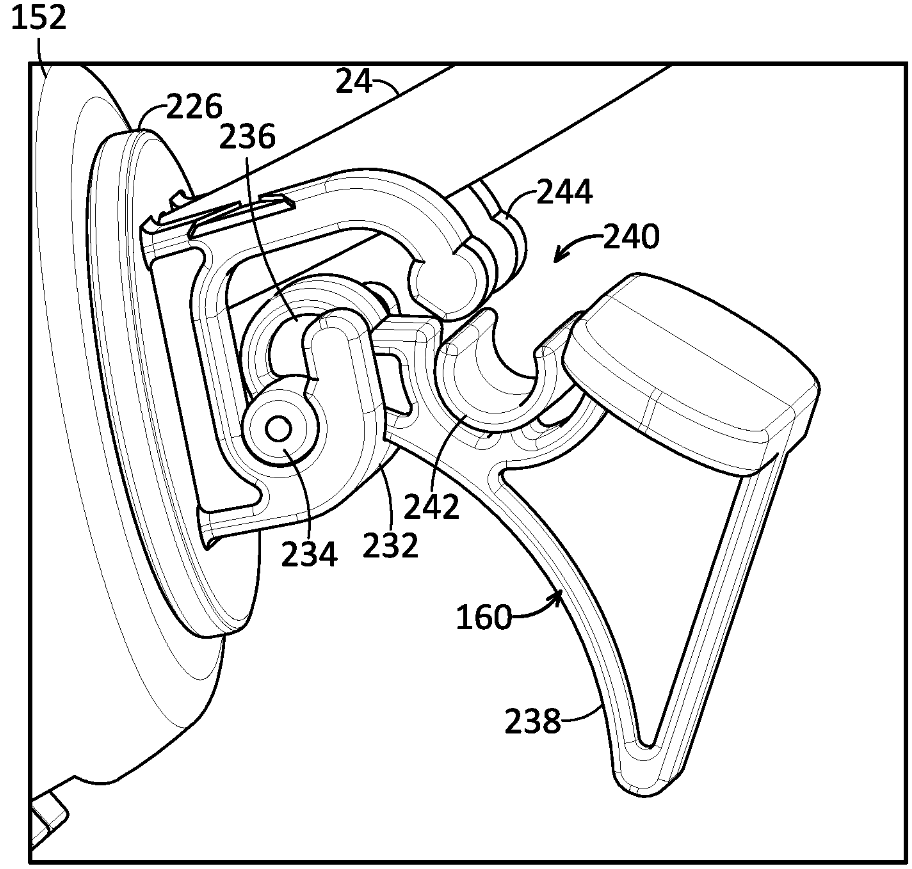
FIG. 22A is a perspective view of a uterine manipulator locking assembly of the tissue cutting device of FIG. 6, particularly showing the uterine manipulator locking assembly in an unlocked position.
Figure 22B:
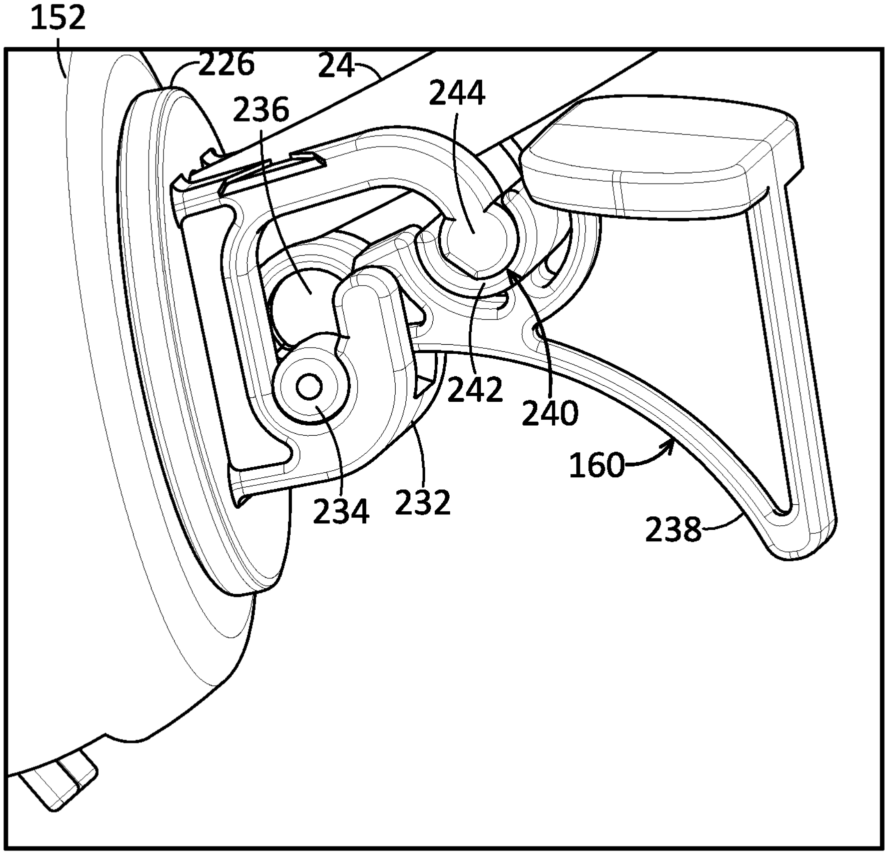
FIG. 22B is a perspective view of the uterine manipulator locking assembly of FIG. 22A, particularly showing the uterine manipulator locking assembly in a locked position.

Referring to FIGS. 21A and 22B, the rotational assembly 154 facilitates rotating the cutting element 92 about the longitudinal axis 86 of the shaft assembly 60, such that the cutting element 92 can circumferentially incise the vaginal-cervical junction J of the patient P. The rotational assembly 154 is affixed within a central cavity 155 of the handle body 152, and thus, rotates together with the handle body 152 about the longitudinal axis 86 of the shaft assembly 60. The rotational assembly 154 comprises an annular fitting element 174 affixed within the handle body 152 (and in the illustrated embodiment, a hex fitting) and a knurled boss 176 (shown best in FIG. 6) distally extending from the annular fitting element 174. A proximal end 178 of the inner shaft 82 of the shaft assembly 60 is disposed within boss 176 of the rotational assembly 154. The outer diameter of the proximal end 178 of the inner shaft 82 is smaller than the inner diameter of the boss 176, and a flexible or pliable sleeve 180 (shown in phantom in FIG. 21A) is affixed over (e.g., heat shrunk) the exterior of the boss 176 and the exterior of the proximal end 178 of the inner shaft 82, thereby creating a flexible joint between the rotational assembly 154 and the inner shaft 82 of the shaft assembly 60. In this manner, torque may be transmitted from the rotational assembly 154 to the inner shaft 82 of the shaft assembly 60 more efficiently when the colpotomy device 14 is bent at the junction between the handle body 152 and the shaft assembly 60. The rigid shaft 24 of the uterine manipulator 20 extends through a through-hole 182 (shown best in FIG. 6) formed through the center of the annular fitting element 174 and boss 176, such that the rigid shaft 24 of the uterine manipulator 20 may both be longitudinally and rotationally displaced relative to the handle body 152.

Thus, it can be appreciated that rotation of the handle body 152 relative to the outer shaft 84 of the shaft assembly 60 (shown by arrow 177 in FIGS. 15A-15B) causes the inner shaft 82 of the shaft assembly 60 (via the rotational assembly 154) to rotate relative to the outer shaft 84 of the shaft assembly 60 about the longitudinal axis 86 of the shaft assembly 60 (shown by arrow 179 in FIGS. 15A-15B), which in turn, causes the inner cup 104 of the colpotomy cup assembly 90, along with the cutting element 92, to rotate relative to the outer cup 106 of the colpotomy cup assembly 90 about the longitudinal axis 86 of shaft assembly 60.

Referring to FIGS. 17-19, and 21A-21B, the mechanical deployment actuator 156 facilitates selective advancement of the cutting element 92 from the colpotomy cup assembly 90 from its stored position to its deployed position, and retracting the cutting element 92 into the colpotomy cup assembly 90 from its deployed position to its stored position, and allowing the physician to temporarily lock the cutting element 92 in the stored position or in different deployment positions. The mechanical deployment actuator 156 includes a deployment mechanism 184 and a brake 186.

Figure 21B:
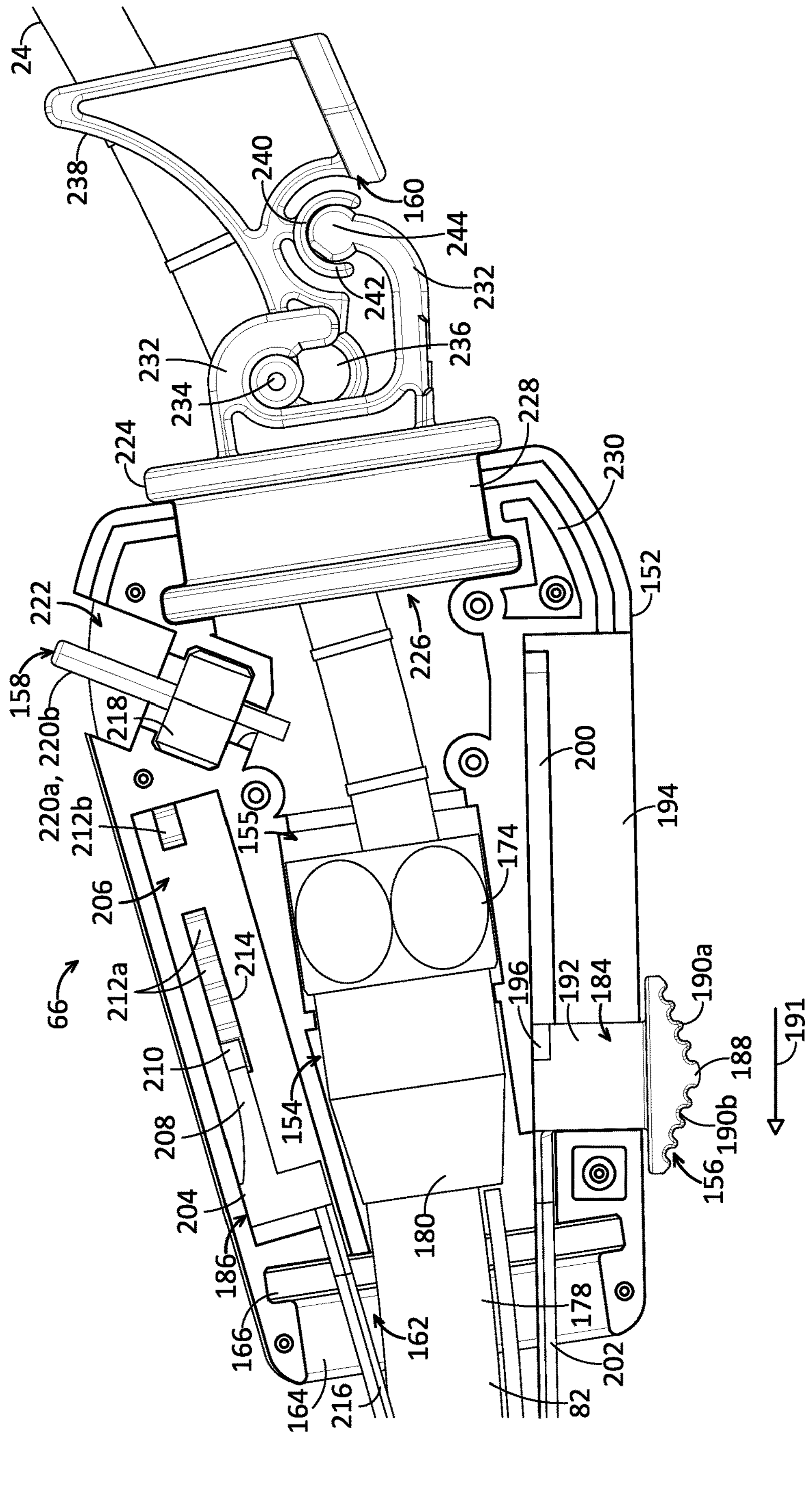
FIG. 21B is a cut-away view of the handle assembly of FIG. 21A, particularly showing the handle body of the handle assembly in another rotational orientation.

The deployment mechanism 184 comprises a slidable external thumb piece 188 that resides outside of the handle body 152 and is configured for being manually translated relative to the handle body 152. As best shown in FIGS. 21A-21B, the external thumb piece 188 has proximal and distal ramped surfaces 190*a*, 190*b* that are textured to facilitate distal and proximal movement of the external thumb piece 188 by the physician. The external thumb piece 188 is located on the handle body 152, such that the physician may ergonomically slide the external thumb piece 188 with a thumb while grasping the handle body 152 with one hand.

The deployment mechanism 184 further comprises a block 192 extending downward from the external thumb piece 188 through a slot 194 formed through the handle body 152 into the interior of the handle body 152, and a guide tab 196 laterally extending from the block 192 and slidably disposed in a horizontal guide slot 200 (shown in FIGS. 15A and 15B) within handle body 152. The block 192 is slidably disposed in the slot 194 of the handle body 152. In this manner, the external thumb piece 188 may slide along the handle body 152 along a defined longitudinal path.

The deployment mechanism 184 further comprises a resilient arm 202 that distally extends from the block 192 out through the distal opening 162 of the handle body 152, and is affixed to the proximal end 134 of the slidable electrode sleeve 130. The flexibility of the resilient arm 202 allows the coupling between the deployment mechanism 184 and the slidable electrode sleeve 130 and compensates for curved portions of rigid shaft 24 where resilient arm 202 bends with the shaft assembly 60). As such, displacement of the deployment mechanism 184 (shown by arrow 183 in FIGS. 15A and 15B) correspondingly displaces the slidable electrode sleeve 130 relative to the shaft assembly 60 along the longitudinal axis 86 (shown by arrow 185 in FIGS. 15A and 15B). That is, displacement of the deployment mechanism 184 in the distal direction correspondingly displaces the slidable electrode sleeve 130 in the distal direction along the longitudinal axis 86 of the shaft assembly 60, thereby distally advancing the cutting element 92 in the distal direction from its stored position (FIG. 11A) to its deployed position (FIG. 11B) within the colpotomy cup assembly 90. Conversely, displacement of the deployment mechanism 184 in the proximal direction correspondingly displaces the slidable electrode sleeve 130 in the proximal direction along the longitudinal axis 86 of the shaft assembly 60, thereby retracting the cutting element 92 in the proximal direction from its deployed position (FIG. 11B) to its stored position (FIG. 11A) within the colpotomy cup assembly 90.

As best shown in FIGS. 21A and 21B, the brake 186 is configured for selectively locking the deployment mechanism 184 in one of a plurality of different axial (in this case five positions), and comprises a block 204 slidably disposed within a cavity 206 formed in the handle body 152. The brake 186 further comprises a pair of spring arms 208 extending proximally from the block 204. Each spring arm 208 comprises a lateral detent 210 configured to interact with a series of teeth 212 inset along a pair of slots 214 (only one shown) extending along the lateral sides of the cavity 206 in the handle body 152. The brake 186 further comprises a resilient arm 216 that distally extends from the block 204 out through the distal opening 162 of the handle body 152, and is affixed to the proximal end 134 of the slidable electrode sleeve 130. The flexibility of the resilient arm 216 allows the coupling between the brake 186 and the slidable electrode sleeve 130 compensates for curved sections of the rigid shaft 24 where resilient arm 216 bends bending with the shaft assembly 60).

Thus, as the deployment mechanism 184 displaces the slidable electrode sleeve 130 in the distal direction to advance the cutting element 92 from the colpotomy cup assembly 90 or in the proximal direction to retract the cutting element 92 within the colpotomy cup assembly 90, the brake 186 correspondingly moves (via application of force by the slidable electrode sleeve 130) in the distal direction or proximal direction. As the brake 186 moves, the lateral detents 210 on the respective spring arms 208 of the brake 186 interact with the series of teeth 212 in the pair of slots 214 within the handle body 152 as the block 204 of the brake 186 correspondingly moves within the cavity 206 of the handle body 152. The resiliency of the pair of spring arms 208 of the deployment locking mechanism 186 provide tactile feedback to the physician as the lateral detents 210 to move in and out of the series of teeth 212 inset along the pair of slots 214 as the block 204 moves distally or proximally in the cavity 206 of the handle body 152. Thus, deployment mechanism 184, and thus the cutting element 92, may be selectively placed in one of a plurality of axial positions in a ratcheted manner. In the illustrated embodiment, the cutting element 92 may be selectively placed in one of four different deployment positions (via teeth 212*a*) or one stored position (via teeth 212*b*).

Notably, the path length between the deployment mechanism 184 and the cutting element 92 for the configuration in FIGS. 15B and 21A, where the deployment mechanism 184 is on the inner surface of the arc formed by the shaft assembly 60 (in this case, when the deployment mechanism 184 is at the top), is shorter than the path length between the deployment mechanism 184 and the cutting element 92 for the configuration in FIG. 21B, where the deployment mechanism 184 is on the outer surface of the arc formed by the shaft assembly 60 (in this case, when the deployment mechanism 184 is at the bottom). Consequently, as the handle body 152 is rotated relative to the outer shaft 84 of the shaft assembly 60 between the configuration illustrated in FIGS. 15B and 21A to the configuration in FIG. 21B, the length of the exposed portion of the cutting element 92 may, without intervention, change as the cutting element 92 traverses an arcuate path around the perimeter of the colpotomy cup assembly 90.

However, to prevent or mitigate the shortening and lengthening of the exposed portion of the cutting element 92 as the handle body 152 is rotated relative to the colpotomy cup assembly 90, and thus the cutting element 92 is rotated around the colpotomy cup assembly 90, the brake 186 temporarily locks the slidable electrode sleeve 130, and thus the cutting element 92 in place, while the deployment mechanism 184 is allowed to slide slightly relative to the handle body 152. Preferably, the brake 186 and cutting element 92 are clocked (i.e., circumferentially offset) from each other by 180 degrees, such that the change in the arcuate path between the handle body 152 and the cutting element 92 is completely compensated for as the handle body 152 is rotated relative to the outer shaft 84 of the shaft assembly 60 (i.e., the average arc length from the brake 186 and the distal rim 102 of the colpotomy cup assembly 90 remains constant through 360 degrees of rotation).

For example, without intervention, if the handle body 152 is rotated relative to the outer shaft 84 of the shaft assembly 60 from the configuration illustrated in FIGS. 15B and 21A (i.e., cutting element 92 is in 12 o'clock position) to the configuration in FIG. 21B (i.e., the cutting element 92 is in the 6 o-clock position), the arcuate path between the handle body 152 and the cutting element 92 will correspondingly increase from its minimum length (shortest path length) to its maximum length (longest path length), thereby causing the cutting element 92 to be proximally displaced relative to the colpotomy cup assembly 90 (i.e., the length of the exposed portion of the cutting element 92 will decrease). However, because the arcuate path along the electrode sleeve 130 in alignment with the brake 186 will decrease by the same distance as the arcuate path between the handle body 152 and the cutting element 92 increases, the brake 18 (which is locked in position) will distally displace the electrode sleeve 130, such that the cutting element 92 is not displaced relative to the colpotomy cup assembly 90.

In contrast, without intervention, if the handle body 152 is rotated relative to the outer shaft 84 of the shaft assembly 60 from the configuration in FIG. 21B (i.e., the cutting element 92 is in the 6 o-clock position) to the configuration illustrated in FIGS. 15B and 21A (i.e., cutting element 92 is in 12 o'clock position), the arcuate path between the handle body 152 and the cutting element 92 will correspondingly decrease from its maximum length (longest path length) to its minimum length (shortest path length), thereby causing the cutting element 92 to be distally displaced relative to the colpotomy cup assembly 90 (i.e., the length of the exposed portion of the cutting element 92 will increase). However, because the arcuate path along the electrode sleeve 130 in alignment with the brake 186 (opposite the cutting element 92) will increase by the same distance as the arcuate path between the handle body 152 and the cutting element 92 decreases, the brake 18 (which is locked in position) will proximally displace the electrode sleeve 130 relative to the colpotomy cup assembly 90, such that the cutting element 92 is not displaced relative to the colpotomy cup assembly 90.

In alternative embodiments, the brake 186 and cutting element 92 may be clocked (i.e., circumferentially offset) from each other by less than 180 degrees, such that the change in the arcuate path between the handle body 152 and the cutting element 92 is only partially compensated for as the handle body 152 is rotated relative to the outer shaft 84 of the shaft assembly 60. In this case, it may be assumed that some change in the exposed portion of the cutting element 92 can be tolerated.

Referring to FIGS. 21A and 21B, the electrical ablation port 158 electrically couples the RF generator 14 to the tissue cutting device 22, thereby providing electrical ablation energy to the tissue cutting device 22, and in the illustrated embodiment, bipolar electrical ablation energy between the tissue cutting element 92 and the ground electrode 94 of the cutting head 64. The electrical ablation port 158 comprises a connector block 218 affixed within a cavity 222 of the handle body 152 and two electrical terminals 220*a*, 220*b* extending through the connector block 218. The electrical wire 146 is connected to the electrical terminal 220*a* (e.g., via soldering), while the electrical wire 148 is connected to the electrical terminals 220*b*, such that the electrical terminals 220*a*, 220*b* are electrically coupled respectively to the cutting element 92 and ground electrode 94 of the colpotomy cup assembly 90. In one embodiment, the electrical wires 146, 148 pass through channels (not shown) formed along the inner surface of the handle body 152, such that the electrical wires 146, 148 may pass on opposite sides between the inner surface of the handle body 152 and the annular fitting element 174 to the respective electrical terminals 220*a*, 220*b*.

Referring further to FIGS. 22A-22B, the uterine manipulator locking assembly 160 selectively locks or unlocks the tissue cutting device 22 to the rigid shaft 24 of the uterine manipulator 20.

The uterine manipulator locking assembly 160 comprises a bushing 224 affixed within proximal end of the handle body 152 and through which the rigid shaft 24 of the uterine manipulator 20 extends. In the illustrated embodiment, the bushing 224 comprises a bore 226 through which the rigid shaft 24 of the uterine manipulator 20 extends, and an annular recess 228 that cooperates with an annular lip 230 of the handle body 152 in a manner that affixes the bushing 224 within the handle body 152, such that the bushing 224, along with the uterine manipulator locking assembly 160, rotates with the handle body 152. In an alternative embodiment, the annular recess 228 cooperates within the annular lip 230 of the handle body 152 in a manner that allows the bushing 224 and handle body 152 to slide relative to each other, such that the bushing 224, along with the uterine manipulator locking assembly 150 remains stationary as the handle body 152 rotates.

The uterine manipulator locking assembly 160 further comprises a cradle 232 affixed to the bushing 224 and disposed on the exterior of the handle body 152. The uterine manipulator locking assembly 160 further comprises a cam shaft 234 rotatably disposed in the cradle 232, and an eccentric cam 236 affixed to the cam shaft 234, such that the eccentric cam 238 may be rotated within the cradle 232 about the longitudinal axis of the cam shaft 234. The uterine manipulator locking assembly 160 further comprises a lever 238 in the form of a mechanical finger actuator affixed to the eccentric cam 236, such that movement of the lever 238 rotates the cam 236 about the longitudinal axis of the cam shaft 234.

In particular, the lever 238 may be rotated between a locked (or closed) position (FIG. 22A) and an unlocked (or open) position (FIG. 22B). The rigid shaft 24 of the uterine manipulator 20 passes from the bushing 224 and through or adjacent to the cradle 232 in close proximity to the eccentric cam 236, such that the eccentric cam 236, when lever 238 is rotated from its locked position towards the rigid shaft 24 to its unlocked position (FIG. 22B), rotates to engage the rigid shaft 24, thereby pinching the rigid shaft 24 between the eccentric cam 236 and the inside of the bushing 224, and locking the rigid shaft 24 relative to the handle body 152; and when the lever 238 is rotated from its unlocked position away from the rigid shaft 24 to its locked position (FIG. 22A), rotates to disengage the rigid shaft 24, thereby releasing the rigid shaft 24 between the eccentric cam 236 and the inside of the bushing 224, and unlocking the rigid shaft 24 relative to the handle body 152.

The uterine manipulator locking assembly 160 further comprises a snap joint 240 that allows the lever 238 to be temporarily affixed to the cradle 232 while in the locked position, and thus maintaining the rigid shaft 24 relative to the handle body 152, and then released from the cradle 232 to place the lever 226 in the unlocked position, and thus allowing the rigid shaft 24 to be displaced relative to the handle body 152. In the illustrated embodiment, the snap joint 240 comprises a resilient U-shaped portion 242 permanently affixed to the lever 238 and one or more bulbous portions 244 (in the exemplary case, a pair of bulbous portions 244) permanently affixed to the cradle 232, although in alternative embodiments, the U-shaped portion 242 is permanently affixed to the cradle 232 and the bulbous portions 244 is permanently affixed to the lever 226. The inner contour of the U-shaped portion 242 and the outer contour of the bulbous portions 244 match, such that they may be interference fit together to form the snap joint 240. That is, when the lever 238 is moved from its unlocked position to its locked position, the U-shaped portion 242 of the snap joint 240 expands to receive the bulbous portion 244 of the snap joint 240, thereby providing an interference fit between the U-shaped portion 242 and the bulbous portions 244 of the snap joint 240. Conversely, when the lever 238 is moved from its locked position, the U-shaped portion 242 of the snap joint 240 expands to release the bulbous portions 244 of the snap joint 240, thereby allowing the lever 238 to be placed into its unlocked position.

Figure 23:
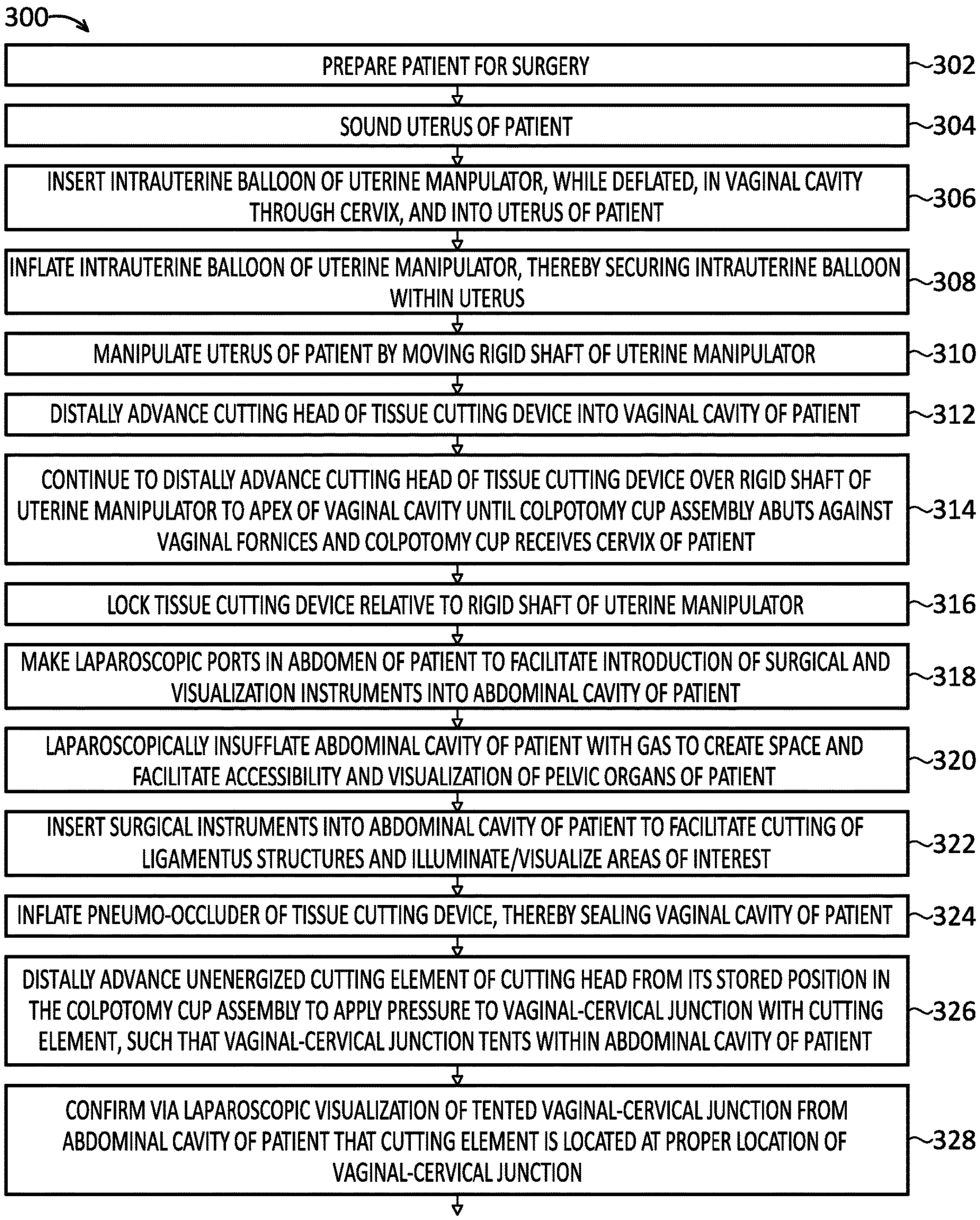
FIG. 23 is a flow diagram illustrating one exemplary method of operating the hysterectomy system of FIG. 1 to perform a laparoscopic assisted vaginal hysterectomy (TVLH) procedure on a female patient.
Figure 23:
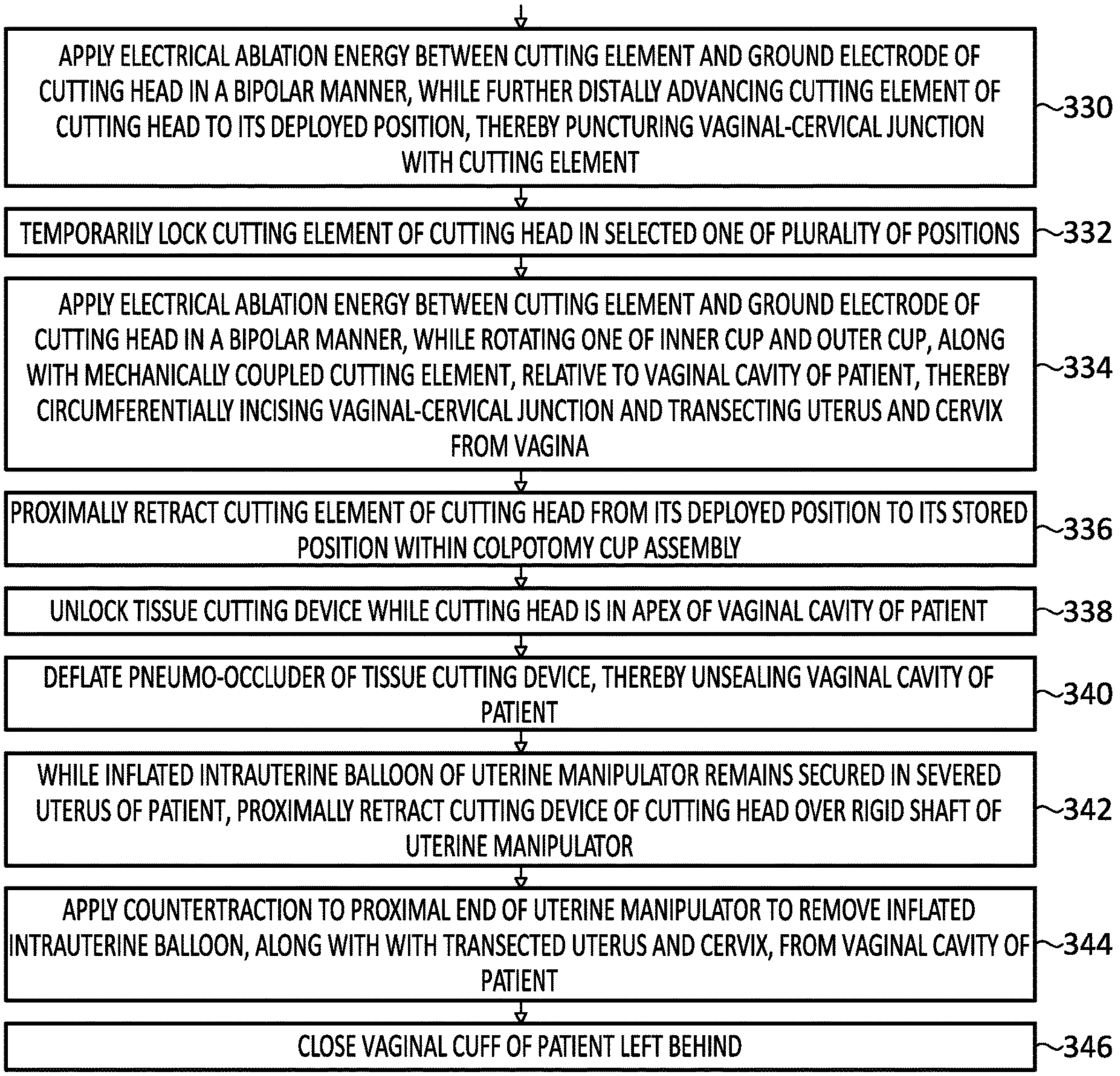

Referring to FIG. 23, one exemplary method 300 of operating the colpotomy system 10 to perform a laparoscopic assisted vaginal hysterectomy (LAVH) on the patient P will now be described.

First, the patient P is prepared for surgery according to procedures that are well known in the surgical arts (step 302). For example, the patient P may be oriented in a supine-lithotomy position on an operating table, such that the legs of the patient P rest in raised stirrups. A surgeon, anesthesiologist, and medical assistant may be present alongside the operating table. Other healthcare personnel may be present well.

Once the patient P is prepared, the surgeon sounds the uterus U of the patient P (step 304). While sitting or standing between the patient's legs, the surgeon begins insertion of the colpotomy assembly 12 by guiding the intrauterine manipulator 20 with one hand while hold the tissue cutting device 22 with the other hand. In particular, the intrauterine balloon 26 of the uterine manipulator 20, while deflated, is inserted in the vaginal cavity VC, and guided through the cervix C into the uterus U of the patient P (step 306). Once the tip of the colpotomy assembly 12 is inserted to an appropriate length, the intrauterine balloon 26 of the uterine manipulator 20 is inflated, thereby securing the intrauterine balloon 26 within the uterus U of the patient P (step 308). In the illustrated embodiment, this step is accomplished by conveying fluid from the first source of fluid 16, through the lumen of the rigid shaft 24, out through the distal inflation port 36, and into the interior region of the intrauterine balloon 26 (see FIGS. 1 and 5). At any time during the hysterectomy procedure, the uterus U of the patient P may be manipulated by moving the rigid shaft 24 of the uterine manipulator 20 (step 310). In the illustrated embodiment, this step is accomplished by grasping the handle body 46 of the handle assembly 28 and moving it to accordingly move the rigid shaft 24 relative to the vagina V of the patient P, and thus, the inflated intrauterine balloon 26 within the uterus U of the patient P (see FIGS. 1-4).

Then, the surgeon distally advances the cutting head 64 of the tissue cutting device 22 into the vaginal cavity VC of the patient P with one hand while the other holds handle body 46 (step 312). The surgeon continues to distally advance the tissue cutting device 22 over the rigid shaft 24 of the uterine manipulator 12 until the colpotomy cup assembly 90 is positioned around the vaginal fornices VF of the patient P (step 314). In the illustrated embodiment, these steps are accomplished by grasping and distally displacing the handle body 152 of the handle assembly 66 relative to the rigid shaft 24 of the uterine manipulator 14, such that the shaft assembly 60 and cutting head 64 is correspondingly distally displaced relative to the rigid shaft 24 of the uterine manipulator 14 (see FIGS. 2 and 3).

Next, the tissue cutting device 22 is locked relative to the rigid shaft 24 of uterine manipulator 20 (step 316). This step is accomplished by rotating the lever 238 of the uterine manipulator locking assembly 160 located on the handle body 152 of the handle assembly 66 from its unlocked position to its locked position, such that the eccentric cam 236 rotates to engage the rigid shaft 24, thereby pinching the rigid shaft 24 between the eccentric cam 236 and the inside of the bushing 224, and locking the rigid shaft 24 relative to the handle body 152 (see FIGS. 22A and 22B).

Next, in a conventional manner, multiple laparoscopic ports are made in the abdomen of the patient P to facilitate the introduction of surgical and visualization instruments into the abdominal cavity AC of the patient P (step 318). The abdominal cavity AC of the patient P is laparoscopically insufflated via one of the ports with a gas to create space and facilitate accessibility and visualization of the pelvic organs of the patient P (step 320), and laparoscopic surgical instruments may be inserted through the other ports into the abdominal cavity AC of the patient P to facilitate cutting of ligamentus structures and/or illuminate/visualize areas of interest (step 322).

Next, the pneumo-occluder 72 of the tissue cutting device 22 is inflated, thereby sealing the vaginal cavity VC of the patient P before the colpotomy incision is made (step 324). In the illustrated embodiment, this step is accomplished by conveying fluid from the second source of fluid 18, through the inflation tube 74, and into the interior region of the pneumo-occluder 72 (see FIGS. 1-3).

Next, while sitting or standing between the patient's legs, the surgeon distally advances the (unenergized) cutting element 92 of the cutting head 64 from its stored position in the colpotomy cup assembly 90 to apply pressure to the vaginal-cervical junction J with the cutting element 92, such that the vaginal-cervical junction J tents within the abdominal cavity AC of the patient P (step 326). In the illustrated embodiment, this step is accomplished by displacing the external thumb piece 188 of the deployment mechanism 184 relative to the handle body 152 of the handle assembly 166 in the distal direction, such that the electrode sleeve 130 slides distally relative to the shaft assembly 60 along the longitudinal axis 86, thereby distally advancing the distal end 118 of the cutting element 92 from the electrode channel 124 until the vaginal-cervical junction J tents within the abdominal cavity AC of the patient P (see FIGS. 15A-15B)

The physician then confirms via laparoscopic visualization of the tented vaginal-cervical junction J from the abdominal cavity AC of the patient P that the cutting element 92 is located at the proper location of the vaginal-cervical junction J (step 328). Once the proper location of the cutting element 92 relative to the vaginal-cervical junction J has been confirmed, electrical ablation energy is applied between the cutting element 92 and the ground electrode 94 of the cutting head 64 in a bipolar manner, such as via a foot switch, while further distally advancing the cutting element 92 of the cutting head 64 from the colpotomy cup assembly 90 to its deployed position, thereby puncturing the vaginal-cervical junction J with the cutting element 92 (step 330).

In the illustrated embodiment, this step is accomplished by operating the RF generator 14 to deliver the electrical ablation energy via the electrical ablation port 158 located on the handle body 152 of the handle assembly 66. Electrical ablation energy is conveyed between the wires 146, 148, and thus between the cutting element 92 and the ground electrode 94 of the cutting head 64, while further displacing the external thumb piece 188 of the deployment mechanism 184 relative to the handle body 152 of the handle assembly 66 in the distal direction, such that the electrode sleeve 130 slides distally relative to the shaft assembly 60 along the longitudinal axis 86, thereby distally advancing the distal end 118 of the cutting element 92 from the electrode channel 124 of the colpotomy cup assembly 90 and puncturing through the vaginal-cervical junction J into the abdominal cavity AC of the patient P (see FIGS. 1 and 15A-15B). In an alternative method, electrical ablation energy is applied between the cutting element 92 of the cutting head 64 and an external ground electrode (not shown) in a monopolar manner.

In an optional method, the cutting element 92 of the cutting head 64 is temporarily locked in a selected one of a plurality of positions (step 332). In the illustrated embodiment, this step can be accomplished by ceasing displacement of the external thumb piece 188 of the deployment mechanism 184 once tactile resistance is felt by the physician via mechanical interference between the lateral detents 210 of the spring arms 208 of the brake 186 and the series of teeth 212 along the pair of slots 214 extending along the lateral sides of the cavity 206 in the handle body 152 (see FIG. 21).

Next, while applying electrical ablation energy between the cutting element 92 and the ground electrode 94 of the cutting head 64 in a bipolar manner, the inner cup 104 is rotated relative to the outer cup 106, along with the mechanically coupled cutting element 92. Rotating the cutting element 92 relative to the vaginal cavity VC circumferentially incises the vaginal-cervical junction J, and transects the uterus U and cervix C from the vagina V of the patient P (step 334). In the illustrated embodiment, this step can be accomplished by rotating the handle body 152, such that the inner shaft 82 rotates (via the rotational assembly 154 located within the handle body 152 of the handle assembly 66), thereby causing the inner cup 104 and the cutting element 92 to rotate about the longitudinal axis 86 of the shaft assembly 60 (see FIGS. 9A-9C and 15A-15B). When the shaft assembly 60 of the colpotomy device 22 is located on a curve portion of the rigid shaft 24, rotating the handle body 152 allows the deployment mechanism 184 to slide relative to the handle body 152 while the brake 184 locks the electrode sleeve 130, and thus prevent or minimize the lengthening or shortening of the exposed length of the cutting element 92 during rotation.

Next, the cutting element 92 of the cutting head 64 is proximally retracted from its deployed position to its stored position within the colpotomy cup assembly 90 (step 336). In the illustrated embodiment, this step is accomplished by displacing the external thumb piece 188 of the deployment mechanism 184 relative to the handle body 152 of the handle assembly 166 in the proximal direction, such that the electrode sleeve 130 slides proximally along the longitudinal axis 86, thereby retracting the distal end 118 of the cutting element 92 into the electrode channel 124 of the colpotomy cup assembly 90 (see FIGS. 1 and 15A-15B).

Then, the tissue cutting device 22 is unlocked while the cutting head 64 is in the apex of the vaginal cavity VC of the patient P (step 338). In the illustrated embodiment, this step can be accomplished by reversing step 314. Next, the pneumo-occluder 72 is deflated, thereby unsealing the vaginal cavity VC of the patient (step 340). In the illustrated embodiment, this step is accomplished by withdrawing fluid from the interior region of the pneumo-occluder 72, back through the inflation tube 74, and into the second source of fluid 18 (see FIGS. 1-3).

Then, while the inflated intrauterine balloon 26 of uterine manipulator 20 remains secured in the severed uterus U of the patient P, the cutting head 64 of the tissue cutting device 22 is proximally retracted over the rigid shaft 24 of the uterine manipulator 14 until the cutting head 64 is removed from the vaginal cavity VC of the patient P (step 342). This step is accomplished by grasping and proximally displacing the handle body 152 of the handle assembly 66 relative to the rigid shaft 24 of the uterine manipulator 14, such that the shaft assembly 60 and cutting head 64 are correspondingly proximally displaced relative to the rigid shaft 24 of the uterine manipulator 14 (see FIGS. 2 and 3).

By applying countertraction to the proximal end of uterine manipulator 20, the inflated intrauterine balloon 26 is removed, along with the transected uterus U and cervix C, from the vaginal cavity VC of the patient P by (step 344). Alternatively, the transected uterus U and cervix C of the patient P may be removed laparoscopically by cutting the uterus U into small pieces and removing them through a laparoscopic port. The vaginal cuff of the vagina V of the patient P left behind may be closed using means known to those skilled in the art, including, but not limited to, sutures, staples, and/or glue (step 346). A vaginal cuff closure technique, a laparoscopic suturing system, such as that described in U.S. Provisional Application Ser. No. 62/986,257, entitled "Vaginal Cuff Closure Laparoscopic Suture Passer," which is expressly incorporated herein, can be used to close the cuff of the vagina V of the patient P.

Inventive Methods Utilizing the Foregoing Embodiments

In accordance with one aspect of the disclosed inventions, a method is provided for performing a hysterectomy on a patient using a cutting head that includes a colpotomy cup assembly having an inner cup and an outer cup, and a cutting element mechanically coupled to one of the inner cup and the outer cup, wherein the method comprises: introducing the cutting head into a vaginal cavity of the patient; distally advancing the cutting head to the apex of the vaginal cavity of the patient; puncturing through a vaginal-cervical junction with the cutting element into an abdominal cavity of the patient; rotating the inner cup, along with the mechanically coupled cutting element, relative to the vaginal cavity, while the outer cup is stationary relative to the vaginal cavity, thereby circumferentially incising the vaginal-cervical junction to transect the uterus and cervix from the vagina of the patient; and removing the uterus and cervix from the patient, for example, through the vaginal cavity of the patient.

The method may further include one or more of (i) distally advancing the cutting head to the apex of the vaginal cavity of the patient until the colpotomy cup assembly abuts against vaginal fornices of the patient and receives a cervix of the patient; (ii) visualizing the location of the cutting element in the abdominal cavity via a laparoscopic procedure; (iii) insufflating the abdominal cavity, while sealing the vaginal cavity with a pneumo-occluder prior to circumferentially incising the vaginal-cervical junction of the patient, thereby preventing insufflation gas, when the vaginal-cervical junction is being circumferentially incised, from escaping the abdominal cavity from the patient through the vaginal cavity; (iv) retracting a distal portion of the cutting element within the colpotomy cup assembly while the cutting head is distally advanced to the apex of the vaginal cavity of the patient; and distally advancing the distal portion of the cutting element from the colpotomy cup assembly to puncture the vaginal-cervical junction of the patient with the cutting element; (v) distally advancing the distal portion of the cutting element from the colpotomy cup assembly at an acute angle (e.g., in a range of 100-40°) relative to a longitudinal axis of the vaginal cavity of the patient; (vi) retracting the cutting element into the colpotomy cup assembly, wherein a proximal portion of the cutting element proximally extends from the colpotomy cup assembly, and wherein the proximal portion of the cutting element is distally advanced along the longitudinal axis of the vaginal cavity to distally advance a distal portion of the cutting element from the colpotomy cup assembly at the acute angle relative to the longitudinal axis of the vaginal cavity; (vii) temporarily locking the cutting element in a selected one of a plurality of positions; (viii) locking the cutting element relative to the colpotomy cup assembly while rotating the one of the inner cup and the outer cup, along with the mechanically coupled cutting element, relative to the vaginal cavity; (ix) applying electrical ablation energy to the cutting element while the cutting element circumferentially incises the vaginal-cervical junction of the patient; and (x) applying pressure to the vaginal-cervical junction by a distal tip of the cutting element prior to puncturing the vaginal-cervical junction with the cutting element, such that the vaginal-cervical junction to tents within the abdominal cavity of the patient, and further applying the electrical ablation energy to the cutting element to puncture the vaginal-cervical junction with the cutting element after the vagina-cervical junction has been tented within the abdominal cavity of the patient. For example, a ground electrode may be disposed on the inner cup, and applying electrical ablation energy to the cutting element comprises applying electrical ablation energy between the cutting element and the ground electrode.

The method may optionally further comprise: introducing an intrauterine balloon affixed to a rigid shaft through the vaginal cavity of the patient; guiding the intrauterine balloon through the cervix of the patient and into the uterus of the patient; inflating the intrauterine balloon before circumferentially incising the vaginal-cervical junction of the patient, thereby securing the intrauterine balloon within the uterus of the patient; and moving the rigid shaft, thereby manipulating the uterus of the patient via the inflated intrauterine balloon. The inflated intrauterine balloon may be triangular. The inflated intrauterine balloon may optionally be non-compliant, such that the uterus conforms to the inflated intrauterine balloon. The method may further comprise locking the inflated intrauterine balloon relative to the cutting head while the cutting head is in the apex of the vaginal cavity of the patient. The method may optionally further comprise removing the uterus and cervix from the patient via the vaginal cavity after the vaginal-cervical junction has been circumferentially incised by proximally displacing the rigid shaft relative to the vagina while the inflated intrauterine balloon is secured within the uterus.

In accordance with another aspect of the disclosed inventions, a method is provided for performing a hysterectomy on a patient using a cutting head that includes a colpotomy cup assembly, and a cutting element associated with the colpotomy cup assembly, the method comprising: introducing the cutting head into a vaginal cavity of the patient; distally advancing the cutting head to the apex of the vaginal cavity of the patient; applying pressure to a vaginal-cervical junction by a distal tip of the cutting element, such that the vaginal-cervical junction tents within the abdominal cavity of the patient; puncturing through the vaginal-cervical junction with the cutting element into the abdominal cavity of the patient; rotating the cutting element relative to the vaginal cavity, thereby circumferentially incising the vaginal-cervical junction to transect the uterus and cervix from the vagina of the patient; and removing the uterus and cervix from the patient, e.g., through the vaginal cavity of the patient. The cutting head may be distally advanced to the apex of the vaginal cavity of the patient until the colpotomy cup assembly abuts against vaginal fornices of the patient and receives a cervix of the patient. The method may further include: insufflating the abdominal cavity; and sealing the vaginal cavity with a pneumo-occluder prior to circumferentially incising the vaginal-cervical junction of the patient, thereby preventing insufflation gas, when the vaginal-cervical junction is being circumferentially incised, from escaping the abdominal cavity from the patient through the vaginal cavity.

The method may further include: retracting a distal portion of the cutting element within the colpotomy cup assembly while the cutting head is distally advanced to the apex of the vaginal cavity of the patient; and distally advancing the distal portion of the cutting element from the colpotomy cup assembly to puncture the vaginal-cervical junction of the patient with the cutting element, wherein the distal portion of the cutting element may be distally advanced from the colpotomy cup assembly at an acute angle relative to a longitudinal axis of the vaginal cavity of the patient. The acute angle may be in the range of 20°-65°. The method of claim may further include temporarily locking the cutting element in a selected one of a plurality of positions.

The method may further include applying electrical ablation energy to the cutting element while the cutting element circumferentially incises the vaginal-cervical junction of the patient. For example, the method may include comprising applying the electrical ablation energy to the cutting element to puncture the vaginal-cervical junction with the cutting element after the vagina-cervical junction has been tented within the abdominal cavity of the patient. A ground electrode may be disposed on the colpotomy cup assembly, so that applying electrical ablation energy to the cutting element comprises applying electrical ablation energy between the cutting element and the ground electrode.

The method may further include: introducing an intrauterine balloon affixed to a rigid shaft through the vaginal cavity of the patient; guiding the intrauterine balloon through the cervix of the patient and into the uterus of the patient; inflating the intrauterine balloon before circumferentially incising the vaginal-cervical junction of the patient, thereby securing the intrauterine balloon within the uterus of the patient; and moving the rigid shaft, thereby manipulating the uterus of the patient via the inflated intrauterine balloon. For example, the method may include removing the uterus and cervix from the patient via the vaginal cavity after the vaginal-cervical junction has been circumferentially incised by proximally displacing the rigid shaft relative to the vagina while the inflated intrauterine balloon is secured within the uterus.

In accordance with yet another aspect of the disclosed inventions, a method is provided for performing a hysterectomy on a patient using an elongated shaft, a cutting head mechanically coupled to a distal end of the elongate shaft, and a sleeve slidably disposed around the elongated shaft, the cutting head including a colpotomy cup assembly and a cutting element associated with the colpotomy cup assembly, the method comprising: introducing the cutting head into a vaginal cavity of the patient; distally advancing the cutting head to the apex of the vaginal cavity of the patient; distally displacing the sleeve relative to the elongated shaft, thereby distally advancing a distal portion of the cutting element from the colpotomy cup assembly to puncture the vaginal-cervical junction of the patient with the cutting element; rotating the cutting element relative to the vaginal cavity, thereby circumferentially incising the vaginal-cervical junction to transect the uterus and cervix from the vagina of the patient; and removing the uterus and cervix, e.g., through the vaginal cavity.

Without limitation, the method may further include proximally displacing the sleeve relative to the elongated shaft, thereby retracting the distal portion of the cutting element within the colpotomy cup assembly to puncture the vaginal-cervical junction of the patient with the cutting element; and removing the colpotomy device from the vaginal cavity of the patient. For example, the colpotomy device may have a handle body mechanically coupled to a proximal end of the elongated shaft, and a mechanical deployment actuator slidably disposed on the handle body, and wherein distally displacing the sleeve relative to the elongated shaft comprises sliding the mechanical deployment actuator in the distal direction relative to the handle body The cutting head may be distally advanced to the apex of the vaginal cavity of the patient until the colpotomy cup assembly abuts against vaginal fornices of the patient and receives a cervix of the patient, wherein the method may further include visualizing the location of the cutting element in the abdominal cavity via a laparoscopic procedure. The method may include temporarily locking the cutting element in a selected one of a plurality of positions. The method may further include insufflating the abdominal cavity, and sealing the vaginal cavity with a pneumo-occluder prior to circumferentially incising the vaginal-cervical junction of the patient, thereby preventing insufflation gas from escaping the abdominal cavity from the patient through the vaginal cavity after the vaginal-cervical junction is circumferentially incised.

The method may further include applying electrical ablation energy to the cutting element while the cutting element circumferentially incises the vaginal-cervical junction of the patient. For example, the method may include comprising applying the electrical ablation energy to the cutting element to puncture the vaginal-cervical junction with the cutting element after the vagina-cervical junction has been tented within the abdominal cavity of the patient. A ground electrode may be disposed on the colpotomy cup assembly, so that applying electrical ablation energy to the cutting element comprises applying electrical ablation energy between the cutting element and the ground electrode.

The method may further include introducing an intrauterine balloon affixed to a rigid shaft through the vaginal cavity of the patient; guiding the intrauterine balloon through the cervix of the patient and into the uterus of the patient; inflating the intrauterine balloon before circumferentially incising the vaginal-cervical junction of the patient, thereby securing the intrauterine balloon within the uterus of the patient; and moving the rigid shaft, thereby manipulating the uterus of the patient via the inflated intrauterine balloon. The uterus and cervix may be removed from the patient via the vaginal cavity after the vaginal-cervical junction has been circumferentially incised by proximally displacing the rigid shaft relative to the vagina while the inflated intrauterine balloon is secured within the uterus.

In accordance with still another aspect of the disclosed inventions, a method is provided for performing a hysterectomy on a patient using a flexible elongated shaft, and a cutting head mechanically coupled to a distal end of the elongate shaft, the cutting head including a colpotomy cup assembly and a cutting element mechanically coupled to a distal end of the elongated shaft, the method comprising: introducing the cutting head into a vaginal cavity of the patient; distally advancing the cutting head to the apex of the vaginal cavity of the patient; bending the flexible elongated shaft; distally advancing a distal portion of the cutting element from the colpotomy cup assembly to puncture the vaginal-cervical junction of the patient with the cutting element into the abdominal cavity of the patient; locking the cutting element relative to the colpotomy cup assembly after the vaginal-cervical junction has been punctured; rotating the cutting element relative to the vaginal cavity while the flexible elongated shaft is bend and while the cutting element is locked relative to the colpotomy cup assembly, thereby circumferentially incising the vaginal-cervical junction to transect the uterus and cervix from the vagina of the patient; and removing the uterus and cervix from the patient, e.g., through the vaginal cavity.

The method may include using a sleeve slidably disposed around the elongated shaft, the cutting element being affixed to a distal end of the sleeve, the method further comprising distally displacing the sleeve relative to the elongated shaft, thereby distally advancing the distal portion of the cutting element from the colpotomy cup assembly to puncture the vaginal-cervical junction of the patient with the cutting element. The method may further include using a handle assembly having a handle body mechanically coupled to the cutting element, a deployment mechanism slidably disposed on the handle body and affixed to a proximal end of the sleeve, and a brake slidably disposed on the handle body and affixed to the proximal end of the sleeve, wherein distally advancing the distal portion of the cutting element from the colpotomy cup assembly to puncture the vaginal-cervical junction of the patient with the cutting element comprises distally sliding the deployment mechanism relative to the handle body, thereby distally displacing the sleeve relative to the flexible elongated shaft; and wherein locking the cutting element relative to the colpotomy cup assembly comprises locking the sleeve relative to the flexible elongate member with the brake. Without limitation, the brake may be clocked 180 degrees from the cutting element. Without limitation, the method may include locking the cutting element in a selected one of a plurality of positions.

The method may further include one or more of (i) rotating the handle body while the flexible elongated member is bent, thereby rotating the cutting element relative to the vaginal cavity, while allowing the deployment mechanism to slide relative to the handle body; (ii) distally advancing the cutting head to the apex of the vaginal cavity of the patient until the colpotomy cup assembly abuts against vaginal fornices of the patient and receives a cervix of the patient; (iii) visualizing the location of the cutting element in the abdominal cavity via a laparoscopic procedure; (iv) insufflating the abdominal cavity; and sealing the vaginal cavity with a pneumo-occluder prior to circumferentially incising the vaginal-cervical junction of the patient, thereby preventing insufflation gas, when the vaginal-cervical junction is being circumferentially incised, from escaping the abdominal cavity from the patient through the vaginal cavity.

The method may comprise applying the electrical ablation energy to the cutting element to puncture the vaginal-cervical junction with the cutting element after the vagina-cervical junction has been tented within the abdominal cavity of the patient. For example, and without limitation, a ground electrode may be affixed to the colpotomy cup assembly, with the method including applying electrical ablation energy to the cutting element comprises applying electrical ablation energy between the cutting element and the ground electrode.

The method may further comprise introducing an intrauterine balloon affixed to a rigid shaft through the vaginal cavity of the patient; guiding the intrauterine balloon through the cervix of the patient and into the uterus of the patient; inflating the intrauterine balloon before circumferentially incising the vaginal-cervical junction of the patient, thereby securing the intrauterine balloon within the uterus of the patient; and moving the rigid shaft, thereby manipulating the uterus of the patient via the inflated intrauterine balloon, and removing the uterus and cervix from the patient via the vaginal cavity after the vaginal-cervical junction has been circumferentially incised by proximally displacing the rigid shaft relative to the vagina while the inflated intrauterine balloon is secured within the uterus.

In accordance with yet another aspect of the disclosed inventions, a method is provided for performing a hysterectomy on a patient using a colpotomy cup assembly having a distal-facing surface, an ablation electrode associated with the colpotomy cup assembly, and a ground electrode having a region disposed on the distal-facing surface of the colpotomy cup assembly having a cleaved region disposed on the distal facing surface of the colpotomy cup assembly in circumferential alignment with the ablation electrode, the method including introducing the cutting head into a vaginal cavity of the patient; puncturing through the vaginal-cervical junction with the ablation electrode into the abdominal cavity of the patient; applying bipolar electrical ablation energy between the ablation electrode and the ground electrode; rotating the ablation electrode relative to the vaginal cavity while the bipolar electrical ablation energy is applied between the ablation electrode and the ground electrode, thereby circumferentially incising the vaginal-cervical junction to transect the uterus and cervix from the vagina of the patient; and removing the uterus and cervix from the patient, e.g., through the vaginal cavity. Without limitation, the cutting head may be distally advanced to the apex of the vaginal cavity of the patient until the colpotomy cup assembly abuts against vaginal fornices of the patient and receives a cervix of the patient. Without limitation, the ablation electrode may be provided with a blunt tip, wherein the distal portion of the ablation electrode is distally advanced to puncture the vaginal-cervical junction of the patient while the bipolar electrical ablation energy is conveyed between the ablation electrode and the ground electrode.

The method may further include insufflating the abdominal cavity; and sealing the vaginal cavity with a pneumo-occluder prior to circumferentially incising the vaginal-cervical junction of the patient, thereby preventing insufflation gas from escaping the abdominal cavity from the patient through the vaginal cavity after the vaginal-cervical junction is circumferentially incised.

The method may further include introducing an intrauterine balloon affixed to a rigid shaft through the vaginal cavity of the patient; guiding the intrauterine balloon through the cervix of the patient and into the uterus of the patient; inflating the intrauterine balloon before circumferentially incising the vaginal-cervical junction of the patient, thereby securing the intrauterine balloon within the uterus of the patient; and moving the rigid shaft, thereby manipulating the uterus of the patient via the inflated intrauterine balloon, and removing the uterus and cervix from the patient via the vaginal cavity after the vaginal-cervical junction has been circumferentially incised by proximally displacing the rigid shaft relative to the vagina while the inflated intrauterine balloon is secured within the uterus.

In accordance with a still further aspect of the disclosed inventions, a method is provided for performing a hysterectomy on a patient, the method comprising: introducing a triangular, non-compliant, intrauterine balloon affixed to a rigid shaft through the vaginal cavity of the patient, guided through the cervix of the patient, and into the uterus of the patient; inflating the intrauterine balloon before circumferentially incising the vaginal-cervical junction of the patient, thereby securing the intrauterine balloon within the uterus of the patient; circumferentially incising a vaginal-cervical junction between the vagina and the cervix of the patient to transect a uterus a cervix from a vagina of the patient; and removing the uterus and cervix from the patient via the vaginal cavity after the vaginal-cervical junction has been circumferentially incised by proximally displacing the rigid shaft relative to the vagina while the inflated intrauterine balloon is secured within the uterus. Without limitation, the method may include moving the rigid shaft, thereby manipulating the uterus of the patient via the inflated intrauterine balloon. Without limitation, the method may further comprise: insufflating the abdominal cavity; and sealing the vaginal cavity prior to circumferentially incising the vaginal-cervical junction of the patient, thereby preventing insufflation gas, when the vaginal-cervical junction is being circumferentially incised, from escaping the abdominal cavity from the patient through the vaginal cavity.

In accordance with a yet further aspect of the disclosed inventions, a method is provided for performing a hysterectomy on a patient using a cutting head that includes a colpotomy cup assembly, and a cutting element having a pre-curved distal portion associated with the colpotomy cup assembly, the method comprising: introducing the cutting head into a vaginal cavity of the patient; distally advancing the cutting head to the apex of the vaginal cavity of the patient; distally advancing the cutting element from a stored position to a deployed position; imparting a radially outward curvature on the distal portion of the cutting element as the cutting element is distally advanced from the stored position to the deployed position; puncturing through a vaginal-cervical junction with the cutting element into an abdominal cavity of the patient; rotating the cutting element relative to the vaginal cavity, thereby circumferentially incising the vaginal-cervical junction to transect the uterus and cervix from the vagina of the patient; and removing the uterus and cervix from the patient, e.g., through the vaginal cavity. The cutting head may be distally advanced to the apex of the vaginal cavity of the patient until the colpotomy cup assembly abuts against vaginal fornices of the patient and receives a cervix of the patient. The cutting head may be configured so that the cutting element is in the deployed position, a first acute angle (e.g., in a range of 15°-70°) is formed between a tangent at a distal tip of the cutting element and the longitudinal axis of the vaginal cavity of the patient. The cutting element, when in the stored position, may form a second acute angle with an exterior profile of the colpotomy cup assembly, and the exterior profile of the colpotomy cup assembly may form a third acute angle with the longitudinal axis of the elongated shaft. 228. The cutting element may be temporarily locked in a selected one of a plurality of positions.

The method may further include insufflating the abdominal cavity; and sealing the vaginal cavity with a pneumo-occluder prior to circumferentially incising the vaginal-cervical junction of the patient, thereby preventing insufflation gas, when the vaginal-cervical junction is being circumferentially incised, from escaping the abdominal cavity from the patient through the vaginal cavity. The method may further include retracting the distal portion of the cutting element within the colpotomy cup assembly while the cutting head is distally advanced to the apex of the vaginal cavity of the patient; and distally advancing the distal portion of the cutting element from the colpotomy cup assembly to puncture the vaginal-cervical junction of the patient with the cutting element.

The method may further include applying electrical ablation energy to the cutting element while the cutting element circumferentially incises the vaginal-cervical junction of the patient. For example, and without limitation, the method may include applying the electrical ablation energy to the cutting element to puncture the vaginal-cervical junction with the cutting element after the vagina-cervical junction has been tented within the abdominal cavity of the patient. A ground electrode may be disposed on the colpotomy cup assembly, in which case the electrical ablation energy may be applied between the cutting element and the ground electrode.

The method may further include introducing an intrauterine balloon affixed to a rigid shaft through the vaginal cavity of the patient; guiding the intrauterine balloon through the cervix of the patient and into the uterus of the patient; inflating the intrauterine balloon before circumferentially incising the vaginal-cervical junction of the patient, thereby securing the intrauterine balloon within the uterus of the patient; and moving the rigid shaft, thereby manipulating the uterus of the patient via the inflated intrauterine balloon, and removing the uterus and cervix from the patient via the vaginal cavity after the vaginal-cervical junction has been circumferentially incised by proximally displacing the rigid shaft relative to the vagina while the inflated intrauterine balloon is secured within the uterus.

Although particular embodiments of the disclosed inventions have been shown and described herein, it will be understood by those skilled in the art that they are not intended to limit the disclosed inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

The invention claimed is:

1. A colpotomy device, comprising:

an elongated shaft having a proximal end and a distal end;

a handle assembly comprising a handle body mechanically coupled to the proximal end of the elongated shaft, and a mechanical deployment actuator having a deployment mechanism slidably disposed on the handle body and a brake that are circumferentially spaced apart from each other and are configured for rotating, in unison, with the handle body about a longitudinal axis of the elongate shaft;

a cutting head mechanically coupled to the distal end of the elongated shaft, the cutting head configured for being positioned at the distal end of a vaginal cavity of a patient, the cutting head comprising:

a colpotomy cup; and a cutting element slidably coupled to the colpotomy cup, such that the cutting element is configured for being distally advanced from a stored position, wherein a distal portion of the cutting element is housed within the colpotomy cup, to a deployed position, wherein the distal portion of the cutting element extends distally from the colpotomy cup; and a sleeve slidably disposed around the elongated shaft between the colpotomy cup and the handle assembly, wherein a proximal portion of the cutting element is affixed to a distal portion of the sleeve and the deployment mechanism and the brake are mechanically coupled to a proximal portion of the sleeve, such that when the deployment mechanism is slid in the distal direction relative to the handle body, the sleeve slides distally relative to the elongated shaft, thereby distally advancing the cutting element from the stored position to the deployed position, and the brake slides relative to the handle body in the distal direction to releasably lock the cutting element in a position between the stored position and the deployed position.

2. The colpotomy device of claim 1, wherein the cutting element is an ablation electrode, and wherein the handle assembly comprises an electrical ablation port disposed on the handle body, the electrical ablation port having a first electrical terminal, the colpotomy device further comprising a first electrical wire electrically coupled between the first electrical terminal of the electrical ablation port and the ablation electrode, wherein the first electrical wire is associated with an outer surface of the sleeve and the deployment mechanism, such that, when the deployment mechanism is slid in the distal direction relative to the handle body, the sleeve, along with the first electrical wire, slides distally relative to the elongated shaft.

3. The colpotomy device of claim 2, wherein the electrical ablation port has a second electrical terminal, the colpotomy device further comprising:

a ground electrode mounted to the colpotomy cup; and a second electrical wire electrically coupled between the second electrical terminal of the electrical ablation port and the ground electrode, wherein the second electrical wire is disposed between the sleeve and the elongated shaft.

4. The colpotomy device of claim 3, wherein the sleeve comprises a channel extending longitudinally through a wall of the sleeve, wherein the second electrical wire is disposed within the channel.

5. The colpotomy device of claim 2, wherein the first electrical wire is spiraled around the electrode sleeve.

6. The colpotomy device of claim 1, wherein the handle body has a slot, and wherein the deployment mechanism comprises a slidable external thumb piece that resides outside of the handle body, a block to which the external thumb piece is affixed, the block being slidably disposed within the slot, the deployment mechanism further comprising a resilient arm distally extending from the block and affixed to the proximal end of the sleeve.

7. The colpotomy device of claim 1, wherein the handle body has a cavity, a pair of slots extending along lateral sides of the cavity, and a series of teeth inset along each of the pair of slots, and wherein the brake comprises a block slidably disposed within the cavity, a pair of spring arms extending proximally from the block, the pairs of spring arms respectively having lateral detents that interact with the series of teeth inset along the pair of slots, the brake further comprising a resilient arm distally extending from the block and affixed to the proximal end of the sleeve.

8. The colpotomy device of claim 1, wherein the brake is clocked 180 degrees from the cutting element.

9. The colpotomy device of claim 1, further comprising:

a rigid shaft slidably disposed within a lumen of the elongated shaft and extending proximally through the handle assembly; and a triangular, non-compliant, intrauterine balloon affixed to a distal end of the rigid shaft distal to the cutting head, the intrauterine balloon configured for being inflated within the uterus of the patient, such that the uterus may be mechanically manipulated when the rigid shaft is moved.

10. The colpotomy device of claim 9, wherein the triangular, non-compliant, intrauterine balloon, when inflated within the uterus of the patient, is sized, such that uterus, when the vaginal-cervical junction has been circumferentially incised, can be pulled out from the vagina by proximally displacing the rigid shaft relative to the vagina.

11. The colpotomy device of claim 1, wherein the colpotomy cup includes an outer cup portion and an inner cup portion rotatable within the outer cup portion about a longitudinal axis of the elongated shaft, and wherein the cutting element is mechanically coupled to the inner cup portion, such that the cutting element is configured for, when the inner cup portion is rotated within the outer cup portion, rotating along with the inner cup portion, thereby circumferentially incising a vaginal-cervical junction between the vagina and the cervix of the patient.

12. The colpotomy device of claim 1, wherein the distal portion of the cutting element has a blunt tip, such that the cutting element is configured for causing a vaginal-cervical junction between the vagina and the cervix of the patient to tent within an abdominal cavity of the patient when the blunt tip of the cutting element is distally advanced from the stored position against the vaginal-cervical junction.

13. The colpotomy device of claim 1, wherein the colpotomy cup has a distal-facing surface, wherein the cutting element is an ablation electrode, and the colpotomy device further comprises a ground electrode having a partially cleaved region disposed on the distal facing surface of the colpotomy cup in circumferential alignment with, and adjacent to, the ablation electrode.

14. The colpotomy device of claim 13, wherein the colpotomy cup comprises a reduced-diameter annular boss, and wherein the distal-facing surface of the colpotomy cup is a distal-facing surface of the reduced-diameter annular boss, and wherein the colpotomy cup further comprises a raised electrode platform disposed on the reduced-diameter annular boss of the colpotomy cup, the raised electrode platform configured for maintaining a minimum radial distance between the ablation electrode and the ground electrode disposed on the distal-facing surface of the colpotomy cup.

15. The colpotomy device of claim 1, wherein the distal portion of the cutting element is pre-curved, such that a radially outward curvature is imparted on the distal portion of the cutting element as the cutting element is distally advanced from the stored position to the deployed position.

16. The colpotomy device of claim 15, wherein, when the cutting element is in the deployed position, a first acute angle in the range of 15°-70° is formed between a tangent at a distal tip of the cutting element and the longitudinal axis of the elongated shaft.

17. The colpotomy device of claim 1, wherein the deployment mechanism comprises a first resilient arm affixed to the proximal end of the sleeve, such that when the deployment mechanism is slid in the distal direction relative to the handle body, the cutting element is distally advanced from the stored position to the deployed position; and wherein the brake comprises a second resilient arm affixed to the proximal portion of the sleeve, such that when the deployment mechanism is slid in the distal direction relative to the handle body, the brake slides relative to the handle body in the distal direction.

18. The colpotomy device of claim 17, wherein the first and second resilient arms are affixed to the proximal portion of the sleeve at locations that are circumferentially offset from each other.

19. The colpotomy device of claim 1, wherein the brake is clocked greater than 0 degrees from the cutting element.

20. The colpotomy device of claim 19, wherein the brake is clocked less than 180 degrees from the cutting element.

* * * * *